US009371568B2

(12) United States Patent
Gaulis et al.

(10) Patent No.: US 9,371,568 B2
(45) Date of Patent: *Jun. 21, 2016

(54) MARKERS ASSOCIATED WITH HUMAN DOUBLE MINUTE 2 INHIBITORS

(71) Applicant: Novartis AG, Basel (CH)

(72) Inventors: Swann Gaulis, Basel (CH); Sebastien Jeay, Niffer (FR)

(73) Assignee: Novartis AG, Basel (CH)

( * ) Notice: Subject to any disclaimer, the term of this patent is extended or adjusted under 35 U.S.C. 154(b) by 127 days.

This patent is subject to a terminal disclaimer.

(21) Appl. No.: 13/950,881

(22) Filed: Jul. 25, 2013

(65) Prior Publication Data

US 2014/0038986 A1 Feb. 6, 2014

Related U.S. Application Data

(60) Provisional application No. 61/677,859, filed on Jul. 31, 2012.

(51) Int. Cl.
| | |
|---|---|
| *C12Q 1/68* | (2006.01) |
| *C12Q 1/00* | (2006.01) |
| *G01N 33/53* | (2006.01) |
| *C07D 401/12* | (2006.01) |
| *G01N 33/68* | (2006.01) |
| *G01N 33/574* | (2006.01) |
| *A61K 31/496* | (2006.01) |
| *G01N 33/50* | (2006.01) |

(52) U.S. Cl.
CPC ............ *C12Q 1/6886* (2013.01); *A61K 31/496* (2013.01); *C07D 401/12* (2013.01); *C12Q 1/6883* (2013.01); *G01N 33/5011* (2013.01); *G01N 33/574* (2013.01); *G01N 33/5748* (2013.01); *G01N 33/6875* (2013.01); *C12Q 2600/106* (2013.01); *C12Q 2600/136* (2013.01); *C12Q 2600/158* (2013.01); *G01N 2800/52* (2013.01)

(58) Field of Classification Search
None
See application file for complete search history.

(56) References Cited

U.S. PATENT DOCUMENTS

2006/0211757 A1 9/2006 Wang et al.
2015/0159222 A1* 6/2015 Gaulis et al. ............... 435/7.23

FOREIGN PATENT DOCUMENTS

WO WO 2011/076786 6/2011
WO WO 2011076786 A1 * 6/2011

OTHER PUBLICATIONS

Tovar (Proceedings of the National Academy of Sciences, 2006, 103:1888-1893).*
MCE (MedChemExpress_Nutlin-3, 2015).*
Ramaswamy et al. (Proceedings of the National Academy of Sciences, 2001, 26:15149-15154).*
Ertel et al. (Molecular Cancer, 2006, 5:55; pages are numbered 1-13).*
GenePattern (GenePattern_2003).*
GeneAnnot (http://genecards.weizmann.ac.il/cgi-bin/geneannot/GA_search.pl?array=HG-U133&keyword_type=gene_symbol&keyword=S100A7&target=integrated&.submit=Submit+Query, HG_U95; 2015).*
GeneAnnot (http://genecards.weizmann.ac.il/cgi-bin/geneannot/GA_search.pl?array=HG-U133&keyword_type=gene_symbol&keyword=S100A7&target=integrated&.submit=Submit+Query; HG_U133; 2015).*
de Rozieres et al., "The Loss of mdm2 Induces p53 Mediated Apoptosis" *Oncogene* 19:1691-1697, 2000.
Fakharzadeh et al., "Tumorigenic Potential Associated with Enhanced Expression of a Gene that is Amplified in a Mouse Tumor Cell Line" *EMBO Journal* 10(6):1565-1569, 1991.
Haupt et al., "Mdm2 Promotes the Rapid Degradation of p53" *Nature* 387:296-299, May 1997.
Hollstein et al., "p53 Mutations in Human Cancers" *Science* 253:49-53, 1991.
Hollstein et al., "Database of p53 Gene Somatic Mutations in Human Tumors and Cell Lines" *Nucleic Acid Research* 22(17):3551-3555, 1994.
Levine et al., "p53, the Cellular Gatekeeper for Growth and Division" *Cell* 88:323-331, 1997.
Momand et al., "The MDM2 Gene Amplification Database" *Nucleic Acids Research* 26(15):3453-3459, 1998.
Piette et al., "Mdm2: Keeping p53 Under Control" *Oncogene* 15:1001-1010, Jul. 1997.
Onel and Cordon-Cardo, "MDM2 and Prognosis" *Molecular Cancer Research* 2(1):1-8, 2004.
Varley "Germline TP53 Muations and Li-Fraumeni Syndrome" *Human Mutation* 21:313-320, 2003.
Vassilev et al., "In Vivo Activation of the p53 Pathway by Small-Molecule Antagonists of MDM2" *Science* 303:844-848, 2004.
Volgelstein et al, "Surfing the p53 Network" *Nature* 408:307-310, 2000.
Vu and Vassilev et al., "Small-Molecule Inhibitors of the p53-MDM2 Interaction" *Current Topics in Microbiology and Immunology* 348:151-172, 2011.
Wu et al., "The p53-mdm-2 Autoregulatory Feedback Loop" *Genes Dev.* 7:1126-1132, 1993.
Zhang et al., "Efficient Activation of p53 Pathway in A549 Cells Exposed to L2, a Novel Compound Targeting p53-MDM2 Interaction" *Anticancer Drugs* 20(6)416-424, 2009.
Shangary et al., "Reactivation of p53 by a Specific MDM2 Antagonist (MI-43) Leads to p21-Mediated Cell Cycle Arrest and Selective Cell Death in Colon Cancer" *Mol Cancer Ther* 7(6):1533-1542, 2008.
Furet et al., "The Central Valine Concept Provides an Entry in a New Class of Non Peptide Inhibitors of the p53-MDM2 Interaction" *Bio Org Med Chem Let* 22:3498-3502, 2012.
Carol et al., Initial Testing of the MDM2 Inhibitor RG7112 by the Pediatric Preclinical Testing Program *Pediatr Blood Cancer* 60:633-641, 2013.

(Continued)

*Primary Examiner* — Julie Wu
(74) *Attorney, Agent, or Firm* — David A. Carpenter

(57) ABSTRACT

The invention provides methods of monitoring differential gene expression of biomarkers to determine patient sensitivity to Human Double Minute inhibitors (MDM2i), methods of determining the sensitivity of a cell to an MDM2i by measuring biomarkers and methods of screening for candidate MDM2i.

3 Claims, 15 Drawing Sheets

(56) References Cited

OTHER PUBLICATIONS

Barrentina et al., "The Cancer Cell Line Encyclopedia Enables Predictive Modelling of Anticancer Drug Sensitivity" *Nature* 483:603-607, 2012.

Frey and Dueck "Clustering by Passing Messages Between Data Points" *Science* 315:972-976, Feb. 2007.

Tovar et al. "Small Molecule MDM2 Antagonists Reveal Aberrant p53 Signaling in Cancer: Implications for Therapy" *Proceedings of the National Academy of Sciences* 103(6):1888-1893, Feb. 7, 2006.

Lu et al. "MDM2 and MDMX Status as a Determinant of in vitro Cellular Sensitivity to MDM2 Antagonists in Human Tumour Cell Lines" *European Journal of Cancer Supplemental Pergamon*, Oxford, GB 6(12):137 Oct. 23, 2008.

Vassilev, "MDM2 Inhibitors for Cancer Therapy" *Trends in Molecular Medicine* 13(1):23-31, Nov. 28, 2006.

Affymetrix "Data sheet GeneChip200 Human Genome Arrays" Internet Citation, 2004, pp. 1-4, URL:http://media.affymetrix.com/support/technical/datasheets/human_datasheet.pdf.

\* cited by examiner

Figure 1A

| TR-FRET | MDM2i(1) | MDM2i(2) |
|---|---|---|
| $IC_{50}$ (nM) | 1.7 | 1.3 |
| $K_i$ (nM) | 1.3 | 1.1 |
| $K_{on}$ (M$^{-1}$.s$^{-1}$) × 10$^6$ | 37 | 70 |
| $K_{off}$ (s$^{-1}$) | 0.071 | 0.084 |
| $T_{1/2}$ (s) | 10 | 8 |

Figure 1B

| Assay | MDM2i(1) | MDM2i(2) |
|---|---|---|
| Cell proliferation inhibition: | | |
| - $IC_{50}$ in SJSA-1 (p53$^{WT/WT}$) (µM) | 0.29 | 0.34 |
| - $IC_{50}$ in SAOS2 (p53$^{-/-}$) (µM) [Fold difference] | 19.75 [68x] | 17.06 [50x] |
| - $IC_{50}$ in HCT116 (p53$^{WT/WT}$) (µM) | 0.35 | 0.44 |
| - $IC_{50}$ in HCT116 (p53$^{-/-}$) (µM) [Fold difference] | 13.37 [38x] | 10.60 [24x] |
| GRIP p53 translocation assay: | | |
| - $IC_{50}$ with 10% FCS (µM) | 0.27 | 0.36 |

Figure 2: Sensitivity of cells to MDM2i(2) and p53 mutational status, mt (mutant) or wild type (wt).

The mt panel displays the MDM2i(2) sensitivity profiles for p53 mutated CCLE cell lines, the wt panel displays the MDM2i(2) sensitivity profiles for p53 wild-type CCLE cell lines. Amax is defined as the maximal effect level (the inhibition at the highest tested MDM2i(2) concentration, calibrated to a reference inhibitor), and IC50 is defined as of the µM concentration at which MDM2i(2) response reached an absolute inhibition of -50 with respect to the reference inhibitor. Cell line count broken down by MDM2i(2) chemical sensitivity and p53 mutation status, and associated statistics: Data is also displayed as a contingency table with associated statistics.

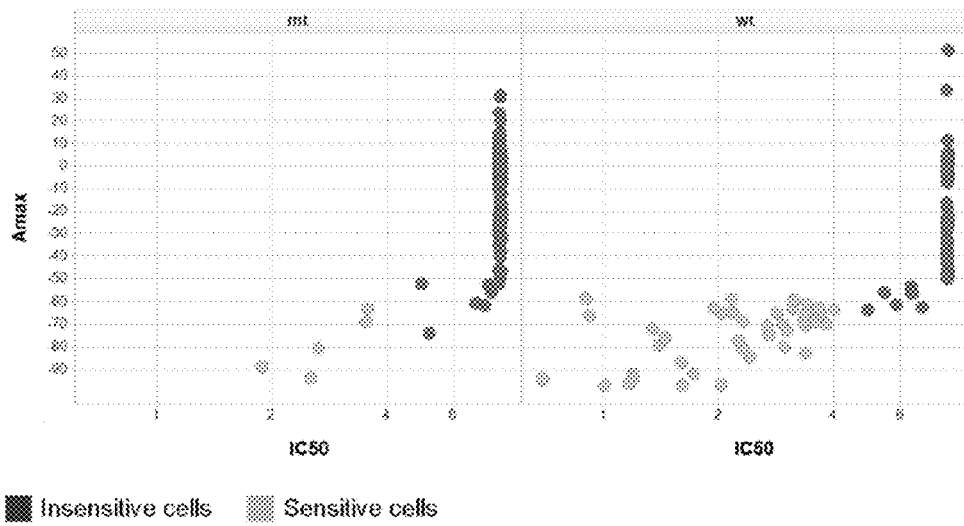

| MDM2i(2) | wt | mt |
|---|---|---|
| Insensitive | 70 | 239 |
| Sensitive | 42 | 5 |

P-value = 6.3e-19 (Fisher's Exact Test)

Odds ratio estimate = 28.38

Figure 3: Selected MDM2i chemical sensitivity predictive biomarkers and their associated statistics. The gene identities are official HUGO symbols. The 'Expr' prefix indicates these biomarkers are of the transcript expression type.

| Biomarkers | Fold_change | Wilcoxon_pval | Wilcoxon_pval_adjust |
|---|---|---|---|
| Expr MDM2 | 2.18 | 1.71E-18 | 3.09E-14 |
| Expr CDKN1A | 3.88 | 4.16E-15 | 3.76E-11 |
| Expr ZMAT3 | 2.81 | 1.98E-14 | 1.20E-10 |
| Expr DDB2 | 2.55 | 2.71E-14 | 1.22E-10 |
| Expr FDXR | 2.42 | 2.98E-13 | 1.08E-09 |
| Expr RPS27L | 1.97 | 4.08E-13 | 1.23E-09 |
| Expr BAX | 2.12 | 7.12E-13 | 1.84E-09 |
| Expr RRM2B | 2.06 | 1.88E-12 | 4.25E-09 |
| Expr SESN1 | 2.27 | 5.17E-12 | 1.04E-08 |
| Expr CCNG1 | 1.69 | 2.65E-11 | 4.81E-08 |
| Expr XPC | 1.62 | 9.47E-11 | 1.56E-07 |
| Expr TNFRSF10B | 1.91 | 2.42E-09 | 3.30E-06 |
| Expr AEN | 1.46 | 2.55E-09 | 3.30E-06 |

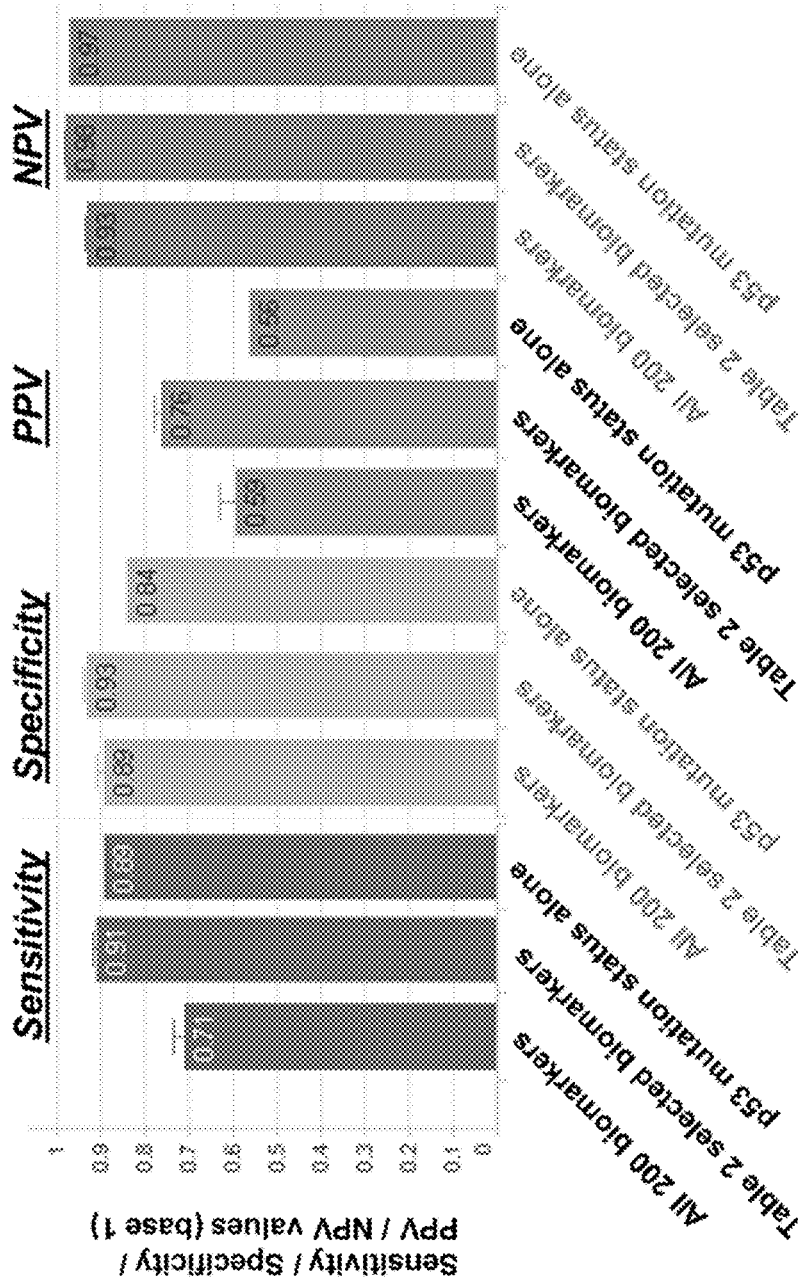

Figure 5: cross-validation performances of MDM2i(2) chemical sensitivity predictive models.
Performances of models derived from three predictive feature sets are evaluated using sensitivity (fraction of correctly predicted sensitive cell lines), specificity (fraction of correctly predicted insensitive cell lines), PPV (positive predicted value, fraction of sensitive cell lines predicted as such) and NPV (negative predictive value, fraction of insensitive cell lines predicted as such). Error bars are one standard deviation of the means over the 5 iterations of 5-fold cross-validations. The model using the 13 selected biomarker depicted in Table 2 achieves better predictivity of MDM2i(2) chemical sensitivity, and this independently of the performance measure, but most strikingly when PPV is considered as the performance indicator.

FIGURE 6

Tumor cells displaying the p53 target gene signature are sensitive to MDM2i

| Cell Line Name | Primary Site | MDM2i Sensitivity Prediction | MDM2i(1) IC50, µM | MDM2i(2) IC50, µM | MDM2i(1)&(2) Consensus Sensitivity Call |
|---|---|---|---|---|---|
| SJSA-1 | bone | sensitive | 0.223 | 0.241 | sensitive |
| CCF-STTG1 | central_nervous_system | sensitive | 0.87 | 0.76 | sensitive |
| D283Med | central_nervous_system | sensitive | 0.193 | 0.181 | sensitive |
| BV-173 | haematopoietic_and_lymphoid_tissue | sensitive | 0.055 | 0.051 | sensitive |
| EOL-1 | haematopoietic_and_lymphoid_tissue | sensitive | 0.062 | 0.053 | sensitive |
| GDM-1 | haematopoietic_and_lymphoid_tissue | sensitive | 0.293 | 0.285 | sensitive |
| HH | haematopoietic_and_lymphoid_tissue | sensitive | 0.365 | 0.353 | sensitive |
| L-540 | haematopoietic_and_lymphoid_tissue | sensitive | 0.039 | 0.036 | sensitive |
| MHH-CALL-4 | haematopoietic_and_lymphoid_tissue | sensitive | 0.105 | 0.079 | sensitive |
| MV-4-11 | haematopoietic_and_lymphoid_tissue | sensitive | 0.88 | 0.961 | sensitive |
| NALM-6 | haematopoietic_and_lymphoid_tissue | sensitive | 0.063 | 0.079 | sensitive |
| RS4;11 | haematopoietic_and_lymphoid_tissue | sensitive | 0.177 | 0.297 | sensitive |
| SUP-B15 | haematopoietic_and_lymphoid_tissue | sensitive | 0.135 | 0.167 | sensitive |
| A-498 | kidney | sensitive | 3.943 | NA | insensitive |
| CAKI-1 | kidney | sensitive | 4.721 | NA | insensitive |
| CAL-54 | kidney | sensitive | 0.544 | NA | sensitive |
| KMRC-2 | kidney | sensitive | 5.223 | NA | insensitive |
| OS-RC-2 | kidney | sensitive | 10 | NA | insensitive |
| A549 | lung | sensitive | 1.180 | NA | sensitive |
| DM-3 | pleura | sensitive | 10 | NA | insensitive |
| IST-MES1 | pleura | sensitive | 4.063 | NA | insensitive |
| JL-1 | pleura | sensitive | 1.421 | NA | sensitive |
| MSTO-211H | pleura | sensitive | 0.454 | NA | sensitive |
| A101D | skin | sensitive | 6.729 | 7.784 | insensitive |
| COLO-829 | skin | sensitive | 4.336 | 2.978 | insensitive |
| COLO-783 | skin | sensitive | 10 | 10 | insensitive |
| COLO-849 | skin | sensitive | 2.726 | 2.634 | sensitive |
| Hs 688(A)T | skin | sensitive | 10 | 10 | insensitive |
| Hs 834.T | skin | sensitive | 10 | 10 | insensitive |
| Hs 940.T | skin | sensitive | 1.434 | 2.666 | sensitive |
| IGR-1 | skin | sensitive | 6.095 | 6.131 | insensitive |
| MEL-JUSO | skin | sensitive | 0.666 | 0.801 | sensitive |
| SK-MEL-3 | skin | sensitive | 1.813 | 1.899 | sensitive |
| SK-MEL-31 | skin | sensitive | 1.222 | 1.275 | sensitive |
| UACC-257 | skin | sensitive | 2.143 | 2.106 | sensitive |
| UACC-62 | skin | sensitive | 0.624 | 0.74 | sensitive |

| Cell Line Name | Primary Site | MDM2i Sensitivity Prediction | MDM2i(1) IC50, µM | MDM2i(2) IC50, µM | MDM2i(1)&(2) Consensus Sensitivity Call |
|---|---|---|---|---|---|
| CAL-51 | breast | insensitive | 10.00 | 8.252 | sensitive |
| EFM-192A | breast | insensitive | 10 | 7.43 | insensitive |
| HCC202 | breast | insensitive | 7.396 | 7.395 | insensitive |
| GA-10 | haematopoietic_and_lymphoid_tissue | insensitive | 6.061 | 6.294 | insensitive |
| HDLM-2 | haematopoietic_and_lymphoid_tissue | insensitive | 10 | 9.859 | insensitive |
| JM1 | haematopoietic_and_lymphoid_tissue | insensitive | 0.997 | 1.102 | sensitive |
| KASUMI-1 | haematopoietic_and_lymphoid_tissue | insensitive | 8.273 | 7.437 | insensitive |
| VMRC-RCW | kidney | insensitive | 10 | NA | insensitive |
| H441 | lung | insensitive | 8.788 | 9.012 | insensitive |
| HCC-95 | lung | insensitive | 7.129 | NA | insensitive |
| NCI-H1568 | lung | insensitive | 8.203 | NA | insensitive |
| RERF-LC-KJ | lung | insensitive | 6.753 | 10 | insensitive |
| SW1990 | pancreas | insensitive | 10 | 9.734 | insensitive |
| NCI-H28 | pleura | insensitive | 2.627 | NA | sensitive |
| COLO-818 | skin | insensitive | 10 | 10 | insensitive |
| IGR-37 | skin | insensitive | 10 | 10 | insensitive |

Figure 7A
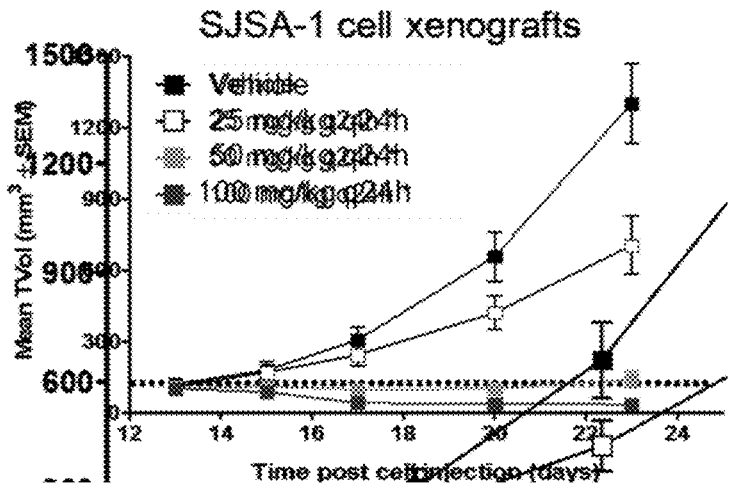
Figure 7B
| SJSA-1 tumor xenografts – 10 days of treatment | | |
|---|---|---|
| MDM2i(1) treatment | T/C (%) | Regression (%) |
| 25 mg/kg q24h | 50 | - |
| 50 mg/kg q24h | 3 | - |
| 100 mg/kg q24h | - | 65 |
Figure 7C
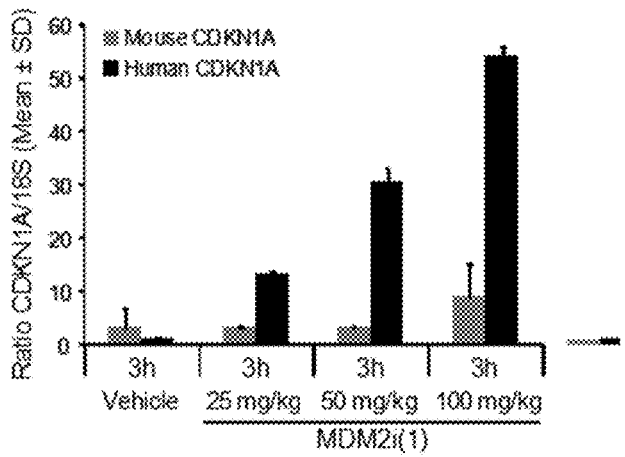

MDM2i(1) significantly increases p21 expression in SJSA-1 tumor bearing mice

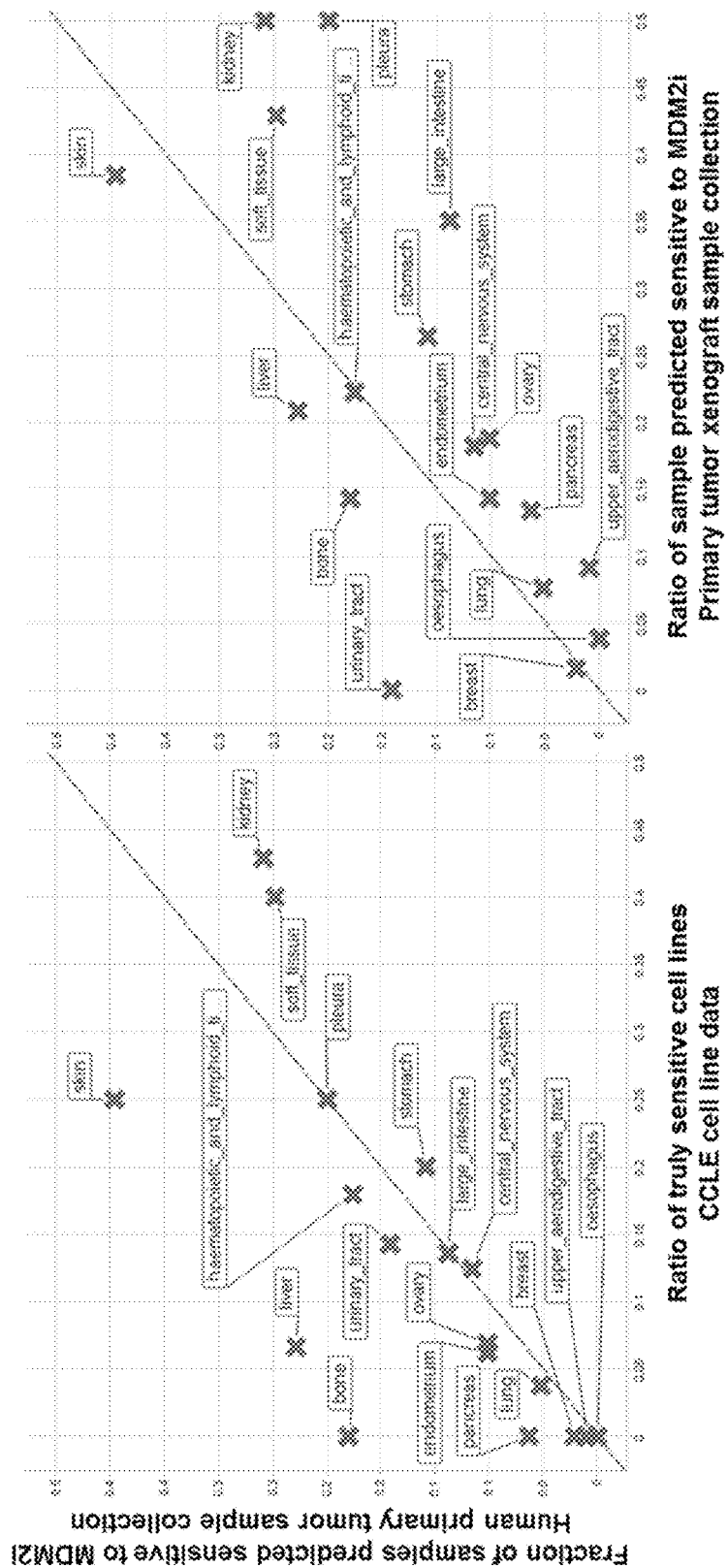

Figure 9: Lineage specific correlations of MDM2i chemical sensitivity predictions in human primary tumor collections and CCLE cell line data.
The left panel shows the correlation between the fractions of predicted sensitive samples from the human primary tumor sample collection and the observed sensitivity ratio in the cell line data. The right panel shows the correlation between the fractions of predicted sensitive samples from the human primary tumor sample collection and the predicted sensitive ratios in the primary tumor xenograft collection. Samples/Xenografts/Cell lines are organized by lineage. The dashed line is the identity line.

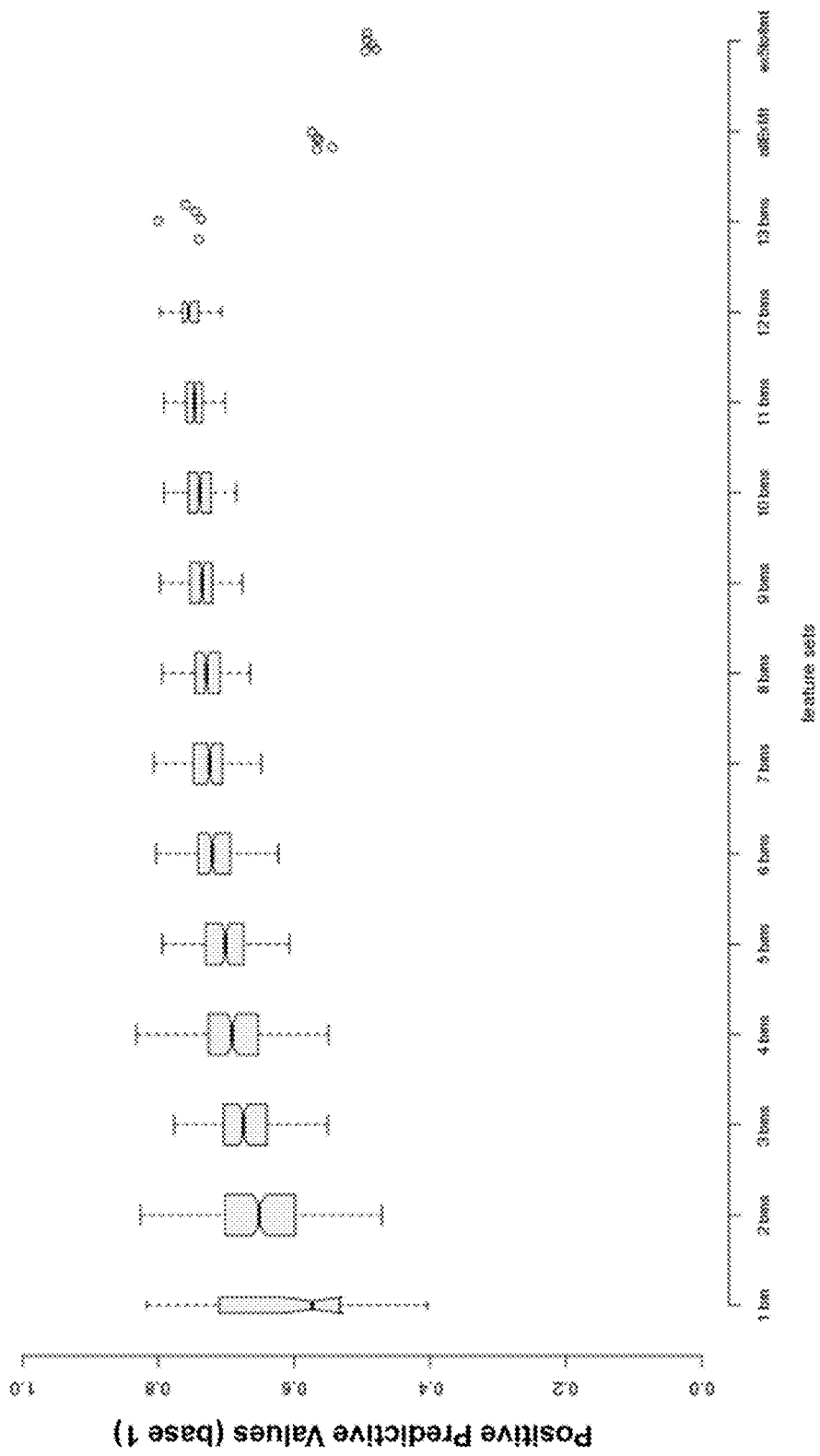

Figure 10: Positive Predicted Values achieved by MDM2ii(2) sensitivity predictive models built from multiple combinations of biomarkers.

The combinatorial and single-gene model PPVs are shown as box-and-whisker plots and compared to the PPVs given by the two p53 mutation status and thirteen biomarker models (the whiskers extend 1.5 times the interquartile range, the black line is the median, the notches are an estimation of the median confidence interval, the box width is proportional to the number of data points, the outliers are not shown; 'bm(s)': biomarker(s); 'allExMt': p53 all exon mutation model; 'ex5to8mt': p53 exon 5 to 8 mutation model).

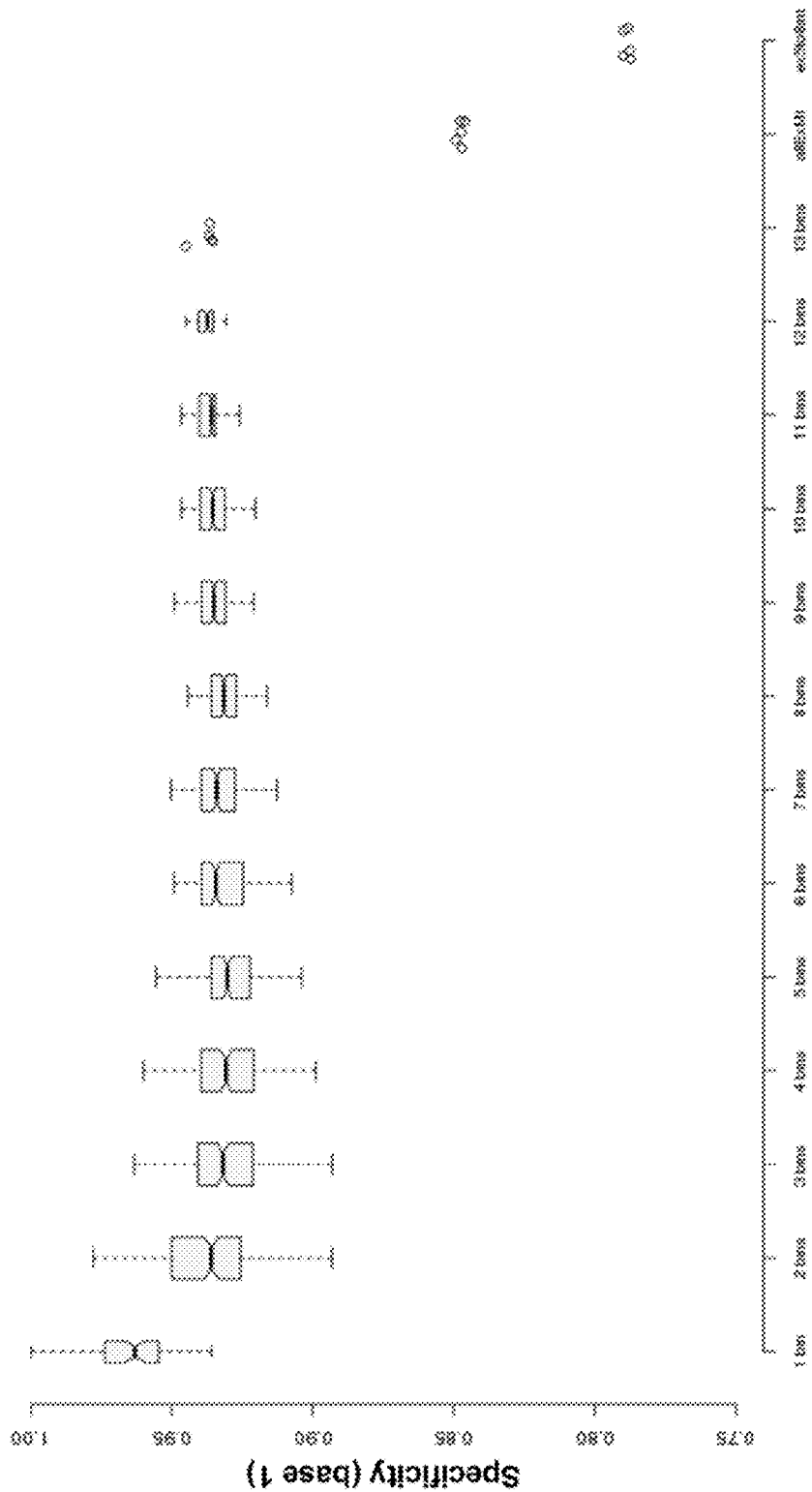

Figure 11: Specificities achieved by MDM2i(2) sensitivity predictive models built from multiple combinations of biomarkers.
The combinatorial and single-gene model specificities are shown as box-and-whisker plots and compared to the PPVs given by the two p53 mutation status and thirteen biomarker models (the whiskers extend 1.5 times the interquartile range, the black line is the median, the notches are an estimation of the median confidence interval, the box width is proportional to the number of data points, the outliers are not shown;'bm(s)': biomarker(s); 'allExMt': p53 all exon mutation model; 'ex5to8mt': p53 exon 5 to 8 mutation model).

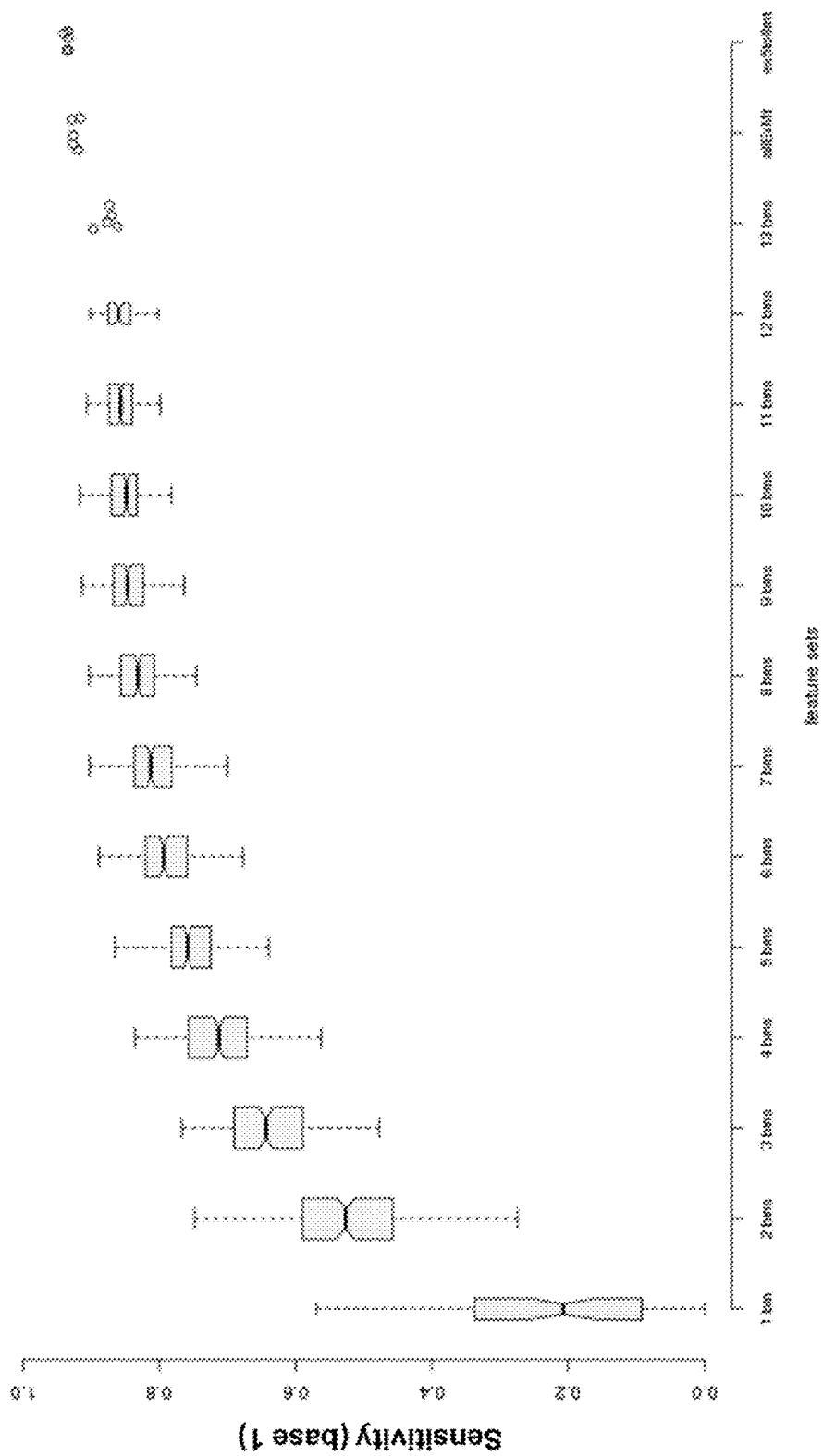

Figure 12: Sensitivities achieved by MDM2i(2) sensitivity predictive models built from multiple combinations of biomarkers.
The combinatorial and single-gene model sensitivities are shown as box-and-whisker plots and compared to the PPVs given by the two p53 mutation status and thirteen biomarker models (the whiskers extend 1.5 times the interquartile range, the black line is the median, the notches are an estimation of the median confidence interval, the box width is proportional to the number of data points, the outliers are not shown;'bm(s')': biomarker(s); 'allExMt': p53 all exon mutation model; 'ex5to8mt': p53 exon 5 to 8 mutation model).

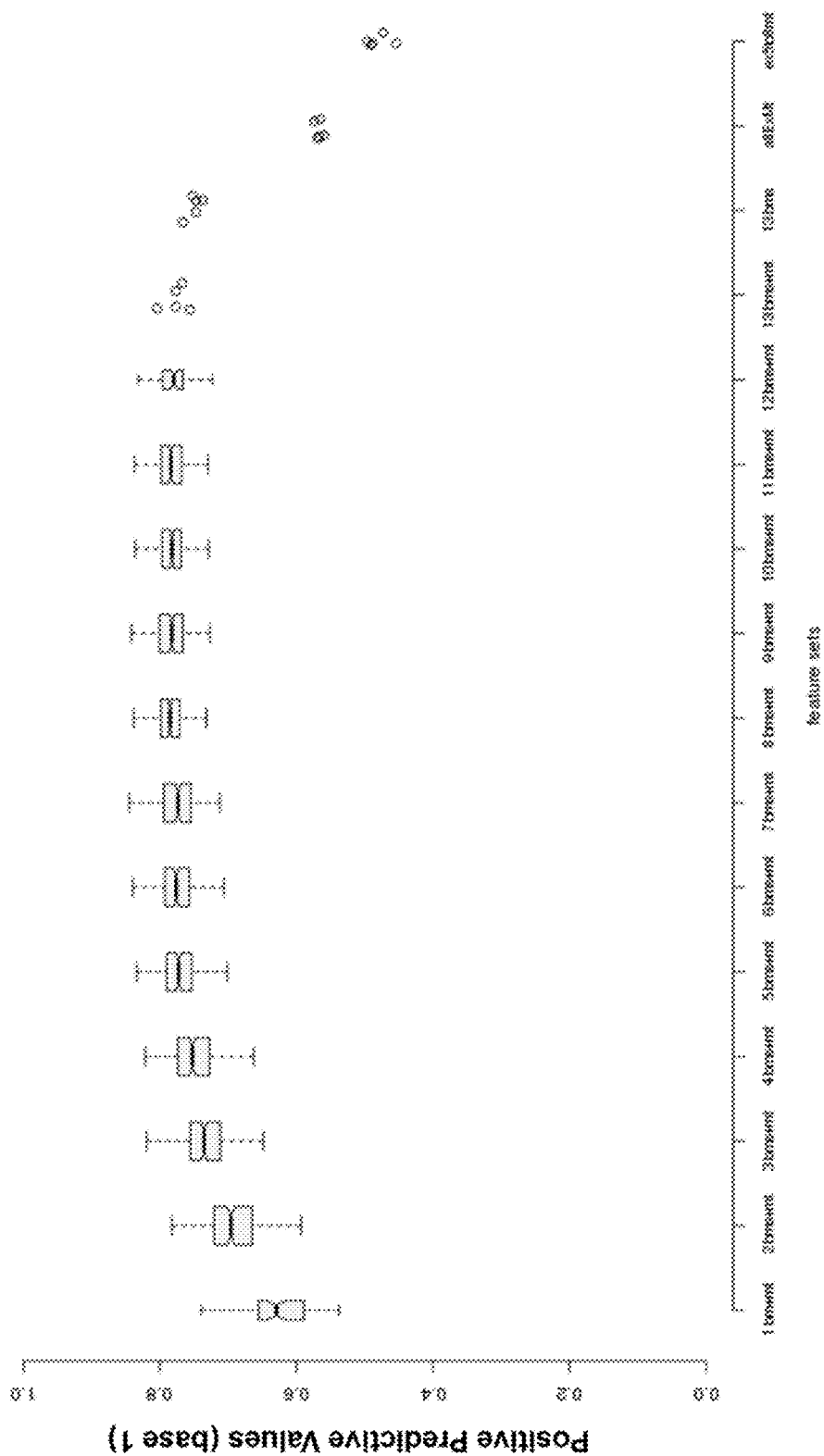
Figure 13: Positive Predicted Values achieved by MDM2i(2) sensitivity predictive models built from combining biomarkers with p53 mutation status.
For a description of the plot refer to Figure 10, 11 or 12; 'bm(s)': biomarker(s); 'mt': p53 exon 5 to 8 mutations; 'allExMt': p53 all exon mutation model; 'ex5to8mt': p53 exon 5 to 8 mutation model).

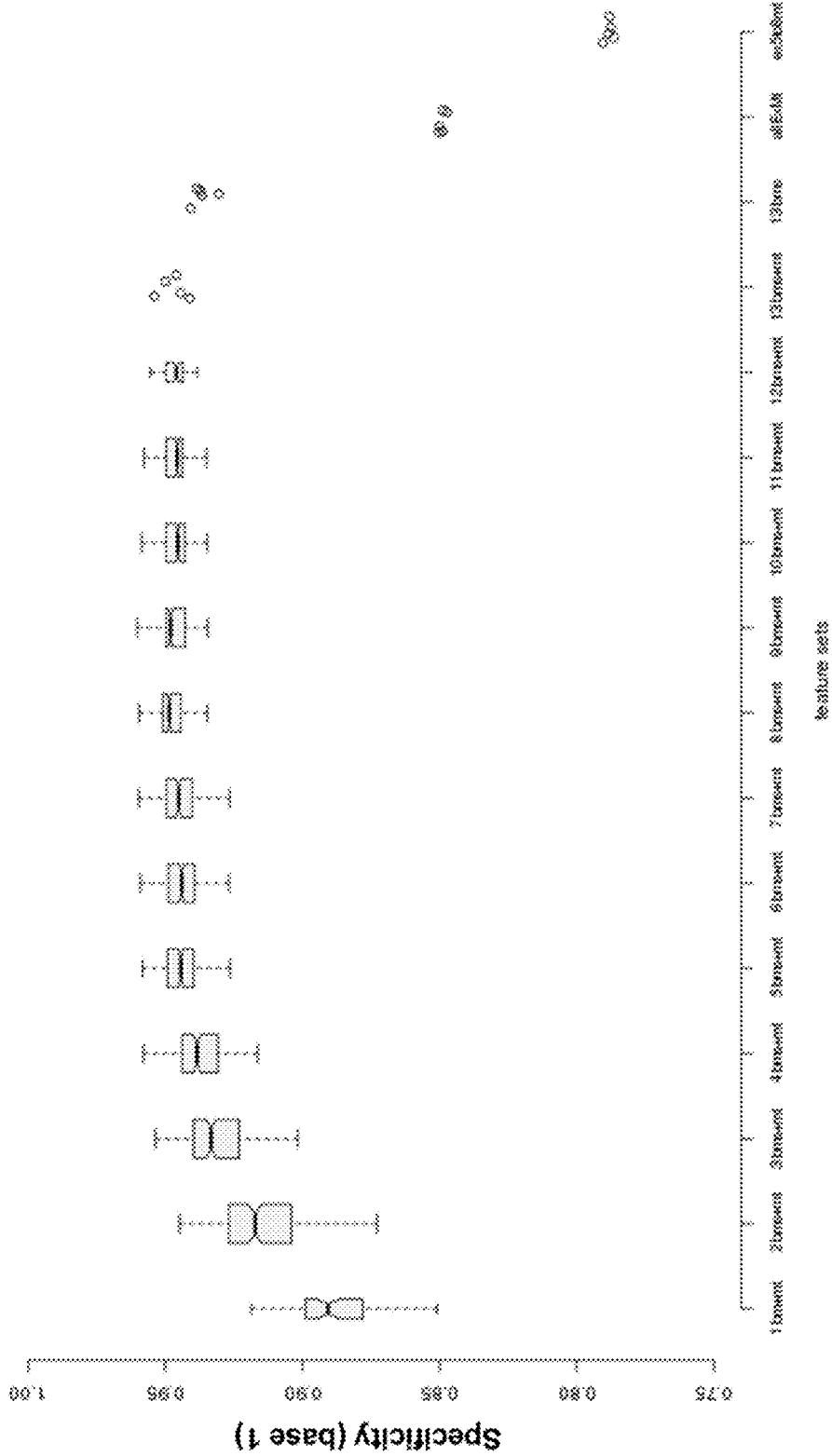
Figure 14: Specificities achieved by MDM2i(2) sensitivity predictive models built from combining biomarkers with p53 mutation status.
For a description of the plot refer to Figure 10, 11 or 12; 'bm(s)': biomarker(s); 'mt': p53 exon 5 to 8 mutations; 'allExMt': p53 all exon mutation model; 'ex5to8mt': p53 exon 5 to 8 mutation model).

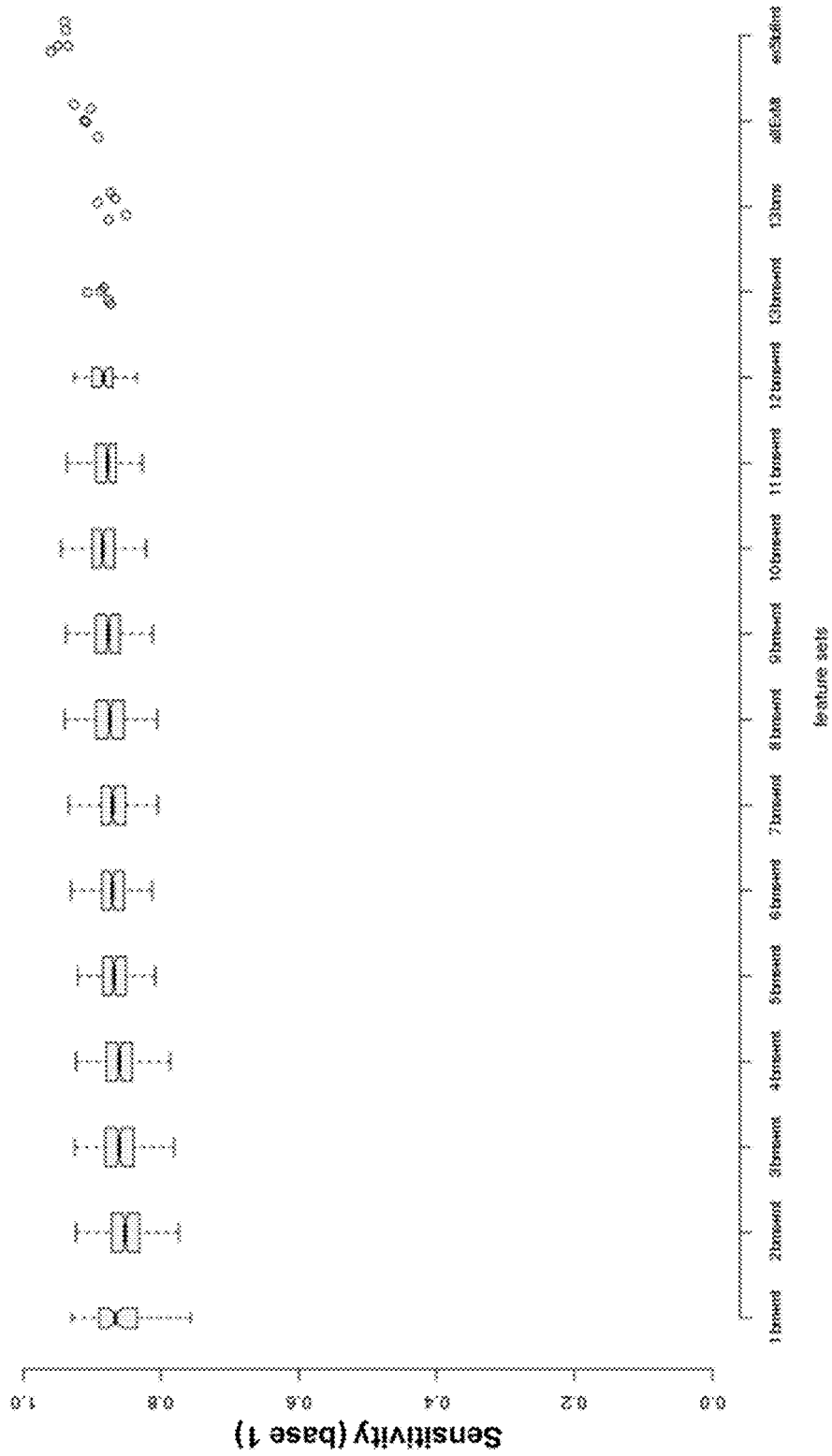
Figure 15: Sensitivities achieved by MDM2i(2) sensitivity predictive models built from combining biomarkers with p53 mutation status.
For a description of the plot refer to Figure 10, 11 or 12; 'bm(s)': biomarker(s); 'mt': p53 exon 5 to 8 mutations; 'allExMt': p53 all exon mutation model; 'ex5to8mt': p53 exon 5 to 8 mutation model).

MARKERS ASSOCIATED WITH HUMAN DOUBLE MINUTE 2 INHIBITORS

CROSS-REFERENCE TO RELATED APPLICATION

This application claims the benefit of priority to U.S. provisional application Ser. No. 61/677,859, filed Jul. 31, 2012, which is herein incorporated by reference.

FIELD OF THE INVENTION

The present invention relates to the field of pharmacogenomics, and the use of biomarkers useful in determining patient sensitivity prior to treatment, following patient response after treatment, cancer sensitivity and screening of compounds.

BACKGROUND p53, also known as tumor protein 53, is a tumor suppressor gene involved in the prevention of cancer, often referred to as the gatekeeper or guardian of the genome (Levine, Cell 1997, 88:323-331). The p53 gene encodes for a transcription factor that is normally quiescent, and becoming activated when the cell is stressed or damaged, such as when DNA damage incurred from a mutagen. If the cell is stressed or damaged, p53 acts to limit the damage, or barring that, trigger the apoptotic pathway so the damaged cell is eliminated and no longer a threat to the organism (Vogelstein et al., Nature 2000, 408:307-310). An analysis of different cancers showed that p53 is mutated in about 50% of human cancers (Hollstein et al., Nucleic Acids Res. 1994, 22:3551-3555: Hollstein et al., Science 1991, 253(5015): 49-53). Humans who are heterozygous for p53, with only a single functional copy, will develop tumors early in adulthood, a disorder known as Li-Fraumeni syndrome (Varley et al., Hum. Mutat. 2003, 21(3):313-320). However, as much as p53 regulates the cell's fate, p53 is regulated by another protein known as MDM2.

Double minute 2 protein (MDM2) was discovered as a negative regulator of p53 (Fakharzadeh et al., EMBO J. 1991, 10(6):1565-1565). MDM2 encodes an E3 ligase containing a p53 binding domain and a nuclear export signal sequence, and upon complexing with p53, removes it from the nucleus and ubiquitinylates it, which promotes the degradation of the p53 protein via the ubiquitin-proteosome pathway (Haupt et al., Nature 1997, 387(6630):296-299; Piette et al., Oncogene 1997 15(9):1001-1010). In addition, MDM2 directly inhibits the activity of p53 by binding to the p53 transactivation domain, also preventing p53 mediated gene expression (Wu et a., Genes Dev. 1993, 7:1126-1132). Thus, MDM2 regulates p53 in multiple ways.

MDM2 is overexpressed in a number of cancers, for example, liposarcoma, glioblastoma, and leukemia (Momand et al., Nucleic Acids Res. 1998, 26(15):3453-3459). Overexpression of MDM2 can interfere with the activities of p53, preventing apoptosis and growth arrest of the tumor (de Rozieres et al., Oncogene 2000, 19(13):1691-1697). Overexpression of MDM2 correlates with poor prognosis in glioma, and acute lymphocytic leukemia (Onel et al., Mol. Cancer Res. 2004, 2(1):1-8).

As MDM2 is an inhibitor of p53, therapeutics which prevent the binding of MDM2 to p53 would prevent the degradation of p53, allowing free p53 to bind and mediate gene expression in cancer cells, resulting in cell cycle arrest and apoptosis. There are previous reports of small molecule inhibitors of the p53-MDM2 interaction (Vassilev et al., Science, 2004, 303(5659):844-888; Zhang et al., Anticancer drugs, 2009 20(6):416-424; Vu et al., Curr. Topics Microbiol. Immuno., 2011, 348:151-172). The mode of binding of these compounds and a crystal structure of the human MDM2-Nutlin complex as well as a scaffold and pockets of the p53 binding site on MDM2 are also known (Vassilev, supra). The first of these MDM2 inhibitors, known as the Nutlins, bind MDM2 and occupy the p53 binding pocket, preventing the formation of the MDM2-p53 complex. This leads to less degradation of the p53 protein, and expression of p53 target genes. Cancer cell lines treated with Nutlins showed growth arrest and increased apoptosis. For example, the SJSA-1 osteosarcoma line contains amplified copies of the MDM2 gene. Treatment of this line with Nutlin-3 reduced proliferation and increased apoptosis (Vassilev et al., Science, 2004, 303(5659):844-888). The SJSA-1 cell line was used in creating xenographs in mouse. Administration of Nutlin-3 reduced xenograft growth by 90%. To investigate the effect the Nutlin compounds had on non-cancerous cells, human and mouse normal fibroblasts were treated with Nutlin-3 and while the proliferation of the cells was slowed, they retained their viability (Vassilev, supra).

Finding biomarkers which indicate which patient should receive a therapeutic is useful, especially with regard to cancer. This allows for more timely and aggressive treatment as opposed to a trial and error approach. In addition, the discovery of biomarkers which indicate that cells continue to be sensitive to the therapy after administration is also useful. These biomarkers can be used to monitor the response of those patients receiving the therapeutic. If biomarkers indicate that the patient has become insensitive to the treatment, then the dosage administered can be increased, decreased, completely discontinued or an additional therapeutic administered. As such, there is a need to develop biomarkers associated with MDM2 inhibitors. This approach ensures that the correct patients receive the appropriate treatment and during the course of the treatment the patient can be monitored for continued MDM2 inhibitor sensitivity.

In the development of MDM2 inhibitors, specific biomarkers will aid in understanding the mechanism of action upon administration. The mechanism of action may involve a complex cascade of regulatory mechanisms in the cell cycle and differential gene expression. This analysis is done at the preclinical stage of drug development in order to determine the particular sensitivity of cancer cells to the MDM2 inhibitor candidate and the activity of the candidate. Of particular interest in the pharmacodynamic investigation is the identification of specific markers of sensitivity and activity, such as the ones disclosed herein.

SUMMARY OF THE INVENTION

The invention relates to the analysis that a number of genes identified in Table 2 act as specific biomarkers in determining the sensitivity of cells to MDM2 inhibitors (henceforth "MDM2i"). The invention relates to the analysis that at least one of the biomarkers in Table 2 provides a "gene signature" for MDM2i that has increased accuracy and specificity in predicting which cancer cells are sensitive to MDM2i. The method analyzes the gene expression or protein level of at least one of the biomarkers in Table 2 in a cancer sample taken from a patient and compared to a baseline control predicts the sensitivity of the cancer sample to an MDM2i. The pattern of expression level changes may be indicative of a favorable response or an unfavorable one. In addition, the gene signature provided in Table 2 has increased predictive value because it also indicates that the p53 pathway is functional.

This is an unexpected result as many tumors contain a mutated p53 and a non-functional pathway which provides the tumor with a growth advantage. The invention is an example of "personalized medicine" wherein patients are treated based on a functional genomic signature that is specific to that individual.

The predictive value of at least one biomarker in Table 2 can also be used after treatment with an MDM2i to determine if the patient remains sensitive to the treatment. Once the MDM2i therapeutic has been administered, the biomarkers are used to monitor the continued sensitivity of the patient to MDM2i treatment. The disclosure also relates to the up or down regulation of the expression of the identified genes after MDM2i treatment. This is useful in determining that patients receive the correct course of treatment. The invention comprises a method of predicting and monitoring the sensitivity of a patient to MDM2i treatment. The method includes the step of administration of an MDM2i to the patient and measurement of biomarker gene expression on a biological sample obtained from the patient. The response of the patient is evaluated based on the detection of gene expression of at least one biomarker from Table 2. Detection and/or alteration in the level of expression of at least one biomarker compared to baseline is indicative of the sensitivity of the patient to the treatment. The pattern of expression level changes can be indicative of a favorable patient response or an unfavorable one.

DESCRIPTION OF THE DRAWINGS

FIG. 1A shows the in vitro potency of the MDM2i in disrupting p53-MDM2 interaction. FIG. 1B shows the in vitro potency of the MDM2i on the proliferation of cancer cells.

FIG. 2 shows the p53 status (mutant or wild type) and the sensitivity of the cancer cells to MDM2i(2). The X axis is the crossing point for sensitivity and the Y axis is the Amax value.

FIG. 3 are biomarkers showing the fold change in expression and the statistical significance of the overexpression value.

FIG. 5 is a graph demonstrating the increase in predictive value of the gene signature as opposed to a larger set of biomarkers.

FIG. 6 is a list of cell lines, each analyzed for the gene signature and the prediction of whether the cell line is sensitive or insensitive and the IC50 when treated with an MDM2i.

FIG. 7A-C shows the dose-dependent inhibition of tumor growth in the SJSA-1 xenograft model (predicted to be sensitive by the gene signature) following treatment with MDM2i(1), and the concomitant induction of p21 (CDKN1A) expression as a representative pharmacodynamic biomarker.

FIG. 9 is a model of tumor samples predicted to be sensitive using the gene signature in the OncExpress database and the Primary Tumor Bank.

FIG. 10 represents the Positive Predictive Values (PPV) achieved by the MDM2i(2) sensitivity predictive models, built from multiple combinations of biomarkers described in Table 2.

FIG. 11 represents the Specificities achieved by the MDM2i sensitivity predictive models, built from multiple combinations of biomarkers described in Table 2.

FIG. 12 represents the Sensitivities achieved by the MDM2i sensitivity predictive models, built from multiple combinations of biomarkers described in Table 2.

FIG. 13 represents the PPV achieved by the MDM2i sensitivity predictive models, built from multiple combinations of biomarkers described in Table 2, together with p53 mutation status.

FIG. 14 represents the Specificities achieved by the MDM2i sensitivity predictive models, built from multiple combinations of biomarkers described in Table 2, together with p53 mutation status.

FIG. 15 represents the Sensitivities achieved by the MDM2i sensitivity predictive models, built from multiple combinations of biomarkers described in Table 2, together with p53 mutation status.

DESCRIPTION OF THE INVENTION

Figure 4:
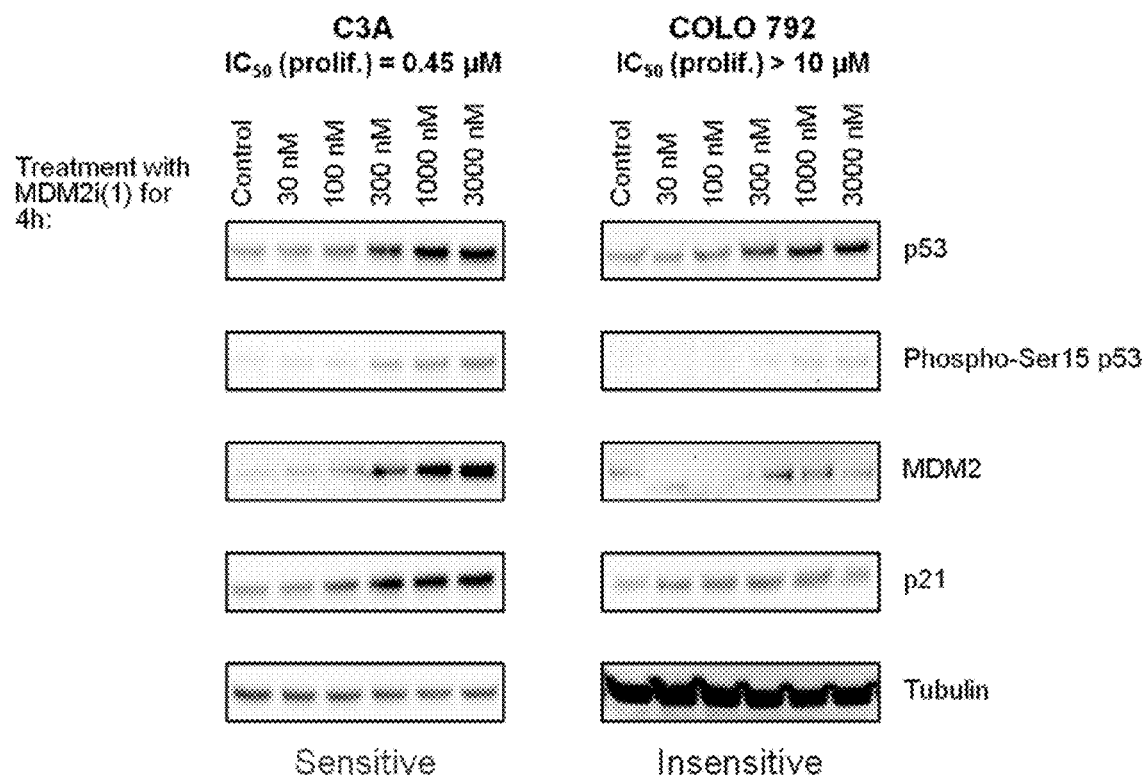
FIG. 4 is a Western blot of sensitive and insensitive representative cells treated with an MDM2i(1) for 4 hours at various concentrations and then probed for selected p53 target genes as pharmacodynamic biomarker representatives.

The aspects, features and embodiments of the present invention are summarized in the following items and can be used respectively alone or in combination:

1. A method of predicting the sensitivity of a cancer patient for treatment with a Human Double Minute 2 inhibitor (MDM2i), the method comprising: a) measuring differential gene expression of at least one biomarker selected from Table 2 in a cancer sample obtained from the patient; and b) comparing the differential gene expression of the at least one biomarker with gene expression of said biomarker in a control sample, wherein the increase or decrease in gene expression comparison indicates that the patient is sensitive to treatment with an MDM2i.

2. A method of treating a cancer patient comprising: a) measuring differential gene expression of at least one biomarker selected from Table 2 in a cancer sample obtained from the patient; b) comparing the differential gene expression of the at least one biomarker with gene expression of the biomarker in a control sample; c) determining sensitivity of the patient to an MDM2i; and d) administering to the patient an MDM2i.

3. A method of predicting the sensitivity of a cancer cell to a Human Double Minute 2 inhibitor (MDM2i), the method comprising: a) measuring differential gene expression of at least one biomarker selected from Table 2 in the cell; b) comparing the differential gene expression of the at least one biomarker selected from Table 2 with gene expression from a normal or control cell.

4. A method of determining the sensitivity of a cancer cell to a Human Double Minute 2 inhibitor (MDM2i), the method comprising: a) contacting a cancer cell with at least one MDM2i; b) measuring differential gene expression of at least one biomarker selected from Table 2 in the cell contacted with the MDM2i; c) comparing the differential gene expression of the at least one biomarker with gene expression of the biomarker from an untreated or placebo treated control cell; d) wherein there is an increase in the expression of at the least one biomarker when compared with the expression of the at least one biomarker from the untreated or placebo treated control cell.

5. The method of any one of items 1 to 3, wherein more than one biomarker is selected from Table 2.

6. The method of item 1 or 4, wherein at least two, at least three, at least four, at least five, at least six, at least seven, at least eight, at least nine, at least ten, at least eleven, at least twelve or all thirteen biomarkers are selected from Table 2.

7. The method of any one of items 1 to 5, wherein p53 is selected as a biomarker in addition to any biomarker selected from Table 2.

8. The method of any one of items 1 to 6, comprising the biomarkers MDM2, CDKN1A, ZMAT3, DDB2, FDXR, RPS27L, BAX, RRM2B, SESN1, CCNG1, XPC, TNFRSF10B and/or AEN.

9. The method of any one of items 1 to 7, wherein comparing the differential gene expression of the at least one biomarker with gene expression of a control sample indicates a functional p53 gene pathway.

10. The method of any one of items 1 to 8, wherein the cancer sample is selected from the group consisting of breast, lung, pancreas, ovary, central nervous system (CNS), endometrium, stomach, large intestine, colon, esophagus, bone, urinary tract, hematopoietic, lymphoid, liver, skin, melanoma, kidney, soft tissue sarcoma and pleura.

11. The method of any one of items 1 to 9, wherein a nucleic acid or protein of at least one biomarker is measured.

12. The method of any one of items 1, 2 or 5 to 11, wherein the expression of the at least one biomarker is increased in the cancer sample when compared to a control sample.

13. The method of any one of items 1 to 11, wherein the MDM2i is selected from Table 1.

14. The method of any one of items 1 to 12, wherein the MDM2i is a compound that binds to a p53 binding pocket of MDM2.

15. The method of any one of items 1 to 13, wherein the MDM2i is a compound that binds to substantially the same p53 binding pocket of MDM2 as Nutlin-3a or the MDM2i from the Table 1.

16. The method of any one of items 1 to 14, wherein the MDM2i is a compound that prevents the protein-protein interaction between p53 and MDM2.

17. The method of any one of items 1 to 15, wherein the MDM2i is a compound that inhibits cell proliferation by inducing the p53 pathway activity.

18. The method of any one of items 2 to 16 further comprising obtaining a biological sample from the patient prior to the administration of the MDM2i.

19. The method of any one of items 2 to 17, wherein the MDM2i is administered in a therapeutically effective amount.

20. The method of any one of items 3 to 11, or 13 to 19, wherein the gene expression of the at least one biomarker is increased in the cancer cell.

21. The method of any one of items 4 to 11, or 13 to 20, wherein the IC50 of the cancer cell contacted with at least one MDM2i is less than 1 µM 22. The method of any one of items 4 to 11, or 13 to 21, wherein the cell is contacted by the MDM2i at least at two different time points.

23. The method of any one of items 4 to 11, or 13 to 22, wherein the cell is contacted by two different MDM2i at step a).

24. The method of item 23, wherein the cell is contacted by the two different MDM2i at the same time.

25. The method of item 23, wherein the cell is contacted by two different MDM2i at different time points.

26. The method of any one of items 4 to 11, or 13 to 25, wherein the steps b) and c) are repeated at a time points selected from the group consisting of: 4 hours, 8 hours, 16 hours, 24 hours, 48 hours, 3 days, 1 week, 1 month and several months after administration of each dose of MDM2i.

27. A method of screening for MDM2i candidates the method comprising: a) contacting a cell with a MDM2i candidate; b) measuring gene expression of at least one biomarker selected from Table 2 in the cell contacted with the MDM2i candidate; and c) comparing the gene expression of the at least one biomarker selected from Table 2 from the cell contacted with the MDM2i candidate with gene expression of the at least one biomarker selected from Table 2 from a cell contacted with an MDM2i taken from Table 1 and the gene expression of at least one biomarker of an untreated or placebo treated cell.

28. The method of item 27, wherein the differential gene expression of the MDM2i candidate is compared with the differential gene expression of an MDM2i selected from Table 1.

29. The method of item 27 or 28, wherein the MDM2i candidate increases gene expression of at least one, at least two, at least three, at least four, at least five, at least six, at least seven, at least eight, at least nine, at least ten, at least eleven, at least twelve or all thirteen biomarkers from Table 2.

30. The method of any one of items 27 to 29, wherein the cell is a cancer cell selected from the group consisting of breast, lung, pancreas, ovary, central nervous system (CNS), endometrium, stomach, large intestine, colon, esophagus, bone, urinary tract, hematopoietic, lymphoid, liver, skin, melanoma, kidney, soft tissue sarcoma and pleura.

31. The method of any one of items 27 to 30, wherein the expression of nucleic acid or protein of at least one biomarker of Table 2 is measured.

32. The method of any one of items 27 to 31, comprising the biomarkers MDM2, CDKN1A, ZMAT3, DDB2, FDXR, RPS27L, BAX, RRM2B, SESN1, CCNG1, XPC, TNFRSF10B and AEN.

33. Composition comprising an MDM2i for use in treatment of cancer in a selected cancer patient population, wherein the cancer patient population is selected on the basis of showing an increased gene expression rate of at least one biomarker selected from Table 2 in a cancer cell sample obtained from said patients compared to a normal control cell sample.

34. The composition of item 33, wherein at least two, at least three, at least four, at least five, at least six, at least seven, at least eight, at least nine, at least ten, at least eleven, at least twelve or all thirteen biomarkers are selected from Table 2.

35. The composition of items 33 or 34, wherein p53 is selected as a biomarker in addition to any biomarker selected from Table 2.

36. The composition of any one of items 33 to 35, wherein the biomarker is MDM2, CDKN1A, ZMAT3, DDB2, FDXR, RPS27L, BAX, RRM2B, SESN1, CCNG1, XPC, TNFRSF10B and/or AEN.

37. The composition of any one of items 33 to 36, wherein the MDM2i is selected from Table 1.

38. The composition of any one of items 33 to 37, wherein the MDM2i is a compound that binds to a p53 binding pocket of MDM2.

39. The composition of any one of items 33 to 38, wherein the MDM2i is a compound that binds to substantially the same p53 binding pocket of MDM2 as Nutlin-3a or the MDM2i from the Table 1.

40. The composition of any one of items 33 to 39, wherein the MDM2i is a compound that prevents the protein-protein interaction between p53 and MDM2.

41. The composition of any one of items 33 to 40, wherein the MDM2i is a compound that inhibits cell proliferation by inducing the p53 pathway activity.

42. The composition of any one of items 33 to 41, wherein the cancer cell sample is selected from the group consisting of breast, lung, pancreas, ovary, central nervous system (CNS), endometrium, stomach, large intestine, colon, esophagus, bone, urinary tract, hematopoietic, lymphoid, liver, skin, melanoma, kidney, soft tissue sarcoma and pleura.

43. The composition of any one of items 33 to 42, wherein the patients are selected on the basis of an increased gene expression of the biomarkers MDM2, CDKN1A, ZMAT3, DDB2, FDXR, RPS27L, BAX, RRM2B, SESN1, CCNG1, XPC, TNFRSF10B and AEN.

44. A kit for predicting the sensitivity of a cancer patient for treatment with a Human Double Minute 2 inhibitor (MDM2i) comprising: i) means for detecting the expression of any one of the biomarkers from the table 2, preferably more than one, particularly at least two, at least three, at least four, at least five, at least six, at least seven, at least eight, at least nine, at least ten, at least eleven, at least twelve or all thirteen biomarkers selected from Table 2; and ii) instructions how to use said kit.

45. The kit of item 44, wherein the biomarkers are MDM2, CDKN1A, ZMAT3, DDB2, FDXR, RPS27L, BAX, RRM2B, SESN1, CCNG1, XPC, TNFRSF10B or/and AEN.

46. The kit of item 45 further comprising means for detecting the expression of p53.

47. Use of the kit according to item 45 or 46 for any of the methods of items 1 to 32.

Further aspects describe the invention:

In one aspect, a disclosed invention relates to methods of analyzing at least one of the biomarkers identified in Table 2 in a sample containing cancer cells wherein increased or decreased expression of at least one biomarker when compared to a baseline indicates if the cancer cell will be sensitive to MDM2i treatment. The pattern of expression level changes can be indicative of a favorable patient response or of an unfavorable one and patients can be selected or rejected based on the increased or decreased expression of at least one biomarker from Table 2. Alternatively, all of the biomarkers in Table 2 can be assayed for as a single set.

After treatment with an MDM2i, the invention relates to methods of analyzing at least one of the biomarkers identified in Table 2 in a sample containing cancer cells wherein increased or decreased expression of the biomarker when compared to a baseline control after MDM2i treatment indicates that the patient is still sensitive to MDM2i treatment. Detection and/or alteration in the level of expression of at least one biomarker compared to a baseline is indicative of the MDM2i sensitivity, and this correlates with a response of the patient to the treatment. Alternatively, all of the biomarkers in Table 2 can be assayed for as a single set. The pattern of expression level changes can be indicative of a favorable patient response or of an unfavorable one.

Accordingly, the invention provides for a method of predicting the sensitivity of a cancer patient for treatment with a Human Double Minute 2 inhibitor (MDM2i), the method comprising: a) measuring differential gene expression of at least one biomarker selected from Table 2 in a cancer sample obtained from the patient; and b) comparing the differential gene expression of the at least one biomarker with gene expression of a control sample, wherein the increase or decrease in gene expression comparison indicates that the patient is sensitive to treatment with an MDM2i.

The method wherein more than one biomarker is selected from Table 2.

The method comprising the biomarkers MDM2, CDKN1A, ZMAT3, DDB2, FDXR, RPS27L, BAX, RRM2B, SESN1, CCNG1, XPC, TNFRSF10B and AEN.

The method wherein comparing the differential gene expression of the at least one biomarker with gene expression of a control sample indicates a functional p53 gene pathway.

The method wherein the cancer sample is selected from the group consisting of: breast, lung, pancreas, ovary, central nervous system (CNS), endometrium, stomach, large intestine, colon, esophagus, bone, urinary tract, hematopoietic, lymphoid, liver, skin, melanoma, kidney, soft tissue sarcoma and pleura.

The method wherein a nucleic acid or protein of at least one biomarker is measured.

The method wherein the gene expression of the at least one biomarker is increased.

The method wherein the MDM2i is selected from Table 1.

The method wherein the MDM2i is administered in a therapeutically effective amount.

A method of treating a cancer patient comprising: a) measuring differential gene expression of at least one biomarker selected from Table 2 in a cancer sample obtained from the patient; b) comparing the differential gene expression of the at least one biomarker with gene expression of a control sample; c) determining sensitivity of the patient to an MDM2i; and d) administering to the patient an MDM2i.

The method wherein more than one biomarker is selected from Table 2.

The method of comprising the biomarkers MDM2, CDKN1A, ZMAT3, DDB2, FDXR, RPS27L, BAX, RRM2B, SESN1, CCNG1, XPC, TNFRSF10B and AEN.

The method wherein the at least one biomarker indicates a functional p53 gene pathway.

The method further comprising obtaining a biological sample from the patient prior to the administration of the MDM2i.

The method wherein the cancer sample is selected from the group consisting of: breast, lung, pancreas, ovary, central nervous system (CNS), endometrium, stomach, large intestine, colon, esophagus, bone, urinary tract, hematopoietic, lymphoid, liver, skin, melanoma, kidney, soft tissue sarcoma and pleura.

The method wherein the MDM2i is selected from Table 1.

The method wherein the MDM2i is administered in a therapeutically effective amount.

A method of predicting the sensitivity of a cancer cell to a Human Double Minute 2 inhibitor (MDM2i), the method comprising: a) measuring differential gene expression of at least one biomarker selected from Table 2 in the cell b) comparing the differential gene expression of the at least on biomarker selected from Table 2 with gene expression from a normal or control cell.

The method wherein the MDM2i is selected from Table 1.

The method wherein more than one biomarker is selected from Table 2.

The method comprising the biomarkers MDM2, CDKN1A, ZMAT3, DDB2, FDXR, RPS27L, BAX, RRM2B, SESN1, CCNG1, XPC, TNFRSF10B and AEN.

The method wherein comparing the differential gene expression of the at least one biomarker with gene expression of a control sample indicates a functional p53 gene pathway.

The method wherein the cancer sample is selected from the group consisting of: breast, lung, pancreas, ovary, central nervous system (CNS), endometrium, stomach, large intestine, colon, esophagus, bone, urinary tract, hematopoietic, lymphoid, liver, skin, melanoma, kidney, soft tissue sarcoma and pleura.

The method wherein a nucleic acid or protein of at least one biomarker is measured.

The method wherein the gene expression of the at least one biomarker is increased.

The method wherein the MDM2i is selected from Table 1.

The method wherein the MDM2i is administered in a therapeutically effective amount.

A method of assaying for the sensitivity of a cancer cell to a Human Double Minute 2 inhibitor (MDM2i), the method comprising: a) contacting a cancer cell with at least one MDM2i; b) measuring differential gene expression of at least one biomarker selected from Table 2 in the cancer cell contacted with the MDM2i; c) comparing the differential gene expression with gene expression from an untreated or placebo treated control cell; d) wherein the IC50 of the cancer cell contacted with at least one MDM2i is less than 3 µM.

The method wherein the cancer cell is contacted by the MDM2i at least two different time points.

The method wherein the cancer cell is contacted by two different MDM2i at step a).

The method wherein the cancer cell is contacted by the two different MDM2i at the same time.

The method wherein the cancer cell is contacted by two different MDM2i at different time points.

The method wherein the cancer cell is selected from the group consisting of breast, lung, pancreas, ovary, central nervous system (CNS), endometrium, stomach, large intestine, colon, esophagus, bone, urinary tract, hematopoietic, lymphoid, liver, skin, melanoma, kidney, soft tissue sarcoma and pleura.

The method wherein a nucleic acid or protein of at least one biomarker is measured.

The method wherein the gene expression of the at least one biomarker is increased.

The method comprising the biomarkers: MDM2, CDKN1A, ZMAT3, DDB2, FDXR, RPS27L, BAX, RRM2B, SESN1, CCNG1, XPC, TNFRSF10B and AEN.

The method wherein the steps b) and c) are repeated at time points of: 4 hours, 8 hours, 16 hours, 24 hours, 48 hours, 3 days, 1 week, 1 month and 2 months after contact with an MDM2i.

A method of screening for MDM2i candidates the method comprising: a) contacting a cell with a MDM2i candidate; b) measuring differential gene expression of at least one biomarker selected from Table 2 in the cell contacted with the MDM2i candidate; and c) comparing the differential gene expression of at least one biomarker selected from Table 2 from the cell contacted with the MDM2i candidate with differential gene expression of at least one biomarker selected from Table 2 from a cell contacted with an MDM2i taken from Table 1 and the differential gene expression of at least one biomarker of an untreated or placebo treated cell.

The method wherein the differential gene expression of the MDM2i candidate is compared with the differential gene expression of an MDM2i selected from Table 1. The method wherein the MDM2i candidate increases gene expression of at least one biomarker of Table 2.

The method wherein the cancer cell is selected from the group consisting of breast, lung, pancreas, ovary, central nervous system (CNS), endometrium, stomach, large intestine, colon, esophagus, bone, urinary tract, hematopoietic, lymphoid, liver, skin, melanoma, kidney, soft tissue sarcoma and pleura.

The method wherein the expression of nucleic acid or protein of at least one biomarker of Table 2 is measured.

The method comprising the biomarkers MDM2, CDKN1A, ZMAT3, DDB2, FDXR, RPS27L, BAX, RRM2B, SESN1, CCNG1, XPC, TNFRSF10B and AEN.

Composition comprising an MDM2i for use in treatment of cancer in a selected cancer patient population, wherein the cancer patient population is selected on the basis of showing an increased gene expression rate of at least one biomarker selected from Table 2 in a cancer cell sample obtained from said patients compared to a normal control cell sample. The composition wherein the cancer sample is selected from the group consisting of breast, lung, pancreas, ovary, central nervous system (CNS), endometrium, stomach, large intestine, colon, esophagus, bone, urinary tract, hematopoietic, lymphoid, liver, skin, melanoma, kidney, soft tissue sarcoma and pleura.

The composition wherein the patients are selected on the basis of an increased gene expression of the biomarkers MDM2, CDKN1A, ZMAT3, DDB2, FDXR, RPS27L, BAX, RRM2B, SESN1, CCNG1, XPC, TNFRSF10B and AEN.

A kit for predicting the sensitivity of a cancer patient for treatment with a Human Double Minute 2 inhibitor (MDM2i) comprising: i) means for detecting the expression of the biomarkers MDM2, CDKN1A, ZMAT3, DDB2, FDXR, RPS27L, BAX, RRM2B, SESN1, CCNG1, XPC, TNFRSF10B and AEN; and ii) instructions how to use said kit.

DEFINITIONS

As used in the specification and claims, the singular form "a", "an" and "the" include plural references unless the context clearly dictates otherwise. For example, the term "a cell" includes a plurality of cells, including mixtures thereof.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about." It also is to be understood, although not always explicitly stated, that the reagents described herein are merely exemplary and that equivalents of such are known in the art.

The terms "marker" or "biomarker" are used interchangeably herein. A biomarker is a nucleic acid or polypeptide and the presence, absence or differential expression of the nucleic acid or polypeptide is used to determine sensitivity to any MDM2i. For example, CDKN1A is a biomarker and the mRNA expression of CDKN1A in a cancer cell is increased when compared to CDKN1A expression in normal (non-cancerous) tissue or control tissue.

"MDM2" refers to an E3 ubiquitin-protein ligase that mediates the ubiquitination of p53, permits the nuclear export of p53 and triggers p53 degradation. Unless specifically stated otherwise, MDM2 as used herein, refers to human MDM2-accession numbers NM 002392/NP_002383 (SEQ ID NO. 1/SEQ ID NO. 2).

A cell is "sensitive" or displays "sensitivity" for inhibition with an MDM2i when at least one of the biomarkers disclosed in Table 2 is differentially expressed. Alternatively, a cell is "sensitive" for inhibition with an MDM2i when all of the biomarkers disclosed in Table 2 as a set are differentially expressed.

A "control cell" or "normal cell" refers to non-cancerous tissue or cell.

A "control tissue" or "normal tissue" refers to non-cancerous tissue or cell.

A "control sample" or "normal sample" refers to non-cancerous tissue or cell.

The terms "nucleic acid" and "polynucleotide" are used interchangeably and refer to a polymeric form of nucleotides of any length, either deoxyribonucleotides or ribonucleotides or analogs thereof. Polynucleotides can have any three-dimensional structure and may perform any function. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide can comprise modified nucleotides, such as methylated nucleotides and nucleotide analogs. If present, modifications to the nucleotide structure can be imparted before or after assembly of the polymer. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A "gene" refers to a polynucleotide containing at least one open reading frame (ORF) that is capable of encoding a particular polypeptide or protein after being transcribed and translated. A polynucleotide sequence can be used to identify larger fragments or full-length coding sequences of the gene with which they are associated. Methods of isolating larger fragment sequences are known to those of skill in the art.

"Gene expression" or alternatively a "gene product" refers to the nucleic acids or amino acids (e.g., peptide or polypeptide) generated when a gene is transcribed and translated.

The term "polypeptide" is used interchangeably with the term "protein" and in its broadest sense refers to a compound of two or more subunit amino acids, amino acid analogs, or peptidomimetics. The subunits can be linked by peptide bonds. In another embodiment, the subunit may be linked by other bonds, e.g., ester, ether, etc.

As used herein the term "amino acid" refers to either natural and/or unnatural or synthetic amino acids, and both the D and L optical isomers, amino acid analogs, and peptidomimetics. A peptide of three or more amino acids is commonly called an oligopeptide if the peptide chain is short. If the peptide chain is long, the peptide is commonly called a polypeptide or a protein.

The term "isolated" means separated from constituents, cellular and otherwise, in which the polynucleotide, peptide, polypeptide, protein, antibody or fragment(s) thereof, are normally associated with in nature. For example, an isolated polynucleotide is separated from the 3' and 5' contiguous nucleotides with which it is normally associated within its native or natural environment, e.g., on the chromosome. As is apparent to those of skill in the art, a non-naturally occurring polynucleotide, peptide, polypeptide, protein, antibody, or fragment(s) thereof, does not require "isolation" to distinguish it from its naturally occurring counterpart. In addition, a "concentrated," "separated" or "diluted" polynucleotide, peptide, polypeptide, protein, antibody or fragment(s) thereof, is distinguishable from its naturally occurring counterpart in that the concentration or number of molecules per volume is greater in a "concentrated" version or less than in a "separated" version than that of its naturally occurring counterpart. A polynucleotide, peptide, polypeptide, protein, antibody, or fragment(s) thereof, which differs from the naturally occurring counterpart in its primary sequence or, for example, by its glycosylation pattern, need not be present in its isolated form since it is distinguishable from its naturally occurring counterpart by its primary sequence or, alternatively, by another characteristic such as glycosylation pattern. Thus, a non-naturally occurring polynucleotide is provided as a separate embodiment from the isolated naturally occurring polynucleotide. A protein produced in a bacterial cell is provided as a separate embodiment from the naturally occurring protein isolated from a eukaryotic cell in which it is produced in nature.

A "probe" when used in the context of polynucleotide manipulation refers to an oligonucleotide that is provided as a reagent to detect a target potentially present in a sample of interest by hybridizing with the target. Usually, a probe will comprise a label or a means by which a label can be attached, either before or subsequent to the hybridization reaction. Suitable labels include, but are not limited to radioisotopes, fluorochromes, chemiluminescent compounds, dyes, and proteins, including enzymes.

A "primer" is a short polynucleotide, generally with a free 3'-OH group that binds to a target or "template" potentially present in a sample of interest by hybridizing with the target, and thereafter promoting polymerization of a polynucleotide complementary to the target. A "polymerase chain reaction" ("PCR") is a reaction in which replicate copies are made of a target polynucleotide using a "pair of primers" or a "set of primers" consisting of an "upstream" and a "downstream" primer, and a catalyst of polymerization, such as a DNA polymerase, and typically a thermally-stable polymerase enzyme. Methods for PCR are well known in the art, and taught, for example in PCR: A Practical Approach, M. MacPherson et al., IRL Press at Oxford University Press (1991). All processes of producing replicate copies of a polynucleotide, such as PCR or gene cloning, are collectively referred to herein as "replication." A primer can also be used as a probe in hybridization reactions, such as Southern or Northern blot analyses (Sambrook et al., Molecular Cloning: A Laboratory Manual, 2nd edition (1989)).

As used herein, "expression" refers to the process by which DNA is transcribed into mRNA and/or the process by which the transcribed mRNA is subsequently translated into peptides, polypeptides or proteins. If the polynucleotide is derived from genomic DNA, expression may include splicing of the mRNA in a eukaryotic cell.

"Differentially expressed" as applied to a gene, refers to the differential production of the mRNA transcribed and/or translated from the gene or the protein product encoded by the gene. A differentially expressed gene may be overexpressed or underexpressed as compared to the expression level of a normal or control cell. However, as used herein, overexpression is an increase in gene expression and generally is at least 1.25 fold or, alternatively, at least 1.5 fold or, alternatively, at least 2 fold, or alternatively, at least 3 fold or alternatively, at least 4 fold expression over that detected in a normal or control counterpart cell or tissue. As used herein, underexpression, is a reduction of gene expression and generally is at least 1.25 fold, or alternatively, at least 1.5 fold, or alternatively, at least 2 fold or alternatively, at least 3 fold or alternatively, at least 4 fold expression under that detected in a normal or control counterpart cell or tissue. The term "differentially expressed" also refers to where expression in a cancer cell or cancerous tissue is detected but expression in a control cell or normal tissue (e.g. non-cancerous cell or tissue) is undetectable.

A high expression level of the gene may occur because of over expression of the gene or an increase in gene copy number. The gene may also be translated into increased protein levels because of deregulation or absence of a negative regulator.

A "gene expression profile" refers to a pattern of expression of at least one biomarker that recurs in multiple samples and reflects a property shared by those samples, such as tissue type, response to a particular treatment, or activation of a particular biological process or pathway in the cells. Furthermore, a gene expression profile differentiates between samples that share that common property and those that do not with better accuracy than would likely be achieved by assigning the samples to the two groups at random. A gene expression profile may be used to predict whether samples of unknown status share that common property or not. Some variation between the levels of at least one biomarker and the typical profile is to be expected, but the overall similarity of the expression levels to the typical profile is such that it is statistically unlikely that the similarity would be observed by chance in samples not sharing the common property that the expression profile reflects.

The term "cDNA" refers to complementary DNA, i.e. mRNA molecules present in a cell or organism made into cDNA with an enzyme such as reverse transcriptase. A "cDNA library" is a collection of all of the mRNA molecules present in a cell or organism, all turned into cDNA molecules with the enzyme reverse transcriptase, then inserted into "vectors" (other DNA molecules that can continue to replicate after addition of foreign DNA). Exemplary vectors for libraries include bacteriophage (also known as "phage"), viruses that infect bacteria, for example, lambda phage. The library can then be probed for the specific cDNA (and thus mRNA) of interest.

As used herein, "solid phase support" or "solid support", used interchangeably, is not limited to a specific type of support. Rather a large number of supports are available and are known to one of ordinary skill in the art. Solid phase supports include silica gels, resins, derivatized plastic films, glass beads, plastic beads, alumina gels, microarrays, and chips. As used herein, "solid support" also includes synthetic antigen-presenting matrices, cells, and liposomes. A suitable solid phase support may be selected on the basis of desired end use and suitability for various protocols. For example, for peptide synthesis, solid phase support may refer to resins such as polystyrene (e.g., PAM-resin obtained from Bachem Inc., Peninsula Laboratories), polyHIPE(R)™ resin (obtained from Aminotech, Canada), polyamide resin (obtained from Peninsula Laboratories), polystyrene resin grafted with polyethylene glycol (TentaGelR™, Rapp Polymere, Tubingen, Germany), or polydimethylacrylamide resin (obtained from Milligen/Biosearch, California).

A polynucleotide also can be attached to a solid support for use in high throughput screening assays. PCT WO 97/10365, for example, discloses the construction of high density oligonucleotide chips. See also, U.S. Pat. Nos. 5,405,783; 5,412, 087 and 5,445,934. Using this method, the probes are synthesized on a derivatized glass surface to form chip arrays. Photoprotected nucleoside phosphoramidites are coupled to the glass surface, selectively deprotected by photolysis through a photolithographic mask and reacted with a second protected nucleoside phosphoramidite. The coupling/deprotection process is repeated until the desired probe is complete.

As an example, transcriptional activity can be assessed by measuring levels of messenger RNA using a gene chip such as the Affymetrix® HG-U133-Plus-2 GeneChips. High-throughput, real-time quantitation of RNA of a large number of genes of interest thus becomes possible in a reproducible system.

The terms "stringent hybridization conditions" refers to conditions under which a nucleic acid probe will specifically hybridize to its target subsequence, and to no other sequences. The conditions determining the stringency of hybridization include: temperature, ionic strength, and the concentration of denaturing agents such as formamide. Varying one of these factors may influence another factor and one of skill in the art will appreciate changes in the conditions to maintain the desired level of stringency. An example of a highly stringent hybridization is: 0.015M sodium chloride, 0.0015M sodium citrate at 65-68° C. or 0.015M sodium chloride, 0.0015M sodium citrate, and 50% formamide at 42° C. (see Sambrook, supra). An example of a "moderately stringent" hybridization is the conditions of: 0.015M sodium chloride, 0.0015M sodium citrate at 50-65° C. or 0.015M sodium chloride, 0.0015M sodium citrate, and 20% formamide at 37-50° C. The moderately stringent conditions are used when a moderate amount of nucleic acid mismatch is desired. One of skill in the art will appreciate that washing is part of the hybridization conditions. For example, washing conditions can include 02.x-0.1x SSC/0.1% SDS and temperatures from 42-68° C., wherein increasing temperature increases the stringency of the wash conditions.

When hybridization occurs in an antiparallel configuration between two single-stranded polynucleotides, the reaction is called "annealing" and those polynucleotides are described as "complementary." A double-stranded polynucleotide can be "complementary" or "homologous" to another polynucleotide, if hybridization can occur between one of the strands of the first polynucleotide and the second. "Complementarity" or "homology" (the degree that one polynucleotide is complementary with another) is quantifiable in terms of the proportion of bases in opposing strands that are expected to form hydrogen bonding with each other, according to generally accepted base-pairing rules.

A polynucleotide or polynucleotide region (or a polypeptide or polypeptide region) has a certain percentage (for example, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Current Protocols in Molecular Biology, Ausubel et al., eds., (1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant.

The term "cell proliferative disorders" shall include dysregulation of normal physiological function characterized by abnormal cell growth and/or division or loss of function. Examples of "cell proliferative disorders" include but are not limited to hyperplasia, neoplasia, metaplasia, and various autoimmune disorders, e.g., those characterized by the dysregulation of T cell apoptosis.

As used herein, the terms "neoplastic cells," "neoplastic disease," "neoplasia," "tumor," "tumor cells," "cancer," and "cancer cells," (used interchangeably) refer to cells which exhibit relatively autonomous growth, so that they exhibit an aberrant growth phenotype characterized by a significant loss of control of cell proliferation (i.e., de-regulated cell division). Neoplastic cells can be malignant or benign. A metastatic cell or tissue means that the cell can invade and destroy neighboring body structures.

The term "cancer" refers to cancer diseases including, for example, breast, lung, pancreas, ovary, central nervous system (CNS), endometrium, stomach, large intestine, colon, esophagus, bone, urinary tract, hematopoietic, lymphoid, liver, skin, melanoma, kidney, soft tissue sarcoma and pleura.

The term "PBMC" refers to peripheral blood mononuclear cells and includes "PBL"—peripheral blood lymphocytes.

"Suppressing" tumor growth indicates a reduction in tumor cell growth when contacted with an MDM2i compared to tumor growth without contact with an MDM2i compound. Tumor cell growth can be assessed by any means known in the art, including, but not limited to, measuring tumor size, determining whether tumor cells are proliferating using a 3H-thymidine incorporation assay, measuring glucose uptake by FDG-PET (fluorodeoxyglucose positron emission tomography) imaging, or counting tumor cells. "Suppressing" tumor cell growth means any or all of the following states: slowing, delaying and stopping tumor growth, as well as tumor shrinkage.

A "composition" is a combination of active agent and another carrier, e.g., compound or composition, inert (for example, a detectable agent or label) or active, such as an adjuvant, diluent, binder, stabilizer, buffers, salts, lipophilic solvents, preservative, adjuvant or the like. Carriers also include pharmaceutical excipients and additives, for example; proteins, peptides, amino acids, lipids, and carbohydrates (e.g., sugars, including monosaccharides and oligosaccharides; derivatized sugars such as alditols, aldonic acids, esterified sugars and the like; and polysaccharides or sugar polymers), which can be present singly or in combination, comprising alone or in combination 1-99.99% by weight or volume. Carbohydrate excipients include, for example; monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like.

The term "carrier" further includes a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Additional carriers include polymeric excipients/additives such as polyvinylpyrrolidones, ficolls (a polymeric sugar), dextrates (e.g., cyclodextrins, such as 2-hydroxypropyl-quadrature-cyclodextrin), polyethylene glycols, flavoring agents, antimicrobial agents, sweeteners, antioxidants, antistatic agents, surfactants (e.g., polysorbates such as TWEEN 20™ and TWEEN 80™), lipids (e.g., phospholipids, fatty acids), steroids (e.g., cholesterol), and chelating agents (e.g., EDTA).

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives and any of the above noted carriers with the additional provisio that they be acceptable for use in vivo. For examples of carriers, stabilizers and adjuvants, see Remington's Pharmaceutical Science., 15th Ed. (Mack Publ. Co., Easton (1975) and in the Physician's Desk Reference, 52nd ed., Medical Economics, Montvale, N.J. (1998).

An "effective amount" is an amount sufficient to effect beneficial or desired results. An effective amount can be administered in one or more administrations, applications or dosages.

A "subject," "individual" or "patient" is used interchangeably herein, which refers to a vertebrate, preferably a mammal, more preferably a human. Mammals include, but are not limited to, mice, simians, humans, farm animals, sport animals, and pets.

An "inhibitor" of MDM2 as used herein reduces the association of p53 and MDM2. This inhibition may include, for example, reducing the association of p53 and MDM2 before they are bound together, or reducing the association of p53 and MDM2 after they are bound together, thus freeing both molecules.

A number of genes have now been identified as biomarkers for MDM2i. The decrease or increase of gene expression of one or more of the biomarkers identified herein and in Table 2 can be used to determine patient sensitivity to any MDM2i, for example, the increase or overexpression of a biomarker indicates that a cancer patient is sensitive to and would favorably respond to administration of an MDM2i. As another example, after treatment with a MDM2i, a patient sample can be obtained and the sample assayed for sensitivity to discover if the patient is still sensitive to the MDM2i treatment. Alternatively, all of the biomarkers in Table 2 can be assayed for as a single set.

MDM2 inhibitors (MDM2i) are compounds which are inhibitors of the p53-MDM2 association, and are useful in conjunction with the methods or uses of the invention. MDM2i are useful in pharmaceutical compositions for human or veterinary use where inhibition of the p53-MDM2 association is indicated, e.g., in the treatment of tumors and/or cancerous cell growth. In particular, such compounds are useful in the treatment of human cancer, since the progression of these cancers may be at least partially dependent upon overriding the "gatekeeper" function of p53, for example the overexpression of MDM2. MDM2i compounds are useful in treating, for example, carcinomas (e.g., breast, lung, pancreas, ovary, central nervous system (CNS), endometrium, stomach, large intestine, colon, esophagus, bone, urinary tract, hematopoietic, lymphoid, liver, skin, melanoma, kidney, soft tissue sarcoma and pleura A listing of exemplary MDM2i compounds is found in Table 1 (see WO 2011076786). Other MDM2i that bind to a p53 binding pocket of MDM2, particularly to substantially the same p53 binding pocket of MDM2 as Nutlin-3a or substantially where the exemplary MDM2i from the Table 1 binds, can also be applied in the methods or uses of the invention. MDM2i used according to present embodiments can be structurally related to the one described in Table 1 (i.e. MDM2i(1) and MDM2i (2)) or to Nutlin 3a, such as, for example, substituted isoquinolinones, or quinazolinones (The methods included herein can also be used with other compounds such as the spiro-oxindoles, imidazolyl indole and cis-imidazoline (see Shangary et al., Mol. Cancer Ther. 2008 7(6): 1533-1542: Furet et al., Bio Org. Med. Chem. Let. 2012 22:3498-3502 and Carol et al., Pediatr. Blood Cancer 2012 pages 1-9, published online Jul. 2, 2012, prior to inclusion into journal). MDM2i as used herein prevents the protein-protein interaction between p53 and MDM2 or inhibits cell proliferation by inducing the p53 pathway activity.

TABLE 1

MDM2i compounds

MDM2i(1)

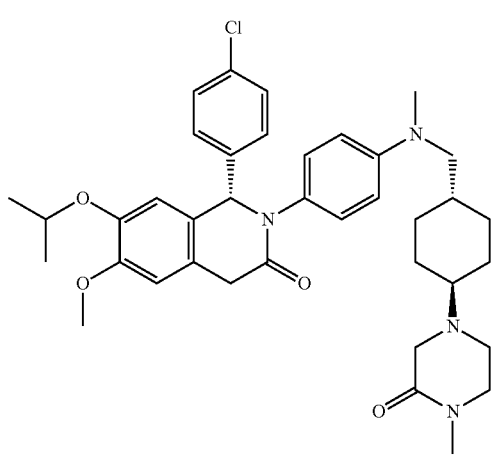 [SMILES: COc1cc2c(cc1OC(C)C)[C@H](c1ccc(Cl)cc1)N(c1ccc(N(C)C[C@H]3CC[C@H](N4CCN(C)C(=O)C4)CC3)cc1)C(=O)C2]

MDM2i(2)

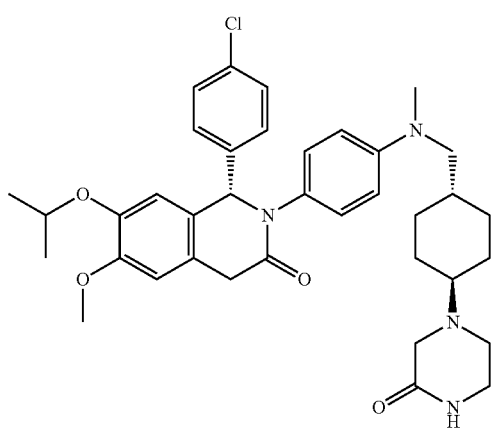 [SMILES: COc1cc2c(cc1OC(C)C)[C@H](c1ccc(Cl)cc1)N(c1ccc(N(C)C[C@H]3CC[C@H](N4CCNC(=O)C4)CC3)cc1)C(=O)C2]

Measurement of Gene Expression

Detection of gene expression can be by any appropriate method, including for example, detecting the quantity of mRNA transcribed from the gene or the quantity of cDNA produced from the reverse transcription of the mRNA transcribed from the gene or the quantity of the polypeptide or protein encoded by the gene. These methods can be performed on a sample by sample basis or modified for high throughput analysis. For example, using Affymetrix™ U133 microarray chips.

In one aspect, gene expression is detected and quantitated by hybridization to a probe that specifically hybridizes to the appropriate probe for that biomarker. The probes also can be attached to a solid support for use in high throughput screening assays using methods known in the art. WO 97/10365 and U.S. Pat. Nos. 5,405,783, 5,412,087 and 5,445,934, for example, disclose the construction of high density oligonucleotide chips which can contain one or more of the sequences disclosed herein. Using the methods disclosed in U.S. Pat. Nos. 5,405,783, 5,412,087 and 5,445,934, the probes of this invention are synthesized on a derivatized glass surface. Photoprotected nucleoside phosphoramidites are coupled to the glass surface, selectively deprotected by photolysis through a photolithographic mask, and reacted with a second protected nucleoside phosphoramidite. The coupling/deprotection process is repeated until the desired probe is complete.

In one aspect, the expression level of a gene is determined through exposure of a nucleic acid sample to the probe-modified chip. Extracted nucleic acid is labeled, for example, with a fluorescent tag, preferably during an amplification step. Hybridization of the labeled sample is performed at an appropriate stringency level. The degree of probe-nucleic acid hybridization is quantitatively measured using a detection device. See U.S. Pat. Nos. 5,578,832 and 5,631,734.

Alternatively any one of gene copy number, transcription, or translation can be determined using known techniques. For example, an amplification method such as PCR may be useful. General procedures for PCR are taught in MacPherson et al., PCR: A Practical Approach, (IRL Press at Oxford University Press (1991)). However, PCR conditions used for each application reaction are empirically determined. A number of parameters influence the success of a reaction. Among them are annealing temperature and time, extension time, Mg 2+ and/or ATP concentration, pH, and the relative concentration of primers, templates, and deoxyribonucleotides. After amplification, the resulting DNA fragments can be detected by agarose gel electrophoresis followed by visualization with ethidium bromide staining and ultraviolet illumination.

In one embodiment, the hybridized nucleic acids are detected by detecting one or more labels attached to the sample nucleic acids. The labels can be incorporated by any of a number of means well known to those of skill in the art. However, in one aspect, the label is simultaneously incorporated during the amplification step in the preparation of the sample nucleic acid. Thus, for example, polymerase chain reaction (PCR) with labeled primers or labeled nucleotides will provide a labeled amplification product. In a separate embodiment, transcription amplification, as described above, using a labeled nucleotide (e.g. fluorescein-labeled UTP and/or CTP) incorporates a label in to the transcribed nucleic acids.

Alternatively, a label may be added directly to the original nucleic acid sample (e.g., mRNA, polyA, mRNA, cDNA, etc.) or to the amplification product after the amplification is completed. Means of attaching labels to nucleic acids are well known to those of skill in the art and include, for example nick translation or end-labeling (e.g. with a labeled RNA) by kinasing of the nucleic acid and subsequent attachment (ligation) of a nucleic acid linker joining the sample nucleic acid to a label (e.g., a fluorophore).

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., 3H, 125I, 35S, 14C, or 32P) enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Detection of labels is well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label.

The detectable label may be added to the target (sample) nucleic acid(s) prior to, or after the hybridization, such as described in WO 97/10365. These detectable labels are directly attached to or incorporated into the target (sample) nucleic acid prior to hybridization. In contrast, "indirect labels" are joined to the hybrid duplex after hybridization. Generally, the indirect label is attached to a binding moiety that has been attached to the target nucleic acid prior to the hybridization. For example, the target nucleic acid may be biotinylated before the hybridization. After hybridization, an avidin-conjugated fluorophore will bind the biotin bearing hybrid duplexes providing a label that is easily detected. For a detailed review of methods of labeling nucleic acids and detecting labeled hybridized nucleic acids see Laboratory Techniques in Biochemistry and Molecular Biology, Vol. 24: Hybridization with Nucleic Acid Probes, P. Tijssen, ed. Elsevier, N.Y. (1993).

Detection of Polypeptides

Expression level of the biomarker can also be determined by examining protein expression or the protein product at least one of the biomarkers listed in Table 2. Determining the protein level involves measuring the amount of any immunospecific binding that occurs between an antibody that selectively recognizes and binds to the polypeptide of the biomarker in a sample obtained from a patient and comparing this to the amount of immunospecific binding of at least one biomarker in a control sample. The amount of protein expression of the biomarker can be increased or reduced when compared with control expression. Alternatively, all of the biomarkers in Table 2 can be assayed for as a single set.

A variety of techniques are available in the art for protein analysis. They include but are not limited to radioimmunoassays, ELISA (enzyme linked immunosorbent assays), "sandwich" immunoassays, immunoradiometric assays, in situ immunoassays (using e.g., colloidal gold, enzyme or radioisotope labels), western blot analysis, immunoprecipitation assays, immunofluorescent assays, flow cytometry, immunohistochemistry, confocal microscopy, enzymatic assays, surface plasmon resonance and PAGE-SDS.

Assaying for Biomarkers and MDM2i Treatment

Once a patient has been predicted to be sensitive to an MDM2i, administration of any MDM2i to a patient can be effected in one dose, continuously or intermittently throughout the course of treatment. Methods of determining the most effective means and dosage of administration are well known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents may be empirically adjusted.

At least one of the biomarkers provided in Table 2 can be assayed for after MDM2i administration in order to determine if the patient remains sensitive to the MDM2i treatment. In addition, at least one biomarker can be assayed for in multiple time points after a single MDM2i administration. For example, an initial bolus of an MDM2i is administered, at least one biomarker from Table 2 is assayed for at 1 hour, 2 hours, 3 hours, 4 hours, 8 hours, 16 hours, 24 hours, 48 hours, 3 days, 1 week or 1 month or several months after the first treatment. Alternatively, all of the biomarkers in Table 2 can be assayed for as a single set.

The at least one biomarker in Table 2 can be assayed for after each MDM2i administration, so if there are multiple MDM2i administrations, then at least one biomarker can be assayed for after each administration to determine continued patient sensitivity. The patient could undergo multiple MDM2i administrations and the biomarkers then assayed at different time points. For example, a course of treatment can require administration of an initial dose of MDM2i, a second dose a specified time period later, and still a third dose hours after the second dose. At least one biomarker of Table 2 could be assayed for at 1 hour, 2 hours, 3 hours, 4 hours, 8 hours, 16 hours, 24 hours, 48 hours, 3 days, 1 week or 1 month or several months after administration of each dose of MDM2i. Alternatively, all of the biomarkers in Table 2 can be assayed for as a single set.

It is also within the scope of the invention that different biomarkers are assayed for at different time points. Without being bound to any one theory, due to mechanism of action of the MDM2i or of the biomarker, the response to the MDM2i is delayed and at least one biomarker from Table 2 is assayed for at any time after administration to determine if the patient remains sensitive to MDM2i administration. An assay for at least one biomarker in Table 2 after each administration of MDM2i will provide guidance as to the means, dosage and course of treatment. Alternatively, all of the biomarkers in Table 2 can be assayed for as a single set.

Finally, there is administration of different MDM2 is and followed by assaying for at least one biomarker in Table 2. In this embodiment, more than one MDM2i is chosen and administered to the patient. At least one biomarker from Table 2 can then be assayed for after administration of each different MDM2i. This assay can also be done at multiple time points after administration of the different MDM2i. For example, a first MDM2i could be administered to the patient and at least one biomarker assayed at 1 hour, 2 hours, 3 hours, 4 hours, 8 hours, 16 hours, 24 hours, 48 hours, 3 days, 1 week or 1 month or several months after administration. A second MDM2i could then be administered and at least one biomarker could be assayed for again at 1 hour, 2 hours, 3 hours, 4 hours, 8 hours, 16 hours, 24 hours, 48 hours, 3 days, 1 week or 1 month or several months after administration of the second MDM2i. In each case, all of the biomarkers in Table 2 can be assayed for as a single set.

Another aspect of the invention provides for a method of assessing for suitable dose levels of an MDM2i, comprising monitoring the differential expression of at least one of the genes identified in Table 2 after administration of the MDM2i. For example, after administration of a first bolus of MDM2i, at least one biomarker of Table 2 is analyzed and based on this result, an increase or decrease in MDM2i dosage is recommended. After administration of the adjusted dosage of MDM2i the analysis of at least one biomarker will determine whether the patient is still sensitive to the adjusted dose and that the adjusted dose is providing the expected benefit, e.g., suppressing tumor growth. Alternatively, all of the biomarkers in Table 2 can be assayed for as a single set for assessing sensitivity to the dose of the MDM2i.

Kits for assessing the activity of any MDM2i can be made. For example, a kit comprising nucleic acid primers for PCR or for microarray hybridization for the biomarkers listed in Table 2 can be used for assessing MDM2i sensitivity. Alternatively, a kit supplied with antibodies for at least one of the biomarkers listed in Table 2 would be useful in assaying for MDM2i sensitivity.

It is well known in the art that cancers can become resistant to chemotherapeutic treatment, especially when that treatment is prolonged. Assaying for differential expression of at least one of the biomarkers in Table 2 can be done after prolonged treatment with any chemotherapeutic to determine if the cancer is sensitive to the MDM2i. For example, kinase inhibitors such as Gleevec® will strongly inhibit a specific kinase, but may also weakly inhibit other kinases. There are also other MDM2i, for example, the Nutlin family of compounds. If the patient has been previously treated with another chemotherapeutic or another MDM2i, it is useful information for the patient to assay for at least one of the biomarkers in Table 2 to determine if the tumor is sensitive to an MDM2i. This assay can be especially beneficial to the patient if the cancer goes into remission and then re-grows or has metastasized to a different site.

Screening for MDM2 Inhibitors

It is possible to assay for at least one biomarker listed in Table 2 to screen for other MDM2i. This method comprises assaying a cell with at least one biomarker from Table 2, which predicts if the cell is sensitive to an MDM2i candidate inhibitor, the cell is then contacted with the candidate MDM2i and the IC50 of the treated cell is compared with a known MDM2i contacting a sensitive cell. For example, for cells predicted to be sensitive to any MDM2i as determined by the differential expression of at least one biomarker in Table 2, the candidate MDM2i will have an IC50≤3 µM. The measurement of at least one biomarker from Table 2 expression can be done by methods described previously, for example, PCR or microarray analysis. Alternatively, all of the biomarkers in Table 2 can be assayed for as a single set.

TABLE 2

| Gene Name | Accession number | SEQ ID NO. (nucleotide/protein) |
|---|---|---|
| MDM2 | NM_002392/NP_002383 | SEQ ID NO. 1/SEQ ID NO. 2 |
| CDKN1A | NM_000389/NP_000380 | SEQ ID NO. 3/SEQ ID NO. 4 |
| ZMAT3 | NM_022470/NP_071915 | SEQ ID NO. 5/SEQ ID NO. 6 |
| DDB2 | NM_000107/NP_000098 | SEQ ID NO. 7/SEQ ID NO. 8 |
| FDXR | NM_004110/NP_004101 | SEQ ID NO. 9/SEQ ID NO. 10 |
| RPS27L | NM_015920/NP_057004 | SEQ ID NO. 11/SEQ ID NO. 12 |
| BAX | NM_004324/NP_004315 | SEQ ID NO. 13/SEQ ID NO. 14 |
| RRM2B | NM_015713/NP_056528 | SEQ ID NO. 15/SEQ ID NO. 16 |
| SESN1 | NM_014454/NP_055269 | SEQ ID NO. 17/SEQ ID NO. 18 |
| CCNG1 | NM_004060/NP_004051 | SEQ ID NO. 19/SEQ ID NO. 20 |
| XPC | NM_004628/NP_004619 | SEQ ID NO. 21/SEQ ID NO. 22 |
| TNFRSF10B | NM_003842/NP_003833 | SEQ ID NO. 23/SEQ ID NO. 24 |
| AEN | NM_022767/NP_073604 | SEQ ID NO. 25/SEQ ID NO. 26 |

EXAMPLES

Example 1

Both MDM2i(1) and MDM2i(2) are Equally Potent p53-MDM2 Inhibitors in Biochemical and Cellular Assays TR-FRET Assay for $IC_{50}$ determination: standard assay conditions consisted of 60 µL total volume in white 384-well plates (Greiner Bio-One: Frickenhausen, Germany), in PBS buffer containing 125 mM NaCl, 0.001% Novexin, 0.01% Gelatin, 0.2% Pluronic F-127, 1 mM DTT and 1.7% final DMSO). Both MDM2i(1) and MDM2i(2) were added at different concentrations to 0.1 nM biotinylated MDM2 (human MDM2 amino acids 2-188, internal preparations), 0.1 nM Europium-labeled streptavidin (Perkin Elmer: Waltham, Mass., USA) and 10 nM Cy5-p53 peptide (Cy5-p53 aa18-26, internal preparation). After incubation at room temperature for 15 minutes, samples were measured on a GeniosPro reader (Tecan: Mannedorf, Germany). FRET assay readout was calculated from the raw data of the two distinct fluorescence signals measured in time resolved mode (fluorescence 665 nm/fluorescence 620 nm×1000). $IC_{50}$ values are calculated by curve fitting using XLfit® (Fit Model #205). This data is shown in FIG. 1A.

Determination of binding rate constants ($K_{on}$, $K_{off}$): the rapid mixing tool of GeniosPro reader (Tecan: Mannedorf, Germany) was used to study fast binding kinetics (single well mode). Microplates containing the inhibitor and 20 nM Cy5-labeled p53 peptide in 50 µl assay buffer were placed in the reader. After 10 min equilibration at 25° C., binding reactions were initiated by injecting 50 µl of buffer containing 0.2 nM biotinylated MDM2 and 0.2 nM europium-streptavidin at 475 µl/s. Fluorescence was measured at 665 nM and at various time intervals, the first one 0.6 s after injection. In the absence of inhibitor, Cy5 fluorescence was maximal already at 0.6 s and remained stable for at least 15 min. In the presence of MDM2i(1) and MDM2i(2) fluorescence decreased slowly and measurements were made until steady-state was achieved. Control fluorescence was taken as the difference between wells containing 1% DMSO and wells containing 10 µM Nutlin-3 as a control. The inhibitory effect at each time point was calculated as percent of the corresponding control. Progress curves obtained in the presence of different concentrations of inhibitor were combined and fitted as a whole. Nonlinear regression was performed with XLfit® using a novel fit methodology that was designed to obtain precise $K_{on}$ and $K_{off}$ values, based on the following respective equations: Fit=[Imin+((Imax−(((Ki^nH)*Imax)/((y^nH)+(Ki^nH))))* (1−exp(((−1)*(koff+((y*koff)/Ki)))*x)))] and Fit=[Imin+ ((Imax−(((Ki^nH)*Imax)/((y^nH)+(Ki^nH))))*(1−exp (((−1)*(kon*(Ki+y)))*x)))], where Ki represents the constant of inhibition, Imin represents the minimum inhibition (in %), Imax represents the maximum inhibition (in %), nH represents the Hill coefficient, x represents the time and y represents the inhibitor concentration). This data is shown in FIG. 1A.

Cell proliferation inhibition and GRIP p53 translocation assay: Effects of MDM2i(1) and MDM2i(2) on cellular growth and loss of viability is measured in both p53 wild-type (SJSA-1 and HCT116 p53$^{wt/wt}$ cells) and p53 mutant cell lines (SAOS2 and HCT116 p53$^{-/-}$ cells) using a standard proliferation assay based on the DNA-interacting fluorescent dye YOPRO (Invitrogen: Lucern, Switzerland). Briefly, cells are plated in 96-well plates overnight at 37° C. and are treated with increasing concentrations of MDM2i(1) or MDM2i(2) for 72 hours. Cell concentration in each well is then determined using the DNA-interacting fluorescent dye YOPRO according to the manufacturer's instructions and the fluorescent signal is measured using a Gemini-EM standard plate reader (Molecular Devices: Sunnyvale, Calif., USA). $IC_{50}$ values are calculated by curve fitting using XLfit® (Fit Model #201) and this data is shown in FIG. 1A.

The mechanistic p53-MDM2 Redistribution assay (GRIP assay) is used to directly monitor in cells the ability of compounds to modulate the p53-MDM2 protein-protein interaction. In this fully engineered assay, the p53 protein is tagged with a fluorescent GFP-label and is bound to MDM2 protein which is anchored in the cytoplasm of the cells. The treatment of the cells with specific compounds causes the dissociation of the interaction between the two proteins and the translocation of the released p53-GFP protein from the cytoplasm to the nuclei. This effect is detected and quantified using a high content imaging platform using the ArrayScan-VTi (Cellomics), following the fluorescent signal over time (see FIG. 1B, GRIP p53 translocation assay).

Altogether, using both in vitro and cellular assays, the results presented in FIGS. 1A and 1B show that both MDM2i (1) and MDM2i(2) are comparable potent p53-MDM2 protein-protein interaction inhibitors in vitro, inhibiting the p53-MDM2 protein-protein interaction, hampering tumor cell proliferation in a p53-dependent manner, and inducing p53 accumulation and translocation to the nucleus. This data is shown in FIG. 1B; note that there are large discrepancies in the IC50 between the cell lines. This is also an indication that there are differences in the sensitivity between the two cell lines to an MDM2i, and thus a determination of sensitivity can be useful in determining which patients receive the therapeutic.

Example 2

The p53 Mutational Status is Associated with MDM2i Chemical Sensitivity in Cell Lines The association of p53 mutation to MDM2i(2) chemical sensitivity in a panel of cancer-relevant cell lines was tested by Fisher's Exact test. The cell line panel is the one covered by the Cancer Cell Line Encyclopedia (CCLE) initiative (Barretina J., Caponigro G., Stransky N., Venkatesan K., et al. The Cancer Cell Line Encyclopedia enables predictive modeling of anticancer drug sensitivity. Nature 483:603-7, 2012). A detailed genomic, genetic and pharmacologic characterization was conducted on the CCLE cell lines.

p53 mutation status in CCLE cell lines is taken from a data source of gene-level genetic alterations, for example, point-mutations, insertions, deletions and complex genetic alterations, compiled from the Sanger center COSMIC data and internal sources including Exome Capture Sequencing. This comprises data from approximately 1,600 cancer-related genes over the CCLE cell lines. Analysis of the CCLE panel revealed 244 cell lines containing a mutant p53, and 112 cell lines that expressed wild type p53.

The MDM2i(2) chemical sensitivity was determined from the pharmacologic characterization of the CCLE cell lines. The cell lines were separated in two groups according to MDM2i(2) sensitivity. One group contains the cell lines sensitive to MDM2i(2) compound, while the other group encompasses those being chemically insensitive to the MDM2i(2) compound. Such stratification resulted in two groups of 47 sensitive and 309 insensitive cell lines, respectively. From such in vitro chemical sensitivity data, the prediction that a cell would be sensitive to an MDM2i treatment was estimated to be 13%.

The statistical testing of the p53 mutation to sensitivity groups association shows an association between p53 mutation (mt) and the chemical sensitivity to MDM2i(2) (FIG. 2). The mt panel in FIG. 2 displays the MDM2i(2) sensitivity profiles for p53 mutated CCLE cell lines, the wild type (wt) panel displays the MDM2i(2) sensitivity profiles for p53 wild-type CCLE cell lines. Amax is defined as the maximal effect level (the inhibition at the highest tested MDM2i(2) concentration, calibrated to MG132, a proteasome inhibitor used as a reference, as described in the CCLE publication referenced above, and IC50 is defined as of the µM concentration at which MDM2i(2) response reached an absolute inhibition of −50 with respect to the reference inhibitor. Cell line count broken down by MDM2i(2) chemical sensitivity and p53 mutation status, and associated statistics: Data is also displayed as a contingency table with associated statistics.

This data indicates it is more likely for a cell line to show sensitivity to MDM2i(2) if its p53 mutation status is wild type. Indeed, the majority of p53 mutated cell lines are found insensitive to the compound, whereas more than two-third of p53 wild type cell lines are sensitive.

From this data we can conclude a p53 wild type genotype is the first indication of MDM2i sensitivity, and therefore it is the first stratification biomarker to be considered for selecting cancer patients responsive to an MDM2i.

Example 3

Prediction of Cell Line Chemical Sensitivity to MDM2i from Genomic Data and Clinical Implication The two cell line sensitivity groups, given by MDM2i(2) treatment, are compared with the aim of identifying the biomarkers differentiating the sensitive cell lines from the insensitive cell lines, prior to any MDM2i treatment. Such biomarkers are used to predict the sensitivity of any MDM2i treatment. The biomarkers analyzed are the following types: 1) gene-level expression values generated by the Affymetrix GeneChip™ technology with the HG-U133 plus 2 array, summarized according to the RMA normalization method; 2) gene-level chromosome copy number values, obtained with the Affymetrix SNP6.0 technology (Affymetrix Santa Clara, Calif., USA) and processed using the Affymetrix apt software, and expressed as log 2 transformed ratios to a collection of HapMap reference normal samples; 3) gene-level genetic alterations or mutations, as described above in Example 2; 4) pathway-level expression values, summarizing pathway expression levels by a standardized average approach over the genes contributing to the pathways, as referenced in the GeneGo Metacore® knowledge base; 5) cell line lineage (cell line tissue of origin); 6) gene-level Tumor suppressor status, summarizing the activation status of a selection of tumor suppressor genes, by integrating the genetic alteration, copy number and expression information. Such genomic data was generated in the context of the CCLE cell line genomic and genetic characterization, and covers a total of about 45,000 genomic features.

Wilcoxon signed-rank tests or Fisher's exact tests are used to compare the two cell line group genomic features, depending on the feature type. The features having continuous values (gene expression and copy number, pathway expression features) are subjected to Wilcoxon signed-ranked test, those having discrete values (genetic alteration, tumor suppressor status and lineage features), to Fisher's exact test, for differential profile evaluation between sensitive and insensitive cell line groups. The significant features, discriminating the sensitive cell line group from the insensitive one, are the ones passing a false discovery rate-controlled p-value cutoff. Irrespective of the p-value limit, a minimum or maximum number of features per feature type are also required. To minimize the impact of the high degree of correlation among the features on the feature selection step, the feature data is clustered before the statistical tests as a pre-processing step. This step is performed at the feature type-level using the Frey's and Dueck's Affinity Propagation method (Clustering by Passing Messages Between Data Points. Frey B. and Dueck D. Science 315:972-6, 2007), and retrieves a set of features representing the most variability.

The cell line sensitivity groups or classes are defined as follows for this two-class comparison aiming at biomarker identification: a sensitive group of 47 sensitive cell lines, and an insensitive group of 204 insensitive cell lines. The 204 cell lines making this insensitive group are the most insensitive ones from the 309 insensitive cell line set mentioned in Example 2. This feature selection step yielded a total of about 200 significant features, having a significant differential profile to differentiate the sensitive cell line group from the insensitive one, and thus having the required properties to be considered as markers to predict the chemical sensitivity of samples to an MDM2i. As described above in Example 2, a relevant biomarker is the p53 mutation status itself. The statistics of the feature selection step (p-value 1.17E-21) confirmed its role in predicting sensitivity to an MDM2i. Furthermore, the odds-ratio associated with p53 status (0.024) indicates p53 mutation is more represented in MDM2i insensitive cell lines. Still noteworthy and still according to the statistics of the feature selection step, most of the predictive biomarkers are found to be a subset of p53 transcriptional target genes. These are shown in Table 2/FIG. 3. Their fold-changes indicate the transcripts of these biomarkers are more expressed in the MDM2i sensitive cell line population, as shown in FIG. 3. This is likely indicative of a level of p53 functional activity pre-existing before any treatment in cell lines that are sensitive to an MDM2i.

That the biomarkers in Table 2/FIG. 3 are reflective of a functional p53 pathway in MDM2i sensitive cells is verified in FIG. 4. In FIG. 4, cells have been treated with increasing concentrations of MDM2i(1) for 4 hours, prior to cell lysis. Whole cell lysates were prepared using a cell lysis buffer containing 50 mM Tris-HCl pH 7.5, 120 mM NaCl, 1 mM EDTA, 6 mM EGTA pH 8.5, 1% NP-40, 20 mM NaF, 1 mM PMSF and 0.5 mM Na-Vanadat, proteins were separated on NuPAGE 4-12% Bis-Tris Gel (Invitrogen # NP0322BOX, Lucerne; Switzerland), transferred onto Nitrocellulose Protran® BA 85 membranes (Whatman #10 401 261: Piscataway, N.J., USA) at 1.5 mA/cm$^2$ membrane for 2 h using a semi-dry blotting system, and immunoblotted with either an anti-phospho-p53 (Ser$^{15}$) (1/1000; Cell Signaling Technology #9284: Beverly, Mass., USA) rabbit polyclonal antibody, or an anti-p53 (Ab-6) (Pantropic, clone DO-1,) (1/1000; Calbiochem # OP43 San Diego, Calif., USA), an anti-MDM2 (Ab-1, clone IF2) (1/1000; Calbiochem # OP46), an anti-p21$^{WAF1}$(Ab-1, clone EA10) (1/500; Calbiochem # OP64: San Diego, Calif., USA) or an anti-α-Tubulin (Sigma # T5168: St. Louis, Mo., USA) mouse monoclonal antibodies, as indicated. As shown in FIG. 4, increasing concentrations of MDM2i(1) induces stabilization of p53 protein levels, with no significant increase of phospho-p53 in both C3A and COLO 792 cells. Interestingly, treatment with MDM2i(1) also induces a strong de novo expression of both p53 target genes p21(CDKN1A) and MDM2 in C3A sensitive cells, but not in COLO-792 insensitive cell line. Altogether, this data indicates that sensitivity to an MDM2i inhibitor is directly related to the presence of an intrinsic functional p53 pathway, that the biomarkers in Table 2/FIG. 3, taken together as a set or alone, point directly to p53 pathway functionality before treatment, and indicates these biomarkers have a strong ability to predict patient sensitivity that correlates with the mechanism of action of p53.

The significant genomics features are used as the basis features for naïve Bayes probabilistic modeling of the two MDM2i chemical sensitivity groups, or classes. The goal of the modeling step is to derive a classification scheme or classifier that predicts the patient's response (either sensitive or insensitive) of an unknown sample with a certain confidence. The predictive model is defined by training a naïve Bayes algorithm over the entire chemically characterized CCLE cell line population stratified into the two above-mentioned sensitivity classes. The performance of the classifier is evaluated through 5 repeats of 5-fold cross-validations of the data used to train the model. The model performance is summarized with the following class-level measures: sensitivity, specificity, positive predictive value, and negative predictive value. The sensitive class is used as the reference for the sensitivity and positive predicted value calculations. The default output of the naïve Bayes algorithm is a score or probability, for each predicted sample to be assigned to one class or the other. A probability threshold is defined to transform the probability scores into a sensitive or insensitive class-level prediction. The probability threshold is defined as the probability maximizing the sensitivity and specificity calculated over all predicted samples. The entire and nearly-identical procedure is described in more details in the CCLE publication referenced in Example 2.

To demonstrate a better predictive power can be achieved from at least one biomarker found in Table 2, and alternatively, the biomarkers in Table 2 as a set, than from p53 mutation status alone, or from the entire predictive feature set of about 200 genes, naïve Bayes models from each of these feature sets were trained, and their performance assessed by cross-validation, as above mentioned, and compared (FIG. 5). FIG. 5 demonstrates the selected biomarkers found in Table 2 outperform both the p53 mutation status and the larger group of about 200 significant features, and provide a substantial improvement in predicting patient responsiveness to an MDM2i. This is particularly striking when performances are evaluated by positive predictive value (PPV).

A positive predicted value (PPV) of 76% suggests that 76% of the predicted sensitive cell lines will be sensitive to MDM2i treatment. As an extrapolation to a clinical setting, a PPV of 76% also suggests that 76% of cancer patients, predicted as sensitive to MDM2i(2) from tumor biopsies, would show clinical response upon MDM2i(2) treatment. This enrichment of clinical response by patient stratification, using the biomarkers in Table 2 and associated with the naïve Bayes predictive model, was compared to the baseline clinical response rate without prior patient stratification. The baseline clinical response rate estimated from the chemical sensitivity data is 19% Thus, in a clinical perspective; the biomarkers of Table 2 have a clear increase of the clinical response in the predicted sensitive patient population. This increase in prediction is greater and more specific than assaying for p53 status alone or all of the approximately 200 genomic features initially selected. This can be seen in FIG. 5, where the "All 200 biomarkers" feature bar is the PPV of the approximately 200 genomic features initially selected. The PPV reported for "All 200 biomarkers" feature is 59%. The PPV for using p53 alone is 56% (FIG. 5). The PPV of the set of biomarkers disclosed in Table 2 is 76% ("Table 2 selected biomarkers"). This is a surprising result, as in general, the larger data set of 200 genomic features would provide more data points and more insight into prediction of MDM2i sensitivity. However, this is not the case, as the biomarkers in Table 2, when taken as a set, provide a 17% increase in predictive value. This is important in the clinic, as now 17 additional patients out of 100 would be predicted to receive the correct treatment.

In order to test the predictive value of the biomarkers of Table 2, 52 cell lines that were not previously examined in the pharmacologic characterization as part of the CCLE project, were assayed for their sensitivity to MDM2i in proliferation assays. Briefly, cells are plated in 96-well plates overnight at 37° C. and are treated with increasing concentrations of an MDM2i for 72 hours. Cell concentration in each well is then determined using the CellTiter-Glo Luminescent Cell Viability Assay® (Promega Cat. # G7571/2/3: Madison Wis., USA), according to the manufacturer's instructions and the luminescent signal is measured using a SYNERGY HT plate reader (BioTek: Winooski, Vt., USA). $IC_{50}$ values are calculated by curve fitting using XLfit® (FIG. 6). Sensitivity of cell lines to an MDM2i is determined by comparing the observed $IC_{50}$ of all cells that were tested in cell proliferation inhibition assay as described in Example 1. The cut-off for sensitivity was determined at $IC_{50} \leq 3$ μM for both MDM2i(1) and MDM2i(2). Predictions of sensitivity for every cell lines are performed using the predictive model as described above, to confirm the values disclosed in FIG. 5. The cell lines are from a variety of tumors. For example; melanoma (COLO-829, COLO-849, IGR-1, MEL-JUSO, SK-MEL-1, SK-MEL-31, UACC-62, UACC-257), leukemia (BV173, EOL-1, GDM-1, HuNS1, L-540, MV-4-11, OCI-LY3, RS4:11, SUP-B15, HDLM2, JM1), breast cancer (CAL51, EFM-192, HCC202), pancreatic cancer (DAN-G), hepatic cancer (JHH-5) and lung cancer (RERF-LCK-KJ). This assay was done with the all of the biomarkers disclosed in Table 2 as a single set. Overall, 36/52 cell lines were predicted to be sensitive to an MDM2i, and of these 36 cell lines 24 were sensitive, resulting in a positive predictive value of 66%, again a significant increase in predictive value (PPV) over assaying for p53 alone. With regard to screening out the non-responding cells, 16/52 cell lines were predicted to be insensitive to a p53-MDM2 inhibitor, and 13/16 were found to indeed be insensitive, leading to a significant negative predictive value (NPV) of 81%. Overall, these data are similar to the predictive model performances described in FIG. 5. The actual in vitro testing of unrelated cell lines allowed testing of the MDM2i chemical sensitivity predictive model, hence validating the biomarkers disclosed in Table 2.

Example 4

MDM2i Treatment Inhibits Tumor Growth Inhibition In Vivo which is Correlated to a Dose-Dependent Increase of p21(CDKN1A) mRNA and Protein Levels in Tumors To further validate the predictive biomarkers disclosed in FIG. 3, in vivo human xenograft models either from human primary samples or from cell lines were directly injected and grown in tumors subcutaneously in mice and then assessed for MDM2i sensitivity. All the animals were allowed to adapt for 4 days and housed in a pathogen-controlled environment (5 mice/Type III cage) with access to food and water ad libitum. Animals were identified with transponders. Studies were performed according to procedures covered by permit number 1975 issued by the Kantonales Veterinäramt Basel-Stadt and strictly adhered to the Eidgenössisches Tierschutzgesetz and the Eidgenössische Tierschutzverordnung. Subcutaneous tumors were induced by concentrating $3.0 \times 10^6$ SJSA-1 osteosarcoma cells in 100 μl of PBS (without $Ca^{2+}$ and $Mg^{2+}$) and injecting in the right flank of Harlan nude mice. The administration of MDM2i began 12-14 days post cell injection. MDM2i was prepared immediately before each administration. MDM2 is were dissolved in 0.5% HPMC (hydroxypropylmethylcellulose) and were injected daily (q24h) at 25, 50 or 100 mg/kg. Tumor volumes (TVol), determined from caliper measurements (using the formula l×w× h×τ/6) were measured three times per week. Tumor response was quantified by the change in tumor volume (endpoint minus starting value in $mm^3$) as the T/C, i.e.

$$\left(\frac{\Delta TVol_{drug}}{\Delta TVol_{vehicle}} \times 100\right).$$

In the case of a tumor regression, the tumor response was quantified by the percentage of regression of the starting TVol, i.e.

$$\left(\frac{\Delta TVol_{drug}}{TVol_{Day0}} \times 100\right).$$

The body-weight (BW) of the mice was measured three times per week allowing calculation at any particular time-point relative to the day of initiation of treatment (day 0) of both the percentage change in BW (Δ % BW). As shown in FIG. 7A, a 10-day treatment of SJSA-1 xenografted tumors with MDM2i(1) led to a dose-dependent tumor growth inhibition with a significant T/C of 50% at 25 mg/kg q24h and of 3% (stasis) at 50 mg/kg q24h. At 100 mg/kg q24h for 10 days, MDM2i(1) treatment induced a significant tumor regression of 65% (FIG. 7B). All doses were well tolerated at q24h schedule, as indicated by the mean body weight curves over time.

Anti-tumor activity of MDM2i(1) was correlated with a significant dose-dependent induction of p21(CDKN1A) mRNA levels in tumors (FIG. 7C). Briefly, total RNA was purified from cell pellets using the QIAshredder® (79654, Qiagen: Valencia Calif., USA) and RNeasy Mini Kit® (74106, Qiagen: Valencia Calif., USA) according to the manufacturer's instructions, with the exception that no DNA digestion was performed. Total RNA was eluted with 50 μL of RNase-free water. Total RNA was quantitated using the spectrophotometer ND-1000 Nanodrop® (Wilmington Del., USA). The qRT-PCR (Quantitative Reverse Transcriptase Polymerase Chain Reaction) was set up in triplicate per sample using the One-Step RT qPCR Master Mix Plus (RT-QPRT-032×, Eurogentec: Seraing, Belgium), with either control primers and primers for human p21(CDKN1A) (Hs00355782_m1, Applied Biosystems: Carlsbad Calif., USA) or mouse p21(CDKN1A) (Mm00432448_m1, Applied Biosystems: Carlsbad Calif., USA), namely TaqMan Gene Expression kit assays (20× probe dye FAM™ (or VIC)-TAMRA (or MGB); Applied Biosystems: Carlsbad Calif., USA). More specifically, a master mix was prepared on ice for a final concentration of: 1× Master Mix buffer, 1× primer solution, and 1× Euroscript reverse transcriptase, combined with $H_2O$, total volume: 8 μL/well. A MicroAmp Optical 384-well Reaction Plate (4309849, Applied Biosystems) was fixed on the bench, and 2 μL of mRNA (concentration: 10 or 20 ng/μl) (or water for negative control) were pipetted in triplicate, followed by addition of 8 μL/well of master mix. The plate was then covered with a MicroAmp Optical Adhesive film kit (4313663, Applied Biosystems: Carlsbad Calif., USA), centrifuged for 5 min at 1000 rpm at 4° C. and placed in a 7900 HT Fast Real-Time PCR System (Applied Biosystems: Carlsbad Calif., USA). The program was run with one cycle of 48° C. for 30 min, one cycle of 95° C. for 10 min, and finally 40 cycles of alternating 95° C. for 15 sec and 60° C. for 1 min. The number of cycles (CT) was determined, $2^{-CT}$ values were calculated, and the value normalized by dividing with the $2^{-CT}$ value obtained from the Gapdh control. Fold increase over control (i.e. DMSO- or vehicle-treated animals) was calculated and plotted in the bar graph.

Figure 8:
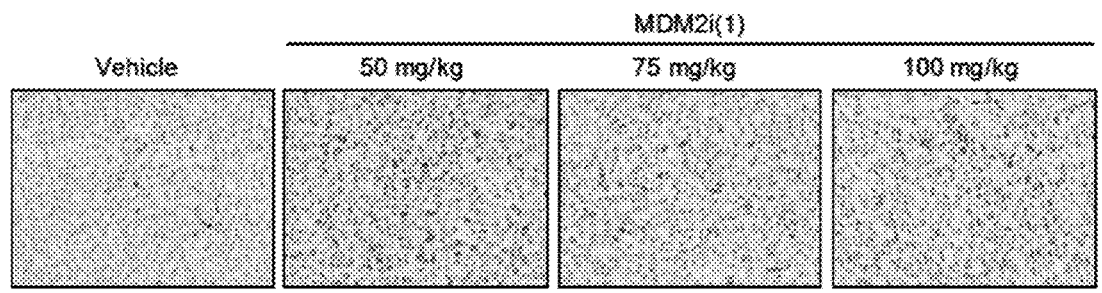
FIG. 8 shows the expression of p21(CDKN1A) at the protein level after treatment of MDM2i(1) sensitive cells at efficacious doses.

In addition, the anti-tumor activity of MDM2i(1) was correlated with a significant dose-dependent induction of p21 (CDKN1A) protein levels in tumors, as judged by immunohistochemistry (FIG. 8). SJSA-1 xenograft tumors were collected and a 3-4 mm slice out of the middle of the tumor was removed, transferred into pre-labelled histo-cassettes and immersion-fixed in neutral buffered formalin (NBF) 10% (v/v) (pH 6.8-7.2) (J. T. Baker, Winter Garden, Fla., USA), pre-cooled at 4° C. Tumors were then fixed at room temperature for 24 hours, followed by processing in the TPC 15Duo (Tissue Processing Center, Medite) for paraffinization. Subsequently, the tumor slices were embedded in paraffin and from each paraffin block several 3 µm thick sections were cut on a rotary microtome (Mikrom International AG, Switzerland), spread in a 48° C. water-bath, mounted on glass slides (SuperFrost Plus, Thermo Scientific: Waltham Mass., USA), and dried in an oven either at 37° C. overnight or at 60° C. for 30 min. Dry tissue section were processed for immunohistochemistry (IHC) staining. p21(CDKN1A) immunohistochemistry has been performed using the mouse monoclonal antibody clone SX118 from Dako (Cat. No. M7202 Dako: Carpenteria Calif., USA) at a dilution of 1:50. Immunohistochemistry has been performed on a Ventana Discovery XT automated immunostainer using the N-Histofine Mousestain Kit (Nichirei Bioscience Inc, Japan) in combination with the DABMap Kit chromogen system, omitting the SA-HRP solution (Ventana/Roche Diagnostics GmbH, Mannheim, Germany). Antigen retrieval was done by using Cell Conditioning ULTRA® (Ventana/Roche Diagnostics GmbH, Mannheim, Germany) at mild (95° C. for 8 min+100° C. for 20 min) conditions. Mouse cross reactivities were blocked by using Blocking Reagents A and B from the N-Histofine Mousestain Kit® (Nichirei Bioscience Inc, Japan) before and after primary antibody incubation, following the manufacturer instructions. The primary antibody was applied manually at the desired dilution in Dako antibody diluent (AbD), followed by incubation for 1 hour at ambient temperature. Corresponding negative controls were incubated with AbD only. Sections were subsequently stained using the labeled polymer system Simple Stain Mouse MAX PO (M) from the N-Histofine Mousestain Kit® (Nichirei) and DAB substrate from the DABMap Kit (Ventana/Roche Diagnostics). Counterstaining of sections was done using hematoxylin (Ventana/Roche Diagnostics). After the automated staining run, slides were dehydrated in a graded series of ethanol, cleared in xylene and mounted with Pertex® mounting medium.

Example 5

Prediction of MDM2i(2) Sensitivity in Human Primary Tumor Mouse Xenograft Models and in Human Primary Tumors The biomarkers in Table 2, were used in association with a naïve Bayes predictive model to predict MDM2i sensitivity in a collection of human primary tumor samples and xenograft models, to demonstrate whether the biomarkers, and their associated predictive power, exists outside of in vitro cell line systems.

The gene-level expression values of all the biomarkers of Table 2 were used as the feature basis for naïve Bayes probabilistic modeling. They were generated as described in Example 3, the only difference being in the RMA summarization step where the normalization was targeted to a reference set of normal & tumor samples. The naïve Bayes modeling is conducted as described in Example 3.

The human primary tumor samples and xenograft models submitted for sensitivity prediction were a collection of about 18,000 and 503 samples, respectively, for which gene expression profiles, generated with Affymetrix technology (Human Genome U133 plus 2.0 array), are available. The samples of the collection were internally annotated with controlled vocabulary for sample ontology including pathology, histology and primary site. The associated gene chip data was gathered from both public and internal sources, and normalized as described above to the same reference sample set for consistency.

Ratios of MDM2i predicted sensitive samples from the collection were compared to the proportions of sensitive cell lines, as given by the MDM2i(2) chemical sensitivity data described in Example 3 above. A good correlation is expected to demonstrate the ability of the biomarkers disclosed in FIG. 3 to be predictive for MDM2i sensitivity in human primary tumor samples. For clarity, as well as to potentially identify lineages in which sensitive cell line proportions are underestimated in the cell line chemical sensitivity data, sensitive prediction ratio to sensitive cell line ratio comparison is broken down by tissue of origin.

FIG. 9 (left panel) shows a correlation between predicted sensitive human primary tumor samples from the collection and the sensitive cell lines from MDM2i chemical sensitivity data. It indicates the biomarkers disclosed in Table 2 and its use for predicting sensitivity outside of in vitro cell line samples is valid. It also indicates that the biomarkers disclosed in Table 2 can be used to predict MDM2i chemical sensitivity in human primary tumor samples. It reveals new tumor indications which have not been investigated previously and confirms results found in the current study The new indications, for example, liver (hepatocellular carcinoma) and kidney (renal cell carcinoma), represent potentially new disease indications to be pre-clinically and clinically evaluated with the biomarkers disclosed in Table 2 for treatment with an MDM2i. FIG. 9A also indicates that the biomarkers disclosed in Table 2 can be used to predict MDM2i chemical sensitivity in primary melanoma tumors, consistent with the results found in the current study.

FIG. 9 (right panel) shows a correlation between the fractions of predicted sensitive human primary tumor samples and the predicted sensitive ratios in the primary tumor xenograft collection. The tumor samples/xenografts/cell lines are organized by lineage. The dashed line in both panels is the identity line. It shows the data generated from the in vivo mouse xenograft models, in which the exemplified signature and associated predictive classifier can be studied and validated, is in line with the data from the rest of the in vivo collection samples. It confirms the mouse xenograft models as a source of material to validate the p53 downstream target gene based classifier approach to predict clinical outcome of cancer patients and diseases indications, in an in vivo pre-clinical setting.

Example 6

Single Biomarkers and any Combinations of the Identified Thirteen Biomarkers Predict Chemical Sensitivity to MDM2i The thirteen biomarkers depicted in Table 2, when used in association with a naïve Bayes predictive modeling framework, predict MDM2i sensitivity in both in vitro systems and in vivo, as exemplified in Examples 3 and 5. To investigate whether subsets of these thirteen biomarkers would also predict for MDM2i sensitivity, single biomarkers and multiple combinations of them are employed as feature basis for predictive modeling. Their prediction performances are then compared to the ones achieved with either the full thirteen biomarkers or with p53 mutation status when used as a predictive feature for MDM2i sensitivity prediction.

Two instances of p53 mutation status are considered in Example 6. These two instances are defined from the Exome Capture Sequencing data of the CCLE cell lines, as mentioned in Example 2, and are meant to be surrogates of clinical settings where the p53 gene is sequenced for stratification or clinical annotation of patients.

The first instance of p53 mutation status is defined from the mutations spanning exons 5 to 8 of p53. Exons 5 to 8 encompass the DNA binding domain of p53, which contains the majority of described p53 mutations, and are the p53 exons commonly targeted for sequencing in clinical settings (for example, Rapid sequencing of the p53 gene with a new automated DNA sequencer. Bharaj B., Angelopoulou K., and Diamandis E., Clinical Chemistry 44:7 1397-1403, 1998). The second instance considers the complete open reading frame of the main p53 transcript, and is therefore defined from all coding exon mutations.

Multiple biomarker combinations can be generated from the list of 13 biomarkers disclosed in Table 2. All combination types from 2 to 12 biomarkers are evaluated as feature basis for predictive modeling of MDM2i chemical sensitivity. When more than 50 different combinations exist for a given combination type, the number of evaluated combinations is restricted to 50. All 50 combinations in each combination type were randomly picked.

All predictive models associated to the above described feature sets (single biomarkers, 2-to-12 biomarker combinations, p53 mutation status instances) were trained and evaluated mostly as described in Example 3. What differs from Example 3 is as follows: The training data was slightly larger than the one used is Example 3 and encompasses 264 cell lines (47 from the sensitive class, and 217 from the insensitive class); A p-value threshold of 0.5 was used upon the naïve Bayes probabilistic modeling to call a cell line either sensitive or insensitive in the 5-fold cross-validation scheme. Moreover, all sample strata generated by the cross-validation processes were randomly selected and independent from one-another. The performances of the combinatorial predictive models and their comparisons to the p53 mutation status instance and 13 biomarker models are shown in FIGS. 10 to 12.

FIG. 10 depicts the positive predicted values (PPV) achieved by the single biomarker, the combinatorial, the thirteen biomarker and the p53 mutation models. The PPV is an estimate of the clinical efficacy one would expect in a clinical trial upon patient selection with the considered modeling process. For convenience, the data is depicted as box-and-whisker plots when there are more than five data points to plot per feature set.

FIG. 10 shows that combinations from as few as two and three biomarkers outperform exon 5-to-8 p53 mutation ("ex5to8mt") and all-exon p53 mutation features ("allExMt"), respectively. Indeed, the upper and lower boundaries defined by the ends of the whiskers encompass about 99% of the data points, assuming a normal distribution of the data. Therefore, the majority of the evaluated 2- and 3-biomarker combinations show a higher PPV than the ones achieved by the p53 mutation status instances. Moreover, even if all single gene models do not outperform the two p53 mutations instances, a majority of them (around 75%, the box plus the upper whisker) outperforms the p53 all-exon mutations. Noteworthy, all single gene models give rise to PPVs that are higher than the sensitive cell line ratio (~18%) in the considered sample population, indicating that MDM2i sensitivity prediction models, built from as few as one biomarker, are capable of enriching the selected samples in sensitive ones.

Additionally, under this modeling exercise, as plotted in FIG. 10, the PPV given by the p53 exons 5-to-8 mutation status model, averaged over the 5 cross-validation repeats, is 48%. It is significantly lower than the p53 mutation PPV disclosed in Example 3 (56%). This indicates that, in a clinical setting where p53 exon 5-to-8 sequencing is employed for patient selection, which is common practice, the exemplified 13 biomarker-based patient selection has even higher added value than anticipated from Example 3.

FIG. 11 shows the specificities achieved by the several evaluated models. As for PPV in FIG. 10, every combination made from as few as 2 biomarkers is sufficient to achieve specificity higher than the ones obtained from the mutations instances only. All single biomarker models outperform the mutations, when specificity is used to monitor the model performances.

FIG. 12 shows the sensitivities. Sensitivity is also called recall, and is an estimate of the truly sensitive patient population retained upon patient selection. Combinations of 9 biomarkers as the feature basis for MDM2i sensitivity prediction models are sufficient to obtain sensitivities comparable to the one achieved the full 13 biomarker list. However, only a few 9-biomarker combinations would achieve sensitivities higher than the ones given by the 2 p53 mutation status predictive models. But noteworthy, all evaluated combinations, from as few as 2 biomarkers, and a majority of single biomarker models, display sensitivities higher than the one which is expected by chance upon random classification (~18%).

In conclusion from FIGS. 10, 11 and 12, single biomarkers, when used as feature basis in models predicting chemical sensitivity to MDM2i, are sufficient to achieve sample sensitivity predictions that would result in a significant enrichment of potentially MDM2i responding patient in a clinical setting. Furthermore, combinations made from any 2 biomarkers, or more, increase the expected clinical efficacy with respect to the one obtained with p53 mutation-based patient selection. Assembling 8 biomarkers, from any of the Table 2 thirteen ones, are sufficient to achieve a patient recall equivalent to the one given by the 13 biomarker model. The predictive model performance metrics, obtained for the 13 gene signature and associated combinations, can be further optimized by optimizing the class assignment p-value threshold used in the naïve Bayes probabilistic step of the model, as it was done in Example 3.

In a further embodiment, it is investigated whether the biomarkers depicted in Table 2 could predict MDM2i chemical sensitivity in collaboration with p53 mutation status. Single biomarkers and combinations of 2 biomarkers and above are combined with p53 mutation status in feature lists. The feature lists are then utilized as basis for sensitivity predictive modeling, as previously and described above. The performances of the multiple resulting models are evaluated as described above.

The p53 mutation status instance which is used as an example is the p53 exon 5-to-8 mutations. FIGS. 13, 14 and 15 depict the PPVs, specificities and sensitivities of those models combining p53 mutation with biomarkers, respectively, and are compared to the results given by mutation only models and the full 13-biomarker model.

FIG. 13 shows that at least a single biomarker from the list of 13, in collaboration with p53 mutation status, is sufficient to achieve a PPV higher that the basal sensitivity rate (18%) in the data. It also shows that a single biomarker at minimum, still in combination with p53 mutation status, achieves a higher PPV than the ones obtained with the two above mentioned p53 mutation status instances, when employed as features in a predictive model. And finally, any 5 biomarkers in combination with p53 mutation recapitulate the PPV which is achieved by the 13 biomarker model.

The same conclusions are drawn from FIGS. 14 and 15 when specificities and sensitivities are taken into account as model performance metrics. Noteworthy from FIG. 15, a high sensitivity can be obtained from as few as one biomarker, when modeled along with p53 mutation.

In conclusion, combining a single or multiple biomarkers from Table 2 with p53 mutation status enables the prediction of MDM2i sensitivity, and would result, when applied for patient selection in a therapeutic or clinical setting, in a significant enrichment with a limited loss of potential MDM2i responding patients.

The invention claimed is:

1. A method of treating a cancer patient comprising:
   a) measuring differential gene expression of the biomarkers MDM2, CDKN1A, ZMAT3, DDB2, FDXR, RPS27L, BAX, RRM2B, SESN1, CCNG1, XPC, TNFRSF1OB and AEN in a cancer sample obtained from the patient;
   b) determining differential expression of the biomarkers by comparing the measured gene expression of the biomarkers in the cancer sample with the gene expression of the biomarkers in a control sample, wherein the control sample has a functional p53 gene pathway;
   c) determining sensitivity of the patient to a MDM2i(1); and
   d) administering to the patient MDM2i(1);
   (e) wherein the cancer sample is selected from the group consisting of breast, lung, pancreas, colon, liver, leukemia, melanoma and kidney.

2. The method of claim 1 further comprising obtaining a biological sample from the patient prior to the administration of the MDM2i(1).

3. The method of claim 1, wherein the MDM2i(1) is administered in a therapeutically effective amount.

* * * * *

SEQUENCE LISTING

```
<160> NUMBER OF SEQ ID NOS: 26

<210> SEQ ID NO 1
<211> LENGTH: 7472
<212> TYPE: DNA
<213> ORGANISM: Homo sapiens

<400> SEQUENCE: 1
gcaccgcggc gagcttggct gcttctgggg cctgtgtggc cctgtgtgtc ggaaagatgg      60
agcaagaagc cgagcccgag gggcggccgc gacccctctg accgagatcc tgctgctttc     120
gcagccagga gcaccgtccc tccccggatt agtgcgtacg agcgcccagt gccctggccc     180
ggagagtgga atgatccccg aggcccaggg cgtcgtgctt ccgcgcgccc cgtgaaggaa     240
actggggagt cttgagggac ccccgactcc aagcgcgaaa accccggatg gtgaggagca     300
ggcaaatgtg caataccaac atgtctgtac ctactgatgg tgctgtaacc acctcacaga     360
ttccagcttc ggaacaagag accctggtta gaccaaagcc attgcttttg aagttattaa     420
agtctgttgg tgcacaaaaa gacacttata ctatgaaaga ggttcttttt tatcttggcc     480
agtatattat gactaaacga ttatatgatg agaagcaaca acatattgta tattgttcaa     540
atgatcttct aggagatttg tttggcgtgc caagcttctc tgtgaaagag cacaggaaaa     600
tatataccat gatctacagg aacttggtag tagtcaatca gcaggaatca tcggactcag     660
gtacatctgt gagtgagaac aggtgtcacc ttgaaggtgg gagtgatcaa aaggaccttg     720
tacaagagct tcaggaagag aaaccttcat cttcacattt ggtttctaga ccatctacct     780
catctagaag gagagcaatt agtgagacag aagaaaattc agatgaatta tctggtgaac     840
gacaaagaaa acgccacaaa tctgatagta tttcccttc ctttgatgaa agcctggctc     900
tgtgtgtaat aagggagata tgttgtgaaa gaagcagtag cagtgaatct acagggacgc     960
catcgaatcc ggatcttgat gctggtgtaa gtgaacattc aggtgattgg ttggatcagg    1020
attcagtttc agatcagttt agtgtagaat ttgaagttga atctctcgac tcagaagatt    1080
atagccttag tgaagaagga caagaactct cagatgaaga tgatgaggta tatcaagtta    1140
ctgtgtatca ggcaggggag agtgatacag attcatttga agaagatcct gaaatttcct    1200
tagctgacta ttggaaatgc acttcatgca atgaaatgaa tcccccctt ccatcacatt    1260 gcaacagatg ttgggcccct cgtgagaatt ggcttcctga agataaaggg aaagataaag    1320
gggaaatctc tgagaaagcc aaactggaaa actcaacaca agctgaagag ggctttgatg    1380 ttccctgattg taaaaaaact atagtgaatg attccagaga gtcatgtgtt gaggaaaatg    1440
atgataaaat tacacaagct tcacaatcac aagaaagtga agactattct cagccatcaa    1500
cttctagtag cattatttat agcagccaag aagatgtgaa agagtttgaa agggaagaaa    1560
cccaagacaa agaagagagt gtggaatcta gtttgccct taatgccatt gaaccttgtg    1620
tgatttgtca aggtcgacct aaaaatggtt gcattgtcca tggcaaaaca ggacatctta    1680
tggcctgctt tacatgtgca aagaagctaa agaaaaggaa taagccctgc ccagtatgta    1740
```

```
gacaaccaat tcaaatgatt gtgctaactt atttccccta gttgacctgt ctataagaga    1800
attatatatt tctaactata taaccctagg aatttagaca acctgaaatt tattcacata    1860
tatcaaagtg agaaaatgcc tcaattcaca tagatttctt ctctttagta taattgacct    1920
actttggtag tggaatagtg aatacttact ataaatttgac ttgaatatgt agctcatcct   1980
ttacaccaac tcctaatttt aaataaatttc tactctgtct taaatgagaa gtacttggtt   2040
tttttttttc ttaaatatgt atatgacatt taaatgtaac ttattatttt ttttgagacc    2100
gagtcttgct ctgttaccca ggctggagtg cagtggcgtg atcttggctc actgcaagct    2160
ctgcctcccg ggttcgcacc attctcctgc ctcagcctcc caattagctt ggcctacagt    2220
catctgccac cacacctggc tattttttg tactttagt agagacaggg tttcaccgtg      2280
ttagccagga tggtctcgat ctcctgacct cgtgatccgc ccacctcggc ctcccaaagt    2340
gctgggatta caggcatgag ccaccgcgtc cggcctaaat gtcacttagt acctttgata    2400
taaagagaaa atgtgtgaaa gatttagttt tttgttttt tgtttgtttg tttgtttgtt    2460
tgttttgaga tgagtctctc tgtcgcccag gctggagtgc agtgtcatga tctagcagtc    2520
tccgcttccc gggttcaagc cattctcctg gctcagcctc tggagcagct gggattacag    2580
gcatgcacca ccatgcccag ctaattttg tatttttagt agagataggg tttcaccatg     2640
ttggccaggc tggtcacgaa ctcctgacct caagtgaggt cacccgcctc ggcctcccga    2700
agtgctggga ttgcagatgt gagccaccat gtccagccaa gaattagtat ttaaatttta    2760
gatactcttt tttttttttt ttttttttt tttgagaca gagtcttgct ccatcaccca    2820
tgctagagtg cagtggagtg atctcggctc actgcaactt ccgccttctg ggttcaagct    2880
attctcctgc ctcagccttc caagtaactg ggattacagg catgtaccac cataccagct    2940
gatttttttg tatttttagt aaagacaggg tttcaccatg ttagccaggc tgatcttgaa    3000
ctcctaaact caagtgatct actcacctca gcctcccaaa atgctgggat tacagatgtg    3060
aggcacctgg cctcagattt tgatactct taaaccttct gatccttagt ttctctctcc     3120
aaaatactct ttctaggtta aaaaaaaaaa ggctcttata tttggtgcta tgtaaatgaa    3180
aatgtttttt aggttttctt gatttaacaa tagagacagg gtctccctgt gttgcccagg    3240
ctggtctcga actcctgggc tcaagagatc ctcctgtctt ggcctcgcaa agtgctaagt    3300
aggattacag gcgttagcca ccacacccgg ctgtaaaaat gtacttattc tccagcctct    3360
tttgtataaa ccatagtaag ggatgggagt aatgatgtta tctgtgaaaa tagccaccat    3420 ttaccccgtaa gacaaaactt gttaaagcct cctgagtcta acctagatta catcaggccc   3480 ttttttcacac acaaaaaaat cctttatggg atttaatgga atctgttgtt tcccctaag    3540 ttgaaaaaca actctaagac actttaaagt accttcttgg cctgggttac atggttccca    3600
gcctaggttt cagactttg cttaaggcca gttttagaaa cccgtgaatt cagaaaagtt     3660
aattcagaaa tttgataaac agaattgtta tttaaaaact aactgaaaag attgttaagt    3720
tctttctgaa ttattcagaa attatgcatc attttccttc aagaatgaca gggtcagcat    3780
gtggaattcc aagatacctc ttgacttcct ctcaagctcc gtgtttggtc agtggaggcc    3840
catccgagct cagcactgag aagtgttagt ttctttggga cccatctacc ctgaccacat    3900
catgatgttc atctgcagct gttgcaaggt gttcagattg tataaacata aatgtcacaa    3960
aaactttaaa agaagtgcaa ttctcaaaag gttaggtgga ctaaagcatt ctgtaaagca    4020
actgctaata atgagcttac agtggatttg aatttgaaaa atatagtaac aagcctgtca    4080
```

```
aatatctgca agaactatgg aataaaacta ctgatgcagt gaagacagtt gaaaagatca   4140
aacaaatgcc aagctatatt tataatgaac aaattcaaga aaaaggacta cggaaagttc   4200
aggacatcaa agaagtcagg caaaactcat cttgacccct gttgcaggca aaggaacgca   4260
gctggaagaa aagatgatat aacagttaac aggatgcaga catggcagag gtttcctaaa   4320
aatctcatta tctataacca tttctatatt tacatttgaa aatctccttt ggagacttag   4380
aacctctaaa ttattgactt attttttata taaggtcact ccgatgaaag gtgattacaa   4440
aatcatctac attgctgtct acaaaacaga taatatggat gtttgatcgc atctcattgt   4500
taactcttta ctgatatgtt tgtaaataca gaagtgaaat gtggacataa atagttacg    4560 ctatttggtt aatggtacta gacaacatgt aattaatgac attcaaaaat ttatggctag   4620
tgatatatat aaagtaaaat tttctttgca gtaaaatatg ccctttatta tagaagggag   4680
gatataagga accaacagtt tgtatgaaaa tagctcaaat aatatctttt attttgattt   4740
taatatttct tattttggtt tattagtgtc ttagaacaaa atggccttat ataatgaagc   4800
ctagttatgc tggactgttt tgatctcttt taattgttct gacagatagt tggggatgag   4860
agccgaataa ggtttgcctg aaataactga cactatataa tttctgcttt ggcaaatact   4920
aagttctaac ttgtcattcc tggtagaaca agcttttattt ttcgagccta gcaatgatct   4980
agaagcagat gttatctcag tgccttttgc aatttgttgt gtgggttttt ttttttttaa   5040
agccacacaa taattttgga aaacaatgta tgggtagaac atgtgtctgt taattgcaca   5100
caaaaccact tttaatgggt acagagttaa atttgaagga ataagttcta gctgaagtat   5160
tatgaactcc aaataatgct ttgaggacct ccaaaggtaa aagtactaat ccctttggcc   5220
atttattgag agagagagag agagagagta gggtgactat agttaatgta ttgaatgttc   5280
ttgctacaaa taaatgatat ttgagctgat gggtgtgcta attacactga tttgatcaat   5340
acccattgta tgtgaaacag tacatacacc atatttacaa ttatgtattt aacatttaaa   5400
atttctaata taagtatctc tcaaactgtg gattaacttc ttgatttata tttaaatatg   5460
aatcttaagc aaaacagtga aaataaccat cttgatttag tgtttttctc ccatatgtga   5520
attgtatata cttaggtgaa gacaataaaa tcaactgaac tgtaagctta gaataggact   5580
gaggtaattc tgcacagcaa ctttactaat ggtacattgt tgcttcaaaa ctctctctct   5640
ctctctctgt ctgtctcaat aaatggccaa agggattagt agtttacctg tggaggtcct   5700
ccaagcatta tttggagttg ataatacttc agctacaacc aagcagaatc tctttttttt   5760
ggaggtcctc gaagcattat ttggagttga taatacttca gcttcaattt ggagttgata   5820
atatttcagc tagaacctag tagaatctgt ttttttcctt tggaggtcct caaagcatta   5880
ttggagttca taatactgaa gctagaacca agcagaatct gttttttttct gaggagtatc   5940 ggtagcataa atgtgattat aaacatagta cacttgatat atggaggcag tgacagctat   6000
ttttacaaaa tttaaatctg caaatggatt caacatgttt atgggttatt aaaattgtct   6060
gatttcttag gttctttata gtacacgtgt tgaaaataaa tgattaagaa ttgtttcaag   6120
aatgcaatta tttgatctta aattttatg agttgttaaa atagaaatta tttgaatatc    6180
atatatttgg gtaacaaaag gcacaagtct gaatgtgttt cttttctgg aatggccatg    6240 cctgcccact ttagaaatac aaatatcact gggcagcttg aagcagttgg gagcctccaa   6300
tgagagcaac ttgagagaat gatgttgcaa gttagtagga gtaagaaatg ctgtgttctc   6360
cctgtcttct cttaggtcac atggcagcct ggcctaagtg atcgtgaatg gtctataagg   6420
gaggtagctg ggacagggag gggagtttgg gctagccacc gtaccacttg tcagcgtgaa   6480
```

```
aagtaagatt gtaattgcct gtttagtttt ctgcctcatc tttgaaagtt ccaccaagct    6540
gggaacctct tgattgtgag gcacaaatgt aagtacatca gaaaaaaaca aaaaaactgg    6600
ctttaaagca ggagcttgtg ggcccctaag ccagacgggg actagctttt ggcattatat    6660
aattaagatt ttttaaatcc ttaataaggg ttttattta tttttattta ttttttgaga    6720
cggagtcttg ctctgtggct caggctggag tacagtggtg caatcttggc tcactgcaac    6780
ctctgcctcc tggctgtgtt caagtggttc tgcttcagcc tcccaagtag ctggggttag    6840
agcaccctgt caccacgccc cgctaatttt tgtatttcta gcagagatga agtttcacta    6900
tgttggccag gctgggctca aactcctgac ctcaagtgat ctgcccgcct tggcccccca    6960
aagtgctgtg attacaggcg tgagccgcca cgcccagcct aataagggtt ttaaagataa    7020
ttagtgtgta ggtctgtagg cttatgatgg taaccacaag ttgttaatgg cattgtgaaa    7080 agttttagt tgcgctttat gggtggatgc tgaattacat tttgatttga tacttataaa    7140 aagaaaagt atttcttcag cttaaaaaat tgtttaaaag tttgtgatca tattgtctac    7200
catgtagcca gctttcaatt atatgtaaga gggactttt gacatttaca aataatactt    7260
tgaggtagat atctgaaagc accagcactt ggaaggtgtt cagaagtaac aaattataaa    7320
atgagctaac aaacgaaagg caaaataaaa ccgtaaagca agcagatggg aggcgtgttc    7380
agtaacttat tcataatgca tctgaaatga ttgctgtact caaatattta acgttagagt    7440
aatagtattt tgaatgaaaa ccatagttga tt                                 7472
```

<210> SEQ ID NO 2
<211> LENGTH: 497
<212> TYPE: PRT
<213> ORGANISM: Homo sapiens

<400> SEQUENCE: 2

```
Met Val Arg Ser Arg Gln Met Cys Asn Thr Asn Met Ser Val Pro Thr
1               5                   10                  15

Asp Gly Ala Val Thr Thr Ser Gln Ile Pro Ala Ser Glu Gln Glu Thr
            20                  25                  30

Leu Val Arg Pro Lys Pro Leu Leu Leu Lys Leu Leu Lys Ser Val Gly
        35                  40                  45

Ala Gln Lys Asp Thr Tyr Thr Met Lys Glu Val Leu Phe Tyr Leu Gly
    50                  55                  60

Gln Tyr Ile Met Thr Lys Arg Leu Tyr Asp Glu Lys Gln Gln His Ile
65                  70                  75                  80

Val Tyr Cys Ser Asn Asp Leu Leu Gly Asp Leu Phe Gly Val Pro Ser
                85                  90                  95

Phe Ser Val Lys Glu His Arg Lys Ile Tyr Thr Met Ile Tyr Arg Asn
            100                 105                 110

Leu Val Val Val Asn Gln Gln Glu Ser Ser Asp Ser Gly Thr Ser Val
        115                 120                 125

Ser Glu Asn Arg Cys His Leu Glu Gly Gly Ser Asp Gln Lys Asp Leu
    130                 135                 140

Val Gln Glu Leu Gln Glu Glu Lys Pro Ser Ser His Leu Val Ser
145                 150                 155                 160

Arg Pro Ser Thr Ser Ser Arg Arg Arg Ala Ile Ser Glu Thr Glu Glu
                165                 170                 175

Asn Ser Asp Glu Leu Ser Gly Glu Arg Gln Arg Lys Arg His Lys Ser
            180                 185                 190
```

```
Asp Ser Ile Ser Leu Ser Phe Asp Glu Ser Leu Ala Leu Cys Val Ile
            195                 200                 205

Arg Glu Ile Cys Cys Glu Arg Ser Ser Ser Glu Ser Thr Gly Thr
210                 215                 220

Pro Ser Asn Pro Asp Leu Asp Ala Gly Val Ser Glu His Ser Gly Asp
225                 230                 235                 240

Trp Leu Asp Gln Asp Ser Val Ser Asp Gln Phe Ser Val Glu Phe Glu
            245                 250                 255

Val Glu Ser Leu Asp Ser Glu Asp Tyr Ser Leu Ser Glu Glu Gly Gln
            260                 265                 270

Glu Leu Ser Asp Glu Asp Asp Glu Val Tyr Gln Val Thr Val Tyr Gln
            275                 280                 285

Ala Gly Glu Ser Asp Thr Asp Ser Phe Glu Glu Asp Pro Glu Ile Ser
290                 295                 300

Leu Ala Asp Tyr Trp Lys Cys Thr Ser Cys Asn Glu Met Asn Pro Pro
305                 310                 315                 320

Leu Pro Ser His Cys Asn Arg Cys Trp Ala Leu Arg Glu Asn Trp Leu
            325                 330                 335

Pro Glu Asp Lys Gly Lys Asp Lys Gly Glu Ile Ser Glu Lys Ala Lys
            340                 345                 350

Leu Glu Asn Ser Thr Gln Ala Glu Glu Gly Phe Asp Val Pro Asp Cys
            355                 360                 365

Lys Lys Thr Ile Val Asn Asp Ser Arg Glu Ser Cys Val Glu Glu Asn
370                 375                 380

Asp Asp Lys Ile Thr Gln Ala Ser Gln Ser Gln Glu Ser Glu Asp Tyr
385                 390                 395                 400

Ser Gln Pro Ser Thr Ser Ser Ser Ile Ile Tyr Ser Ser Gln Glu Asp
            405                 410                 415

Val Lys Glu Phe Glu Arg Glu Glu Thr Gln Asp Lys Glu Glu Ser Val
            420                 425                 430

Glu Ser Ser Leu Pro Leu Asn Ala Ile Glu Pro Cys Val Ile Cys Gln
            435                 440                 445

Gly Arg Pro Lys Asn Gly Cys Ile Val His Gly Lys Thr Gly His Leu
450                 455                 460

Met Ala Cys Phe Thr Cys Ala Lys Lys Leu Lys Lys Arg Asn Lys Pro
465                 470                 475                 480

Cys Pro Val Cys Arg Gln Pro Ile Gln Met Ile Val Leu Thr Tyr Phe
            485                 490                 495

Pro

<210> SEQ ID NO 3
<211> LENGTH: 2175
<212> TYPE: DNA
<213> ORGANISM: Homo sapiens

<400> SEQUENCE: 3
gttgtatatc agggccgcgc tgagctgcgc cagctgaggt gtgagcagct gccgaagtca      60
gttccttgtg gagccggagc tgggcgcgga ttcgccgagg caccgaggca ctcagaggag     120
gcgccatgtc agaaccggct gggatgtcc gtcagaaccc atgcggcagc aaggcctgcc     180
gccgcctctt cggcccagtg gacagcgagc agctgagccg cgactgtgat cgctaatgg      240 cgggctgcat ccaggaggcc cgtgagcgat ggaacttcga cttttgtcacc gagacaccac    300 tggagggtga cttcgcctgg gagcgtgtgc ggggccttgg cctgcccaag ctctaccttc    360
```

```
ccacggggcc ccggcgaggc cgggatgagt tgggaggagg caggcggcct ggcacctcac    420
ctgctctgct gcaggggaca gcagaggaag accatgtgga cctgtcactg tcttgtaccc    480
ttgtgcctcg ctcaggggag caggctgaag gtccccagg tggacctgga gactctcagg     540
gtcgaaaacg gcggcagacc agcatgacag atttctacca ctccaaacgc cggctgatct    600
tctccaagag gaagccctaa tccgcccaca ggaagcctgc agtcctggaa gcgcgagggc    660
ctcaaaggcc cgctctacat cttctgcctt agtctcagtt tgtgtgtctt aattattatt    720
tgtgttttaa tttaaacacc tcctcatgta catacctgg ccgcccctg cccccagcc       780
tctggcatta gaattattta aacaaaaact aggcggttga atgagaggtt cctaagagtg    840
ctgggcattt ttattttatg aaatactatt taaagcctcc tcatcccgtg ttctcctttt    900
cctctctccc ggaggttggg tgggccggct tcatgccagc tacttcctcc tccccacttg    960
tccgctgggt ggtaccctct ggaggggtgt ggctccttcc catcgctgtc acaggcggtt    1020
atgaaattca cccccttccc tggacactca gacctgaatt cttttttcatt tgagaagtaa   1080
acagatggca ctttgaaggg gcctcaccga gtggggcat catcaaaaac tttggagtcc     1140
cctcacctcc tctaaggttg gcagggtga ccctgaagtg agcacagcct agggctgagc     1200
tggggacctg gtaccctcct ggctcttgat accccctct gtcttgtgaa ggcaggggga     1260
aggtggggtc ctggagcaga ccaccccgcc tgccctcatg gcccctctga cctgcactgg   1320
ggagcccgtc tcagtgttga gccttttccc tctttggctc ccctgtacct tttgaggagc   1380
cccagctacc cttcttctcc agctgggctc tgcaattccc ctctgctgct gtccctcccc   1440
cttgtccttt cccttcagta ccctctcagc tccaggtggc tctgaggtgc ctgtcccacc   1500
cccaccccca gctcaatgga ctggaagggg aagggacaca caagaagaag ggcaccctag   1560
ttctacctca ggcagctcaa gcagcgaccg ccccctcctc tagctgtggg ggtgagggtc   1620
ccatgtggtg gcacaggccc ccttgagtgg ggttatctct gtgttagggg tatatgatgg   1680
gggagtagat ctttctagga gggagacact ggccccctcaa atcgtccagc gaccttcctc   1740
atccacccca tccctcccca gttcattgca ctttgattag cagcggaaca aggagtcaga   1800
cattttaaga tggtggcagt agaggctatg gacagggcat gccacgtggg ctcatatggg   1860
gctgggagta gttgtctttc ctggcactaa cgttgagccc ctggaggcac tgaagtgctt   1920
agtgtacttg gagtattggg gtctgacccc aaacaccttc cagctcctgt aacatactgg   1980
cctggactgt tttctctcgg ctccccatgt gtcctggttc ccgtttctcc acctagactg   2040
taaacctctc gagggcaggg accacaccct gtactgttct gtgtctttca cagctcctcc   2100
cacaatgctg aatatacagc aggtgctcaa taaatgattc ttagtgactt tacttgtaaa   2160
aaaaaaaaaa aaaaa                                                     2175
```

<210> SEQ ID NO 4
<211> LENGTH: 164
<212> TYPE: PRT
<213> ORGANISM: Homo sapiens

<400> SEQUENCE: 4

```
Met Ser Glu Pro Ala Gly Asp Val Arg Gln Asn Pro Cys Gly Ser Lys
1               5                   10                  15

Ala Cys Arg Arg Leu Phe Gly Pro Val Asp Ser Glu Gln Leu Ser Arg
            20                  25                  30

Asp Cys Asp Ala Leu Met Ala Gly Cys Ile Gln Glu Ala Arg Glu Arg
        35                  40                  45
```

```
Trp Asn Phe Asp Phe Val Thr Glu Thr Pro Leu Glu Gly Asp Phe Ala
 50                  55                  60
Trp Glu Arg Val Arg Gly Leu Gly Leu Pro Lys Leu Tyr Leu Pro Thr
 65                  70                  75                  80
Gly Pro Arg Arg Gly Arg Asp Glu Leu Gly Gly Gly Arg Arg Pro Gly
                 85                  90                  95
Thr Ser Pro Ala Leu Leu Gln Gly Thr Ala Glu Glu Asp His Val Asp
                100                 105                 110
Leu Ser Leu Ser Cys Thr Leu Val Pro Arg Ser Gly Glu Gln Ala Glu
                115                 120                 125
Gly Ser Pro Gly Gly Pro Gly Asp Ser Gln Gly Arg Lys Arg Arg Gln
            130                 135                 140
Thr Ser Met Thr Asp Phe Tyr His Ser Lys Arg Arg Leu Ile Phe Ser
145                 150                 155                 160
Lys Arg Lys Pro
```

<210> SEQ ID NO 5
<211> LENGTH: 8995
<212> TYPE: DNA
<213> ORGANISM: Homo sapiens

<400> SEQUENCE: 5

| | | | | | |
|---|---|---|---|---|---|
| gcagtggcga | cgccgagccg | gcgccctcag | tctcctcctc | caccgcctcc | cggttccgca    60 |
| gtcacttcct | gcagctgttt | ccctgtgggt | cgggttggac | tgactttga | cagtcagcct   120 |
| tcggctgcgg | aggggggctcg | gcggcggccg | gcggagaaag | ttgctccgag | aagaggctgg   180 |
| gtcgagctgg | gccgagccgg | gcgcgcaggg | cgggcgtcgc | gggcgtcccg | ggcggacgcg   240 |
| gcgcggagac | tgccggcgcg | tcccgggggt | tccgatttga | agaccttgct | tctcatcacc   300 |
| cactggatta | tgcccaggc | ttccctaccc | aatgatcctc | ttgcaacacg | ccgtgcttcc   360 |
| tccacctaag | cagccctcac | cctcgcctcc | tatgtcagtg | gccaccaggt | ctacaggaac   420 |
| cttgcagctt | ccaccacaga | agccttttgg | gcaggaggct | tccttgcctc | ttgcagggga   480 |
| agaagagtta | tcgaagggag | gggagcaaga | ctgtgccctg | gaggagctat | gtaagcccct   540 |
| gtactgcaaa | ctctgcaatg | tcaccttgaa | ctctgcacag | caagcccagg | ctcattatca   600 |
| gggtaaaaat | catggtaaga | aactccgaaa | ttactatgca | gcaaatagct | gtcctcctcc   660 |
| tgctagaatg | agcaatgtgg | tcgagcctgc | agctactcca | gttgttccag | tcctccgca   720 |
| gatgggctcc | tttaagccag | gaggccgagt | gatcctggcc | acggagaatg | attactgtaa   780 |
| gctctgtgat | gcctccttca | gttccccagc | tgtggctcag | gctcactatc | aagggaagaa   840 |
| tcatgccaag | aggctgcggc | tggcggaagc | tcagagtaac | tcattctcgg | aatcctcaga   900 |
| gctgggtcaa | cggcgggcca | ggaaagaagg | gaatgagttt | aagatgatgc | ctaacaggag   960 |
| aaatatgtat | acagtacaga | ataattcagc | aggtccttac | ttcaatcccc | gctctcggca  1020 |
| gagaattcca | cgtgatctgg | ccatgtgtgt | tactccaagt | ggccagtttt | actgctcaat  1080 |
| gtgtaatgtt | ggagctggcg | aagagatgga | attccggcag | catttagaga | gcaagcaaca  1140 |
| taagagcaag | gtgtctgaac | agcggtacag | gaatgagatg | gagaatctgg | gatatgtata  1200 |
| gtgattatca | tattaagata | gagcagcttt | tcctgcctgt | tgtttgcctt | ttgtcaactt  1260 |
| gccctgcttt | gtggtctttt | tgatatgagt | acattcctct | gcttaatgtt | aatacatgta  1320 |
| acccacagtg | gtaccatgag | atgtcaaaac | ctgggggccc | gggggcgggg | cggggggagg  1380 |
| tgggtgtgaa | gaacgtgctt | cttaggtcat | aacgcttttg | cagggtcaat | ggtgttgagc  1440 |

```
cgctcatagc atgtgaccta cctaccccat cagaaataac ttttatctt gctcaagttc    1500 tggtcaacta gtagcctgac ggcttagaac tttgactatt taaagtttc attttctttt    1560 gcaattttag ttttatgtac tgttaaagaa ttgtactgaa ttcttttag atcacagtaa    1620 aaataggttg gcagagattt cagtttccca gggcttaacc agaaccgcca cctcaatgca    1680
ttgtcagtag aatacattat tagaaactgt taaggtcttt cccgggacat ttttttctgc    1740
cattttcttt tgcaattgta gttttatgta ctgttaaaga attgtattga attcttttta    1800
gatcaaagta aaaataggtc agcagagatt tcagtttccc agggcttaac cagaaccgcc    1860
acctcaatgc attgtcagta ggatacatta ttagaaactg ttagggtctt tcccaggaca    1920
tttttttttc tgtatcatgt ctccccatca ttgaagcgca aatttcttg aattcaaata    1980 ctcccaatga gcttgtatac ttccaaacag ctaaacttga tttccagttg tggatttcac    2040
acatataatt gccgccttct tccctcctct ttttccccc ctagttgaat cagcttgtct    2100
aacaagccca ttttcatgcc ccagctgtgc tgtgggtttt ccaagcctca tatttgaata    2160
ttcaatgagt ttaagatgga tatgatttca aaaaataggg ccgggcgcgg tggctcacgc    2220
ctgtaatccc agcactttgg gaggccgaag caggcggatc acgaggtcag gaggtcgaga    2280
tcatcctggc taacacagtg aaaccccatc tctactaaaa atacaaaaca ttagccgggc    2340
gtggtggtgg gtgcctgtag tcccagctac tctggaggct gaggcaggag aatggcgtga    2400
acccgggagg cggagcttgc agtgagccga gatcgcgcca ctgcactcca gcctgggtga    2460
cagagcgaga ctccgtctca aaaaaaaaaa aaaaaaaaa aaaaaatat atatatatat    2520 agatatattt tccagcagtt tttaggaaac aaaggtgtgt ttgattttcc aatttagagt    2580
tacttcattg atagtaacat gcgcttatat catgatctaa accataagtt cagattgctt    2640 gatatttgt tttgccagac ttttttgata atctgattct tacggtttac ttacattttc    2700
ctctgtcttg ccagtctggt ggccatcctg aaaaatatca ccacctgctg ttttatacac    2760
agaggaattt ttaaaaagc aaataaagtt tcactatctt cgtttccagt agaaatatac    2820
acgaactatg gttttattct ttgtaattcg gctttcttga agatactaac aagtatatga    2880
tagatcactt tggcatctga taattatatc agtattatta ttttttgttt tttgcgttta    2940
aaataagaag ttgtatgaac ccaggaggtg gaggttgcag tcagccaaga atcgtgccac    3000
tgcactccag tctgggcgac agagcaatac tccgtctcca aaaaaaaaaa aaagaagct    3060 ataatatata tctagattaa ctaatggagt gctctgtgaa tattcattaa ctacatttta    3120
tctatttact atatttata tgggtaagac cagtggtcat ccgtatttct tttgaaagcc    3180
cacttgatca ggaagtttat attttaagca gtatgtttgc acaatggtca gttcacattt    3240
gattgcttgt attactaatt agaggtaaaa cttctatttt ttcttgataa ttctgtaggc    3300
aaaaaaaatt ggggaaggca aattacaatc attcttcttc tgtaatactt tgggacaatt    3360
tttaaacaac tcagacccat gtttaaaaac gagttttgtg tgattaaccc ttgtatagta    3420
tccagttact gtcttctctt gaagtggtgg ttctttgaga agtagaatta ttttgtaact    3480
tttcttctcc cagaaacaga agaatcaaat actattctgt taggattcta tctagacctg    3540
tgactcttag tataataacc ctttattat tattattatt attatttttt cagtaatcta    3600
taaagtagag ttgcttagtt ttgagcaatt tagggctttt cttattggcc agtaggttat    3660
tcattttgct gctaaatata atttttttggt taatttaac attatagtgc tggccgcttg    3720
gttctatgat tacctaaaaa tctagttttt ttcctccata ggtagatgtg tgtgtatgca    3780 taccccccaca cacacacgta catatatgtt gtcatagaga ggtatttcaa cccttatttc    3840
```

```
aaataacagt agaagatacg aacatgaatt tatattttgt aaaaatgtca ttcatccact    3900
ttgttttcca ttggaaatag ttttataaga agggttcccc ttgctctctc cacttaacaa    3960
tttcattata tacgtagaaa aagcagccga cttaagggct tgatgttttt tcaggccttg    4020
tggattcagg tttccagttt cccagtgccc ttaatggatg ttatgaatgc ataagcacat    4080
tttcttttaa agaaagaagt tagatttata gtgttatttc ttacttgcta tatttctttg    4140
cactaaaaaa gagctatgtg tttgttttat aggcacttt agtaccgtat tgcctacaat      4200
aactcagttt gctccttaaa ttccaaactc tgggaagttg ataaataact tccatgatca    4260
cttgtaaaag ttacatgcac atctgaaaaa aaatcacaaa tctctatgac agtaggttat    4320
gttttgagct tgttaccttg cagtattctt ctctgttcca taggtgaaaa caaagggtga    4380
cagaggttat caggcaggaa atgcctaaat agatacatct ctgcatggta caatttctca    4440
tattcatgta ttccataaac agtgtttttt ctctgtttaa gcagactgtt gtttcttctg    4500
agtcagtgat atgtgatctt cgttggtttc attttgtgaa gctcagtctg tctctgtaac    4560
atactttagg atttgcacct tgtgctcccc aggaattatg ttagtgtcct tttctatgct    4620
gtcttcaagg atggacagag gcctaaacca caacaacaac aaaaattaga aaaaaaata     4680
cttagatttc ggtaatcatc cataggaact catagcatca gtctcttttc tctgtgaata    4740
atatctttgt gtaagttgtc ataaaaaatc aacgttagaa gatgacaatt agaattcttc    4800
ttaggtattg agggtaagaa gttgtaaaga aagaaaattc gtgtttcaac taaaagattg    4860
gattgcatat acctttgaag tggttttgta aaaaaagttc agttactaaa ctgagtgtgc    4920
cctgtaatcc ttttgagtgc actgaagatg ctttgaaaat actttgttgg tcttcacatt    4980
gtgcatcatg tcctgcaact tgtaaatatg tgcatgttgt ttatgtttgt ctgcctgtct    5040
cttattgcac taaattctgc aaggtgaata atttttttat accatttatt tggaaaaagt    5100
tcctcctcca actcttcttc actgaccttt taattagttg gtaaacttag aaaaccaggt    5160
aggattttg aagccctgag tttaaaagaa gaatcgtggc tatttgacat catccttaca    5220
ttccctgac ttaaaaagct aacaagaagc acgagatctt ccacctcatt ttagaaagct    5280
tttctacaga actatatgct tgcttatagc taccatctcta cagtttgaac agggagaaag    5340
ggagatatgt atgtctggtt acatcttcct tcactcttga attggctggg acagcaagca    5400
acaacagttt gaggtccagt gacctacgta aaatgagtgt cgtttgtgtc aggggacaca    5460
tgtaactgtg caacatggta ttttctacag ggagggctag aagggtggt tttggaacct     5520
aacctacttt gtgtcttcat tgtcagaact aaggttggaa atgccccttta aagaacttgg    5580
tgaggcatat gctaggacaa tagagctgct ttagaaagaa attgagacat gttttgtcag    5640
gacagataaa agtttaatgc aggcttttga acagatgttt taaaacaaat ttgaccttac    5700
caactatttt tttcttctag ccaaatcatt gtacaggagt ttcatatatg ataaaaagtg    5760
ttttgttatt gtttttgctt tcttggcagg ggagaacccc taccattgtg agcagttact    5820
gtcactctgg ctgaatggac aaatagctgt gtaaatagct tctcataaaa cgcttctact    5880
gatagctgtt tgacttttc ttcccgttat gaatgggagg aacatttgta aacttccttt    5940
ctgggtagct accaaaaaac gtactggctt atggtcccat gtgaccttgt ctccgttaag    6000
cccagaatct gagtgccttt agcaagtgtt agcatttcac agagagaaga gagacagaat    6060
tattgctatt aatcaccatt cataaatagg agcttggaat aacaaggtc tgtgtgaatt      6120
ctgttctacg tcttttttttt ccctttttta aataaatgtc aatttgatat caagtaaaac    6180
```

```
tattgtcatt attgatcaga accatacat tctgaaaatg aatccagttt tcccaagctg    6240
gcagaagtca gagatcattt ttcaccttga tctgtgttgc gtttgtactt agtgaatggc    6300
agtgtggttg attggaagag cttgacactg atgtttggaa aaattcttta ttctagtggt    6360
cattttcaaa cttgtcttct gtagagaggg gaaaaattat gtatttgcag ctaaagcgaa    6420
gagactggca caataattat taattgtgtt agttcatttc tatattaaat gaagcatctt    6480
cacaaatcag gtttgaagcc attaaaagca aatttttccc tagtttaatt aatttaaaat    6540
tctaaattgc ctgactactt agaatcttag aaacgccctg ctagactgat tttattatag    6600
aaatgttaac atgttcctca acattttctc aagaaaattt tcagacatat atcaaagttg    6660
aaaaaacttt gcagtataac cactgctaga ttctgccatc aacatttgac tatacttgta    6720
ttgccatgta tctgttcata ttctctatcc ctcttttcat ccatcgatcc atcagatttt    6780
ttttttaaag aacattccaa agtaaatttt aggcaataca ctgccctaaa ttcttagcat    6840
gggtgtcatt aattaaggtt tagtattcgt ttaaatatct attttgaaag tggtgtatga    6900
agttgataat ctgagccaat taacatactt ttttttttttt cctcctgtgg acttttgtct    6960
tccagtttct cttttttgtgt gtacttaggg tgagggagga caattccttt caaacacaag    7020
tttattttag aattggtcat ttttaagtgc ttgtcataaa ttttaaagtt tcaatataat    7080
ttttcttttc cccacttctg ataatgtatt tttgccaaac tatgcagctt cttcaaaaaa    7140
ctgtaaatta ctgattgggg tttatgaaat cagcgaatac ctcatttcaa tctgttgctg    7200
cttttctccc tcttgtcact tctccttttca ctactttcag ctgctctacc agaaggtaga    7260
ggggagtaaa gggtcaaacc cctatataat tagctgtttt aaacaactct aggagagcag    7320
attaagtagc ttagtaagtt gaaactatta attttttctaa agaatttgat ttgaattcct    7380
tgagaattgt aattatccac acttcctcca gctataatta gcagaattaa aaatgattgt    7440
actgtacaat gagttgttga aattgtaagc cttagtaacc atctttagct ttattgtagt    7500
catgttagga aaaaattatt tttacatatg cctttatttt tatgcccact ttttgtggat    7560
aagattcttt agataaaatc taaagaattt taagtgactt tctccaggtc atgaagattc    7620
aatgggtaga attgaatcag aattgaaatg ttccagattc atattcttgt gtgtgtttga    7680
taaaattcat ggcttccaaa gtaactgaac acttcctttg ggcccttgga gggaaaatcc    7740
atatttttac taattacact ttttttttta gacatctggc agttcttga acttaaacat    7800 attctcatgg ccatagttcc aaattaagcc cgacgcagtt gctaaaaatc ttgctgcact    7860
gttgaatact aataatgcaa catttattgg atgttttgtgc attttgatga ccttcatgat    7920
tcatttataa gtctttgtaa gtgcttaagt gaccccctca ctagtgaaaa taataaatgt    7980
tctatatcat ttattattat ttgtgtattc tctacatgat atattttttt aaggaagagt    8040
aactccacat gtcagaatga gtgatattat cctagggcaa agcgcaaata gggcagtttg    8100
tttctactct gcaaatatgg catgtatagg aacaaaactc ttttggagtg ctggtcatt    8160 gttctgccct cttttggtac ctgagtacct ttctggggtt ttgtaaatcg tgtgtcattt    8220
gtaagaattt cacgttaact ctgcgttact tggtgttcac ctgtggtatc cttgactgac    8280
cataatgatt tagtttgggt atgatgtgtc tgctttgaaa tgccttactg gagtatgtca    8340
gatcctgctt taaagcattc catatatctg ctgggacaat aagttgcttc tccttggaaa    8400
tatgctctag attcagaagc aaaaccgatt tgcttcac cattaaggtt gcattttaat    8460
gcagttattg ttttaaatta gagaataaaa tgtaaaacca agggaggctt tagaacccctt    8520 tattgaatgg catggcaaac ttttaaaaact gcttttgcta tttcactaga actatctttg    8580
```

```
ataaaggata tagctaaaaa atgtcagccc aaactgtgtg taattagggt tgtttattaa      8640
aattttctct aaatgtcata cagaggctta agatctgtgt atgctgttgg gtcggagtgc      8700
cagtcactgc tttggaagtc tgtgttctgg ggctgcagaa tgacaaacgt gtcatgggat      8760
taaaaccaat caactgtgaa ttgtgaaatt gaaactactc tttcggtttt attttcttta      8820
gcatattgag tatagaaatc tgaaacttat ttaaaattta tactgctttt gttgatggct      8880 catttggct gtgtatcctc acttatgtac tgatttctga taaaggcttg acattattat       8940
aacacgcatt ttgtgttcca gtttaataaa acggtttctg agtcttgtct gaaaa           8995
```

<210> SEQ ID NO 6
<211> LENGTH: 289
<212> TYPE: PRT
<213> ORGANISM: Homo sapiens

<400> SEQUENCE: 6

```
Met Ile Leu Leu Gln His Ala Val Leu Pro Pro Lys Gln Pro Ser
1               5                   10                  15

Pro Ser Pro Pro Met Ser Val Ala Thr Arg Ser Thr Gly Thr Leu Gln
                20                  25                  30

Leu Pro Pro Gln Lys Pro Phe Gly Gln Glu Ala Ser Leu Pro Leu Ala
            35                  40                  45

Gly Glu Glu Leu Ser Lys Gly Gly Glu Gln Asp Cys Ala Leu Glu
50                  55                  60

Glu Leu Cys Lys Pro Leu Tyr Cys Lys Leu Cys Asn Val Thr Leu Asn
65                  70                  75                  80

Ser Ala Gln Gln Ala Gln Ala His Tyr Gln Gly Lys Asn His Gly Lys
                85                  90                  95

Lys Leu Arg Asn Tyr Tyr Ala Ala Asn Ser Cys Pro Pro Ala Arg
            100                 105                 110

Met Ser Asn Val Val Glu Pro Ala Ala Thr Pro Val Val Pro Val Pro
        115                 120                 125

Pro Gln Met Gly Ser Phe Lys Pro Gly Gly Arg Val Ile Leu Ala Thr
    130                 135                 140

Glu Asn Asp Tyr Cys Lys Leu Cys Asp Ala Ser Phe Ser Ser Pro Ala
145                 150                 155                 160

Val Ala Gln Ala His Tyr Gln Gly Lys Asn His Ala Lys Arg Leu Arg
                165                 170                 175

Leu Ala Glu Ala Gln Ser Asn Ser Phe Ser Glu Ser Ser Glu Leu Gly
            180                 185                 190

Gln Arg Arg Ala Arg Lys Glu Gly Asn Glu Phe Lys Met Met Pro Asn
        195                 200                 205

Arg Arg Asn Met Tyr Thr Val Gln Asn Asn Ser Ala Gly Pro Tyr Phe
    210                 215                 220

Asn Pro Arg Ser Arg Gln Arg Ile Pro Arg Asp Leu Ala Met Cys Val
225                 230                 235                 240

Thr Pro Ser Gly Gln Phe Tyr Cys Ser Met Cys Asn Val Gly Ala Gly
                245                 250                 255

Glu Glu Met Glu Phe Arg Gln His Leu Glu Ser Lys Gln His Lys Ser
            260                 265                 270

Lys Val Ser Glu Gln Arg Tyr Arg Asn Glu Met Glu Asn Leu Gly Tyr
        275                 280                 285

Val
```

<210> SEQ ID NO 7
<211> LENGTH: 1870
<212> TYPE: DNA
<213> ORGANISM: Homo sapiens

<400> SEQUENCE: 7

```
ctccgagacg ggtggggccg gagctccaag ctggtttgaa caagccctgg gcatgtttgg      60
cgggaagttg gcttagctcg gctacctgtg gccccgcagt tttgtagtcc ccgccttgtt     120
tctccccaga ggcctctcaa tcctccctcc atgatcttcg catagagcac agtaccccct     180
cacacgagg acgcgatggc tcccaagaaa cgcccagaaa cccagaagac ctccgagatt     240
gtattacgcc ccaggaacaa gaggagcagg agtccctgg agctggagcc cgaggccaag     300
aagctctgtg cgaagggctc cggtcctagc agaagatgtg actcagactg cctctgggtg     360
gggctggctg gcccacagat cctgccacca tgccgcagca tcgtcaggac cctccaccag     420
cataagctgg gcagagcttc ctggccatct gtccagcagg gctccagca gtcctttttg      480
cacactctgg attcttaccg gatattacaa aaggctgccc cctttgacag gagggctaca     540
tccttggcgt ggcacccaac tcaccccagc accgtggctg tgggttccaa aggggagat     600
atcatgctct ggaattttgg catcaaggac aaacccacct tcatcaaagg gattggagct     660
ggagggagca tcactgggct gaagtttaac cctctcaata ccaaccagtt ttacgcctcc     720
tcaatggagg gaacaactag gctgcaagac tttaaaggca acattctacg agttttttgcc    780
agctcagaca ccatcaacat ctggttttgt agcctggatg tgtctgctag tagccgaatg     840
gtggtcacag agacaacgt ggggaacgtg atcctgctga acatggacgg caaagagctt     900
tggaatctca gaatgcacaa aaagaaagtg acgcatgtgg ccctgaaccc atgctgtgat     960
tggttcctgg ccacagcctc cgtagatcaa acagtgaaaa tttgggacct cgcccaggtt    1020
agagggaaag ccagcttcct ctactcgctg ccgcacaggc atcctgtcaa cgcagcttgt    1080
ttcagtcccg atggagcccg gctcctgacc acgaccagaa gagcgagat ccagagtttac    1140
tctgcttccc agtgggactg ccccctgggc ctgatcccgc accctcaccg tcacttccag    1200
cacctcacac ccatcaaggc agcctggcat cctcgctaca acctcattgt tgtgggccga    1260
taccccagatc ctaatttcaa agttgtacc ccttatgaat tgaggacgat cgacgtgttc    1320
gatggaaact cagggaagat gatgtgtcag ctctatgacc cagaatcttc tggcatcagt    1380
tcgcttaatg aattcaatcc catggggggac acgctggcct ctgcaatggg ttaccacatt    1440
ctcatctgga gccaggagga agccaggaca cggaagtgag agacactaaa gaaggtgtgg    1500
gccagacaag gccttggagc ccacacatgg gatcaagtcc tgcaagcaga ggtggcgatt    1560
tgttaaaggg ccaaaagtat ccaaggttag ggttggagca ggggtgctgg gacctggggc    1620
actgtgggac tgggacactt ttatgttaat gctctggact tgcctccaga gactgctcca    1680
gagttggtga cacagctgtc ccaagggccc ctctgtatct agcctggaac caaggttatc    1740
ttggaactaa atgactttc tcctctcagt gggtggtagc agagggatca agcagttatt    1800
tgatttgtgc tcacttttga tatggccaat aaaaccatac cgactgagaa aaaaaaaaa    1860
aaaaaaaaa                                                           1870
```

<210> SEQ ID NO 8
<211> LENGTH: 427
<212> TYPE: PRT
<213> ORGANISM: Homo sapiens

<400> SEQUENCE: 8

-continued

```
Met Ala Pro Lys Lys Arg Pro Glu Thr Gln Lys Thr Ser Glu Ile Val
1               5                   10                  15

Leu Arg Pro Arg Asn Lys Arg Ser Arg Ser Pro Leu Glu Leu Glu Pro
            20                  25                  30

Glu Ala Lys Lys Leu Cys Ala Lys Gly Ser Gly Pro Ser Arg Arg Cys
        35                  40                  45

Asp Ser Asp Cys Leu Trp Val Gly Leu Ala Gly Pro Gln Ile Leu Pro
    50                  55                  60

Pro Cys Arg Ser Ile Val Arg Thr Leu His Gln His Lys Leu Gly Arg
65                  70                  75                  80

Ala Ser Trp Pro Ser Val Gln Gln Gly Leu Gln Ser Phe Leu His
                85                  90                  95

Thr Leu Asp Ser Tyr Arg Ile Leu Gln Lys Ala Ala Pro Phe Asp Arg
            100                 105                 110

Arg Ala Thr Ser Leu Ala Trp His Pro Thr His Pro Ser Thr Val Ala
            115                 120                 125

Val Gly Ser Lys Gly Gly Asp Ile Met Leu Trp Asn Phe Gly Ile Lys
        130                 135                 140

Asp Lys Pro Thr Phe Ile Lys Gly Ile Gly Ala Gly Gly Ser Ile Thr
145                 150                 155                 160

Gly Leu Lys Phe Asn Pro Leu Asn Thr Asn Gln Phe Tyr Ala Ser Ser
            165                 170                 175

Met Glu Gly Thr Thr Arg Leu Gln Asp Phe Lys Gly Asn Ile Leu Arg
            180                 185                 190

Val Phe Ala Ser Ser Asp Thr Ile Asn Ile Trp Phe Cys Ser Leu Asp
        195                 200                 205

Val Ser Ala Ser Ser Arg Met Val Val Thr Gly Asp Asn Val Gly Asn
    210                 215                 220

Val Ile Leu Leu Asn Met Asp Gly Lys Glu Leu Trp Asn Leu Arg Met
225                 230                 235                 240

His Lys Lys Lys Val Thr His Val Ala Leu Asn Pro Cys Cys Asp Trp
            245                 250                 255

Phe Leu Ala Thr Ala Ser Val Asp Gln Thr Val Lys Ile Trp Asp Leu
            260                 265                 270

Arg Gln Val Arg Gly Lys Ala Ser Phe Leu Tyr Ser Leu Pro His Arg
        275                 280                 285

His Pro Val Asn Ala Ala Cys Phe Ser Pro Asp Gly Ala Arg Leu Leu
    290                 295                 300

Thr Thr Asp Gln Lys Ser Glu Ile Arg Val Tyr Ser Ala Ser Gln Trp
305                 310                 315                 320

Asp Cys Pro Leu Gly Leu Ile Pro His Pro His Arg His Phe Gln His
            325                 330                 335

Leu Thr Pro Ile Lys Ala Ala Trp His Pro Arg Tyr Asn Leu Ile Val
            340                 345                 350

Val Gly Arg Tyr Pro Asp Pro Asn Phe Lys Ser Cys Thr Pro Tyr Glu
        355                 360                 365

Leu Arg Thr Ile Asp Val Phe Asp Gly Asn Ser Gly Lys Met Met Cys
    370                 375                 380

Gln Leu Tyr Asp Pro Glu Ser Ser Gly Ile Ser Ser Leu Asn Glu Phe
385                 390                 395                 400

Asn Pro Met Gly Asp Thr Leu Ala Ser Ala Met Gly Tyr His Ile Leu
            405                 410                 415
```

Ile Trp Ser Gln Glu Glu Ala Arg Thr Arg Lys
         420                 425

<210> SEQ ID NO 9
<211> LENGTH: 1936
<212> TYPE: DNA
<213> ORGANISM: Homo sapiens

<400> SEQUENCE: 9

| | |
|---|---:|
| gcttgtgggc gggcccgggc aggagcgggc ttgccctgcg agcagtagc taggaacaga | 60 |
| tccacttgca ggttgctgtt cccagccatg gcttcgcgct gctggcgctg gtggggctgg | 120 |
| tcggcgtggc ctcggacccg gctgcctccc gccgggagca ccccgagctt ctgccaccat | 180 |
| ttctccacac aggagaagac cccccagatc tgtgtggtgg gcagtggccc agctggcttc | 240 |
| tacacggccc aacacctgct aaagcacccc caggcccacg tggacatcta cgagaaacag | 300 |
| cctgtgccct ttggcctggt gcgctttggt gtggcgcctg atcaccccga ggtgaagaat | 360 |
| gtcatcaaca catttaccca gacgcccat tctggccgct gtgccttctg gggcaacgtg | 420 |
| gaggtgggca gggacgtgac ggtgccggag ctgcggagg cctaccacgc tgtggtgctg | 480 |
| agctacgggg cagaggacca tcgggccctg gaaattcctg gtgaggagct gccaggtgtg | 540 |
| tgctccgccc gggccttcgt gggctggtac aacgggcttc ctgagaacca ggagctggag | 600 |
| ccagacctga gctgtgacac agccgtgatt ctggggcagg gaacgtggc tctggacgtg | 660 |
| gcccgcatcc tactgacccc acctgagcac ctggaggccc tccttttgtg ccagagaacg | 720 |
| gacatcacga aggcagccct gggtgtactg aggcagagtc gagtgaagac agtgtggcta | 780 |
| gtgggccggc gtggacccct gcaagtggcc ttcaccatta aggagcttcg ggagatgatt | 840 |
| cagttaccgg gagcccggcc cattttggat cctgtggatt tcttgggtct ccaggacaag | 900 |
| atcaaggagg tccccgccc gaggaagcgg ctgacggaac tgctgcttcg aacgccaca | 960 |
| gagaagccag gccggcgga agctgcccgc caggcatcgg cctcccgtgc ctggggcctc | 1020 |
| cgctttttcc gaagccccca gcaggtgctg ccctcaccag atgggcggcg ggcagcaggt | 1080 |
| gtccgcctag cagtcactag actggaggggt gtcgatgagg ccacccgtgc agtgcccacg | 1140 |
| ggagacatgg aagacctccc ttgtgggctg gtgctcagca gcattgggta taagagccgc | 1200 |
| cctgtcgacc caagcgtgcc cttttgactcc aagcttgggg tcatcccaa tgtggagggc | 1260 |
| cgggttatgg atgtgccagg cctctactgc agcggctggg tgaagagagg acctacaggt | 1320 |
| gtcatagcca caaccatgac tgacagcttc ctcaccggcc agatgctgct gcaggacctg | 1380 |
| aaggctgggt tgctccccctc tggccccagg cctggctacg cagccatcca ggccctgctc | 1440 |
| agcagccgag gggtccggcc agtctctttc tcagactggg agaagctgga tgccgaggag | 1500 |
| gtggcccggg gccagggcac gggggaagccc agggagaagc tggtggatcc tcaggagatg | 1560 |
| ctgcgcctcc tgggccactg agcccagccc cagccccggc ccccagcagg aagggatga | 1620 |
| gtgttgggag gggaagggct gggtccgtct gagtgggact ttgcacctct gctgatcccg | 1680 |
| gccggccctg gcttggaggc ttggctgctc ttccagcgtc tctcctccct cctggggaag | 1740 |
| gtcgcccttg cgcgcaaggt tttagctttc agcaactgag gtaaccttag gacaggtgg | 1800 |
| aggtgtgggc cgatctaacc ccttacccat ctctctactg ctggactgtg gagggtcacc | 1860 |
| aggttgggaa catgctggaa ataaaacagc tgcaaccaag aaaaaaaaaa aaaaaaaaaa | 1920 |
| aaaaaaaaa aaaaaa | 1936 |

<210> SEQ ID NO 10

```
<211> LENGTH: 497
<212> TYPE: PRT
<213> ORGANISM: Homo sapiens

<400> SEQUENCE: 10

Met Ala Ser Arg Cys Trp Arg Trp Trp Gly Trp Ser Ala Trp Pro Arg
1               5                   10                  15

Thr Arg Leu Pro Pro Ala Gly Ser Thr Pro Ser Phe Cys His His Phe
            20                  25                  30

Ser Thr Gln Glu Lys Thr Pro Gln Ile Cys Val Val Gly Ser Gly Pro
        35                  40                  45

Ala Gly Phe Tyr Thr Ala Gln His Leu Leu Lys His Pro Gln Ala His
    50                  55                  60

Val Asp Ile Tyr Glu Lys Gln Pro Val Pro Phe Gly Leu Val Arg Phe
65                  70                  75                  80

Gly Val Ala Pro Asp His Pro Glu Val Lys Asn Val Ile Asn Thr Phe
                85                  90                  95

Thr Gln Thr Ala His Ser Gly Arg Cys Ala Phe Trp Gly Asn Val Glu
            100                 105                 110

Val Gly Arg Asp Val Thr Val Pro Glu Leu Arg Glu Ala Tyr His Ala
        115                 120                 125

Val Val Leu Ser Tyr Gly Ala Glu Asp His Arg Ala Leu Glu Ile Pro
    130                 135                 140

Gly Glu Glu Leu Pro Gly Val Cys Ser Ala Arg Ala Phe Val Gly Trp
145                 150                 155                 160

Tyr Asn Gly Leu Pro Glu Asn Gln Glu Leu Glu Pro Asp Leu Ser Cys
                165                 170                 175

Asp Thr Ala Val Ile Leu Gly Gln Gly Asn Val Ala Leu Asp Val Ala
            180                 185                 190

Arg Ile Leu Leu Thr Pro Pro Glu His Leu Glu Ala Leu Leu Leu Cys
        195                 200                 205

Gln Arg Thr Asp Ile Thr Lys Ala Ala Leu Gly Val Leu Arg Gln Ser
    210                 215                 220

Arg Val Lys Thr Val Trp Leu Val Gly Arg Arg Gly Pro Leu Gln Val
225                 230                 235                 240

Ala Phe Thr Ile Lys Glu Leu Arg Glu Met Ile Gln Leu Pro Gly Ala
                245                 250                 255

Arg Pro Ile Leu Asp Pro Val Asp Phe Leu Gly Leu Gln Asp Lys Ile
            260                 265                 270

Lys Glu Val Pro Arg Pro Lys Arg Leu Thr Glu Leu Leu Leu Arg
    275                 280                 285

Thr Ala Thr Glu Lys Pro Gly Pro Ala Glu Ala Arg Gln Ala Ser
290                 295                 300

Ala Ser Arg Ala Trp Gly Leu Arg Phe Phe Arg Ser Pro Gln Gln Val
305                 310                 315                 320

Leu Pro Ser Pro Asp Gly Arg Arg Ala Ala Gly Val Arg Leu Ala Val
            325                 330                 335

Thr Arg Leu Glu Gly Val Asp Glu Ala Thr Arg Ala Val Pro Thr Gly
        340                 345                 350

Asp Met Glu Asp Leu Pro Cys Gly Leu Val Leu Ser Ser Ile Gly Tyr
    355                 360                 365

Lys Ser Arg Pro Val Asp Pro Ser Val Pro Phe Asp Ser Lys Leu Gly
370                 375                 380

Val Ile Pro Asn Val Glu Gly Arg Val Met Asp Val Pro Gly Leu Tyr
```

```
                385                 390                 395                 400
Cys Ser Gly Trp Val Lys Arg Gly Pro Thr Gly Val Ile Ala Thr Thr
                405                 410                 415

Met Thr Asp Ser Phe Leu Thr Gly Gln Met Leu Leu Gln Asp Leu Lys
                420                 425                 430

Ala Gly Leu Leu Pro Ser Gly Pro Arg Pro Gly Tyr Ala Ala Ile Gln
                435                 440                 445

Ala Leu Leu Ser Ser Arg Gly Val Arg Pro Val Ser Phe Ser Asp Trp
                450                 455                 460

Glu Lys Leu Asp Ala Glu Val Ala Arg Gly Gln Gly Thr Gly Lys
465                 470                 475                 480

Pro Arg Glu Lys Leu Val Asp Pro Gln Glu Met Leu Arg Leu Leu Gly
                485                 490                 495

His

<210> SEQ ID NO 11
<211> LENGTH: 1084
<212> TYPE: DNA
<213> ORGANISM: Homo sapiens

<400> SEQUENCE: 11
tagagcagac aagcccgccc cgccgctcct cccagcagct tctatcccgg aagttgatgc      60
cgagcgcaga tcgcttgcag cttgctagct gtgtgggctg ggaggtctgg tagggctgag    120
cttgcaagag gatcaacatg cctttggcta gagatttact acatccgtcc ttggaagagg    180
aaaagaaaaa acataaaaag aaacgcctag tacaaagtcc aaattcttac tttatggatg    240
taaaatgtcc aggttgctac aagatcacca cggttttcag ccatgctcag acagtggttc    300
tttgtgtagg ttgttcaaca gtgttgtgcc agcctacagg aggaaaggcc agactcacag    360
aagggtgttc atttagaaga agcaacact aatgattcaa acagcttcct gaattttaat     420
tttgtgttgt ctcacagaaa gccttatcat aaattccata attctaatta atttaccaag    480
ataatgtaat tacatttggt tttgtaaggt atacagcagt aatctcctat tttggtgtca    540
gtttttcaat aaagttttga ttatgggcaa atcccctctt tttctttttt taaaatatat    600
ttgagtatgc catacattta tatatatggt gtatatgaat ttggtttaaa catttaaaa    660 tttattctga ttagtttgtg tctttttttt ttttttttgag agagagagtc ctgctctgtc    720
actcaagctg gagtgcagtg gtgcgatctc ggctcactgc aacctccgcc tcccaggtcc    780
aagcaattct cttgccttgt cctcccaagt agctgggatt ataggcacac accaccatgc    840
ctggctaatt tgtgtctcat tttcaagagt agaaaccta aatattttat tttcattcct     900
tttccaaatt gctatgaatg ggattaaagg attacagatg taaagtctat tatttgtgaa    960
ttctaaatgt agttctgctg ttgtacctgt ggaaacatct taagaagta catattttgc    1020 acgtcctgca cgtgtacccc agaacttaaa ctataattaa aagaatagt ttcaaaaaaa    1080 taca                                                                 1084

<210> SEQ ID NO 12
<211> LENGTH: 84
<212> TYPE: PRT
<213> ORGANISM: Homo sapiens

<400> SEQUENCE: 12

Met Pro Leu Ala Arg Asp Leu Leu His Pro Ser Leu Glu Glu Glu Lys
1               5                   10                  15
```

```
Lys Lys His Lys Lys Arg Leu Val Gln Ser Pro Asn Ser Tyr Phe
            20                  25                  30

Met Asp Val Lys Cys Pro Gly Cys Tyr Lys Ile Thr Thr Val Phe Ser
        35                  40                  45

His Ala Gln Thr Val Val Leu Cys Val Gly Cys Ser Thr Val Leu Cys
    50                  55                  60

Gln Pro Thr Gly Gly Lys Ala Arg Leu Thr Glu Gly Cys Ser Phe Arg
65                  70                  75                  80

Arg Lys Gln His

<210> SEQ ID NO 13
<211> LENGTH: 891
<212> TYPE: DNA
<213> ORGANISM: Homo sapiens

<400> SEQUENCE: 13
tcacgtgacc cgggcgcgct gcggccgccc gcgcggaccc ggcgagaggc ggcggcggga      60
gcggcggtga tggacgggtc cggggagcag cccagaggcg ggggcccac cagctctgag     120 cagatcatga agacaggggc ccttttgctt cagggtttca tccaggatcg agcagggcga     180 atggggggg aggcacccga gctggccctg acccgtgtgc ctcaggatgc gtccaccaag     240
aagctgagcg agtgtctcaa gcgcatcggg gacgaactgg acagtaacat ggagctgcag     300
aggatgattg ccgccgtgga cacagactcc ccccgagagg tcttttttccg agtggcagct     360 gacatgtttt ctgacggcaa cttcaactgg ggccgggttg tcgcccttttt ctactttgcc     420 agcaaactgg tgctcaaggc cctgtgcacc aaggtgccgg aactgatcag aaccatcatg     480
ggctggacat tggacttcct ccgggagcgg ctgttgggct ggatccaaga ccagggtggt     540
tgggtgagac tcctcaagcc tcctcacccc caccaccgcg ccctcaccac cgcccctgcc     600
ccaccgtccc tgcccccgc cactcctctg ggaccctggg ccttctggag caggtcacag     660
tggtgccctc tccccatctt cagatcatca gatgtggtct ataatgcgtt tccttacgt     720 gtctgatcaa tccccgattc atctaccctg ctgacctccc agtgacccct gacctcactg     780
tgaccttgac ttgattagtg ccttctgccc tccctggagc ctccactgcc ctggaattg     840 ctcaagttca ttgatgaccc tctgacccta gctctttcct tttttttttt t              891

<210> SEQ ID NO 14
<211> LENGTH: 218
<212> TYPE: PRT
<213> ORGANISM: Homo sapiens

<400> SEQUENCE: 14

Met Asp Gly Ser Gly Glu Gln Pro Arg Gly Gly Gly Pro Thr Ser Ser
1                5                   10                  15

Glu Gln Ile Met Lys Thr Gly Ala Leu Leu Leu Gln Gly Phe Ile Gln
            20                  25                  30

Asp Arg Ala Gly Arg Met Gly Gly Glu Ala Pro Glu Leu Ala Leu Asp
        35                  40                  45

Pro Val Pro Gln Asp Ala Ser Thr Lys Lys Leu Ser Glu Cys Leu Lys
    50                  55                  60

Arg Ile Gly Asp Glu Leu Asp Ser Asn Met Glu Leu Gln Arg Met Ile
65                  70                  75                  80

Ala Ala Val Asp Thr Asp Ser Pro Arg Glu Val Phe Phe Arg Val Ala
                85                  90                  95

Ala Asp Met Phe Ser Asp Gly Asn Phe Asn Trp Gly Arg Val Val Ala
```

|  |  |  | 100 |  |  |  | 105 |  |  |  | 110 |  |
|--|--|--|--|--|--|--|--|--|--|--|--|--|
| Leu | Phe | Tyr | Phe | Ala | Ser | Lys | Leu | Val | Leu | Lys | Ala | Leu | Cys | Thr | Lys |

|  |  |  | 115 |  |  |  | 120 |  |  |  | 125 |  |
|--|--|--|--|--|--|--|--|--|--|--|--|--|
| Val | Pro | Glu | Leu | Ile | Arg | Thr | Ile | Met | Gly | Trp | Thr | Leu | Asp | Phe | Leu |

|  |  |  | 130 |  |  |  | 135 |  |  |  | 140 |  |
|--|--|--|--|--|--|--|--|--|--|--|--|--|
| Arg | Glu | Arg | Leu | Leu | Gly | Trp | Ile | Gln | Asp | Gln | Gly | Gly | Trp | Val | Arg |
| 145 |  |  |  |  | 150 |  |  |  |  | 155 |  |  |  |  | 160 |

| Leu | Leu | Lys | Pro | Pro | His | Pro | His | His | Arg | Ala | Leu | Thr | Thr | Ala | Pro |
|--|--|--|--|--|--|--|--|--|--|--|--|--|--|--|--|
|  |  |  |  | 165 |  |  |  |  | 170 |  |  |  |  | 175 |  |

| Ala | Pro | Pro | Ser | Leu | Pro | Pro | Ala | Thr | Pro | Leu | Gly | Pro | Trp | Ala | Phe |
|--|--|--|--|--|--|--|--|--|--|--|--|--|--|--|--|
|  |  |  | 180 |  |  |  |  | 185 |  |  |  |  | 190 |  |  |

| Trp | Ser | Arg | Ser | Gln | Trp | Cys | Pro | Leu | Pro | Ile | Phe | Arg | Ser | Ser | Asp |
|--|--|--|--|--|--|--|--|--|--|--|--|--|--|--|--|
|  |  | 195 |  |  |  |  | 200 |  |  |  |  | 205 |  |  |  |

| Val | Val | Tyr | Asn | Ala | Phe | Ser | Leu | Arg | Val |
|--|--|--|--|--|--|--|--|--|--|
| 210 |  |  |  |  | 215 |  |  |  |  |

<210> SEQ ID NO 15
<211> LENGTH: 4932
<212> TYPE: DNA
<213> ORGANISM: Homo sapiens

<400> SEQUENCE: 15

```
ggctggccga agttaggcgg agccccgagg cggggaggc ggggccgggc cggcgcaggg      60
agagtcactc aatggacagg cgagaaagca ggaccggcgc ggcggggcgg ggccggccga    120
gtccctagag ctggggcgg gcggaccca gcggaccagc ggaccacctg ggtgctgtcg     180
tagttggagg tggcctgagg agctcagttc cctcagcgcc cgtagcttcg gcggagtctg    240
cgcgatgggc gacccggaaa ggccggaagc ggccgggctg gatcaggatg agagatcatc    300
ttcagacacc aacgaaagtg aaataaagtc aaatgaagag ccactcctaa gaaagagttc    360
tcgccggttt gtcatctttc aatccagta ccctgatatt tggaaaatgt ataaacaggc    420
acaggcttcc ttctggacag cagaagaggt cgacttatca aaggatctcc ctcactggaa    480
caagcttaaa gcagatgaga agtacttcat ctctcacatc ttagccttt ttgcagccag    540
tgatggaatt gtaaatgaaa atttggtgga gcgctttagt caggaggtgc aggttccaga    600
ggctcgctgt ttctatggct ttcaaattct catcgagaat gttcactcag atgtgtacag    660
tttgctgata gacacttaca tcagagatcc aagaaaagg gaatttttat ttaatgcaat    720
tgaaaccatg ccctatgtta agaaaaaagc agattgggcc ttgcgatgga tagcagatag    780
aaaatctact tttggggaaa gagtggtggc ctttgctgct gtagaaggag ttttcttctc    840
aggatctttt gctgctatat tctggctaaa gaagagaggt cttatgccag gactcacttt    900
ttccaatgaa ctcatcagca gagatgaagg acttcactgt gactttgctt gcctgatgtt    960
ccaatactta gtaaataagc cttcagaaga aagggtcagg gagatcattg ttgatgctgt   1020
caaaattgag caggagtttt taacagaagc cttgccagtt ggcctcattg gaatgaattg   1080
cattttgatg aaacagtaca ttgagtttgt agctgacaga ttacttgtgg aacttggatt   1140
ctcaaaggtt tttcaggcag aaaatccttt tgatttatg gaaaacattt ctttagaagg   1200
aaaaacaaat ttctttgaga aacgagtttc agagtatcag cgttttgcag ttatggcaga   1260
aaccacagat aacgtcttca ccttggatgc agatttttaa aaaacctctc gttttaaaac   1320
tctataaact tgtcattggt aaatagtagt ctattttcct ctgcttaaaa aaattttaa    1380
gtatatcctt taaggactg ggggtttgct caaaaggaaa tccaaaacct attctaaaca    1440
```

```
atttgcattt atataatttt cctgtttaac aacaagagtg tgacctaaat gcttttgtct    1500
tgtcactgaa ataaaagatg gcattatgtg gttaagagca tggggcgagg ggtcagacat    1560
gagtctaagg ttctgcccct actccagtgt gtgacccttg gcaagtcagt taatcttggt    1620
aaacctcggt gtacttatct ttaaaatggg agtaatagta ggtcctaaat tcatagagtg    1680
gatattagga ttaggatgca aaataaaatg cttaaccaac actactactg ttagcaccac    1740
tactaattat cattcattga taatattaat tgcaatgatg ttgtaataaa atactctcat    1800
ttccttaaaa taattgtgat tctaggtcct aggatctaga attagatctt tgtatttta     1860 atgcttaggg gaagaatata agtatctcct taaaagaaac ataattctca ttcacgcaag    1920
aataagttct ttgaattcct tagtatgtag tgaagaaaat ttagttgtta gttgctttgg    1980
gaagcctact tatggagtgg aaaccaggag gttatcatgg tagttgacct tataagaaaa    2040
atgattcttc ttcagaaatt aaaaacataa ctattgccag atttagctct ggaatgttta    2100
gaatcaggct agaatagcat tttccaaaga atattctaag agctattagc tcctctagat    2160
atttttttgg gggaaaaagg ggattctgtg gtcagatgag tttgggaaat gctgaacact    2220
tcattcttct ttagcaagta cagtcagtac atcaaagact gagcagttca gtggtacata    2280
aatttatctc gccctgcata ttcccaacat acttaacaca gatgttttt acctgttaac     2340 atctcaccca gctagtgttc ctcagaacaa agattggaaa aagctggccg agaaccattt    2400
atacatagag gaagggctta tggactgaga aaggagaaac atggtaggga ttattgaatc    2460
atttcaaatt tataccagcc tgaatagtgt accagcaatt gacttaggct gtgtttcttt    2520
atggttttaa aactcttgag ctgttataag agatagttct tttaatgtga ctatgcaaca    2580
tgatagccaa tggtgaggga aaaggaggtt tctctagaag agtctgatga aaggccggga    2640
accaaggttt ttgagaagtc tgcccctatt tattttagt aagtatcaag aggtagcctg     2700
agcctagtta gagttagacc tgtctttgga tgaagaagtc ttaatactga aatactgaat    2760
ttttaataca ttattatttg gtattctgta taccccttca agcagttgtt tcccattccc    2820
aacaaactgt actttataca attctggatg ctaaaactta gagattttct ctttgcataa    2880
attttggctc cattctttcc ataacaatct aatcaaaact gggagttctc aagtgaatgc    2940
aaaaggagca ggccataact ttatttgtta gatacactgt cagaaacttg agatcttttg    3000
gcctatgata ataccattaa ttttgcatt gcttcagttt gccaagtgtt tttacatcat      3060
ctcatttgat ctcaaaacag cttgacagag caactgttat tgaaatatta cagatggaaa    3120
gaatgaggct cagggaagtt aaatgacttg gccaagatct gctcatcgtc actgtctgta    3180 cagtatttt ttttagaggt tgtaatgtct cagatttagt cctttaccat ctatgttgat      3240
ttgcttttgt ctatttcctc attaattgaa tatactttaa atatatatat taaagtatca    3300
aaatatagag agacatttga actgtattca ggtaatatgt ttaaagatat ttatatattg    3360
ccatacaaaa acttaacatt taaaactgat aatatctgta atgacatcag aatgaaagaa    3420
aaaaaattgt acagtgtata ttcctttgtt ttgaatccaa atcttttca taggtaatga     3480 cagatgcctt aatgtgaagc ttatttataa tagcaataaa cctaactgga tttggatgaa    3540
gaagtcttaa tactgacata ctggattttt aatgcactgg tttgttattt ggtattctat    3600 ctcttttcc aggcctccag gttgcacatt tatttattat gttcaatact ttggttctta     3660
gttcttaaag aatcaagaag ttgtgtaatc ttttaaaaat attatcttgc agataaagaa    3720
aaaaattaag agtgtgttta caactgtttt ctcttttta cagtacatgt atttaaatca      3780
ttgctataat aaagttaagt tcattaggaa tataaaaact tgcagttcta tgatagattg    3840
```

-continued

```
catttattaa aaatgtttca ttgtatcaca tagaaatatg gccaggaagg acttgagaag    3900
acagtttgat ccattgcttt tagacaggac tgggttttgc tgtccaatta tatacaataa    3960
tagttttttct tacaactaag ctggccccag ccttgtcttg atattaatac atgaaatttt    4020
tataattgtc tcattgtctc atttagaaac atccatattt ttctgctttt tctattgcca    4080
tttttttattt gtgcatgaat tgattattga gaaaatgtag cagtttgcat atttaaaaat    4140
taatcatttt gcatttttaca tttaaatatg ctaacatcac tgtcatagaa ttcccaaatt    4200
tcatttgtag atactgaact aagggctaat gtcaggagct gattttttaat gataaagctg    4260
cagatgggct aaataaaagc caaattaatc ctacaatcag gtattatgtt tttaaaccaa    4320
gttgagtgaa ttggtagtgg acttgggaaa tcttccccag cagaatctgg atgaatggca    4380
cagaattgaa atctctttgt ttcccaccat ttccctttaa gtgctctgct cctttgtaaa    4440
aagttaaaga tttgaaagag aatctcatat tcccgaggca ttaggaagaa aggatttaat    4500
cccttcaatt tggggcttaa tcttgtttaa aaaaatgtaa gtgaagatgg aaggctggag    4560
agaatgattg cttttttgtac agttaaataa ggtcacaata ttcttacata ctttgtttta    4620
caactgtgtt ttcattttttt caaatgtctg gccatttagc aaagttattt actatttact    4680
gtgtacatag aaagctttat tatgtgtggt gtatctaaat ttttttttgct gaaatacatt    4740
atggtcaatc aagccaagcc tgcatgtaca gaatttgttt tttttttcaaa taaattagtt    4800
gttttcttat ttttttggct tagtatgttg aaataaacta tggtatcttc atcattttgt    4860
acatttcctt tttgaggaag gtttctttat aagtgcaagg gctaccctaa taaaggaatg    4920
tatatactta ct                                                       4932
```

<210> SEQ ID NO 16
<211> LENGTH: 351
<212> TYPE: PRT
<213> ORGANISM: Homo sapiens

<400> SEQUENCE: 16

Met Gly Asp Pro Glu Arg Pro Glu Ala Ala Gly Leu Asp Gln Asp Glu
1               5                   10                  15

Arg Ser Ser Ser Asp Thr Asn Glu Ser Glu Ile Lys Ser Asn Glu Glu
                20                  25                  30

Pro Leu Leu Arg Lys Ser Arg Arg Phe Val Ile Phe Pro Ile Gln
            35                  40                  45

Tyr Pro Asp Ile Trp Lys Met Tyr Lys Gln Ala Gln Ala Ser Phe Trp
        50                  55                  60

Thr Ala Glu Glu Val Asp Leu Ser Lys Asp Leu Pro His Trp Asn Lys
65                  70                  75                  80

Leu Lys Ala Asp Glu Lys Tyr Phe Ile Ser His Ile Leu Ala Phe Phe
                85                  90                  95

Ala Ala Ser Asp Gly Ile Val Asn Glu Asn Leu Val Glu Arg Phe Ser
            100                 105                 110

Gln Glu Val Gln Val Pro Glu Ala Arg Cys Phe Tyr Gly Phe Gln Ile
        115                 120                 125

Leu Ile Glu Asn Val His Ser Glu Met Tyr Ser Leu Leu Ile Asp Thr
    130                 135                 140

Tyr Ile Arg Asp Pro Lys Lys Arg Glu Phe Leu Phe Asn Ala Ile Glu
145                 150                 155                 160

Thr Met Pro Tyr Val Lys Lys Lys Ala Asp Trp Ala Leu Arg Trp Ile
                165                 170                 175

```
Ala Asp Arg Lys Ser Thr Phe Gly Glu Arg Val Val Ala Phe Ala Ala
            180                 185                 190

Val Glu Gly Val Phe Phe Ser Gly Ser Phe Ala Ala Ile Phe Trp Leu
        195                 200                 205

Lys Lys Arg Gly Leu Met Pro Gly Leu Thr Ser Asn Glu Leu Ile
    210                 215                 220

Ser Arg Asp Glu Gly Leu His Cys Asp Phe Ala Cys Leu Met Phe Gln
225                 230                 235                 240

Tyr Leu Val Asn Lys Pro Ser Glu Arg Val Arg Glu Ile Ile Val
                245                 250                 255

Asp Ala Val Lys Ile Glu Gln Glu Phe Leu Thr Glu Ala Leu Pro Val
                260                 265                 270

Gly Leu Ile Gly Met Asn Cys Ile Leu Met Lys Gln Tyr Ile Glu Phe
            275                 280                 285

Val Ala Asp Arg Leu Leu Val Glu Leu Gly Phe Ser Lys Val Phe Gln
290                 295                 300

Ala Glu Asn Pro Phe Asp Phe Met Glu Asn Ile Ser Leu Glu Gly Lys
305                 310                 315                 320

Thr Asn Phe Phe Glu Lys Arg Val Ser Glu Tyr Gln Arg Phe Ala Val
                325                 330                 335

Met Ala Glu Thr Thr Asp Asn Val Phe Thr Leu Asp Ala Asp Phe
            340                 345                 350

<210> SEQ ID NO 17
<211> LENGTH: 3212
<212> TYPE: DNA
<213> ORGANISM: Homo sapiens

<400> SEQUENCE: 17
gaacccggtg gctgcacaga caaaaaagcc ccgaatggct ggagggcgtt cagctgttaa    60
cagccttttg gggcagagca cggatttgac agctccacaa cgtgaggata tccactgacc   120
ccgcgagacg gaggagaacg cttccccgaa attctctgcc caccaaagcc agcgctgcaa   180
ggttgcaact ttcaaacttt gttttttccag aaagaagact gcccttttcgt gtacaaggag   240 agggtgagag ggtgacctag cttgtagatc ggctgaaggc accagtggtt ccaaatgtca   300
cccagatgtg tgttttcatg acgatttgat ttctctgatt ttattttttac attttttcatt   360 ttaaaaatac aaagcaattt ttttggggca tgctgaaagg taactgaaga ccgcaaagga   420
aaaactattg tcatggctga aggagagaat gaagtgagat gggatggact ctgcagcaga   480
gattcaacta ctagggagac agcattggaa acattaggc aaaccatttt gaggaaaacc   540
gagtatcttc gttcggtgaa agaaacacct catcgtccat cagacgggct ttcaaatacc   600
gagtcttcgg atgggttgaa taagctactt gctcatctgc ttatgctttc taagaggtgt   660
cccttcaaag atgtgagaga gaaaagtgag tttattctga agagcatcca ggaacttggc   720
attagaattc ctcgaccact aggacaggga ccaagcagat tcatcccaga aaaggagatc   780
ctccaagtgg ggagtgaaga cgcacagatg catgctttat ttgcagattc ttttgctgct   840
ttgggccgtt tggataacat tacgttagtg atggttttcc acccacaata tttagaaagt   900
ttcttaaaaa ctcagcacta tctactgcaa atggatgggc cgttacccct acattatcgt   960
cactacattg gaataatggc tgcggcaaga catcagtgct cctacttagt gaacctgcat  1020
gtaaatgatt tccttcatgt tggtggggac cccaagtggc tcaatggttt agagaatgct  1080
cctcaaaaac tacagaattt aggagaactt aacaaagtgt tagcccatag accttggctt  1140
```

```
attaccaaag aacacattga gggacttttta aaagctgaag agcacagctg gtcccttgcg    1200
gaattggtac atgcagtagt tttactcaca cactatcatt ctcttgcctc attcacattc    1260
ggctgtggaa tcagtccaga aattcattgt gatggtggcc acacattcag acctccttct    1320
gttagcaact actgcatctg tgacattaca atggcaatc acagtgtgga tgagatgccg     1380
gtcaactcag cagaaaatgt ttctgtaagt gattctttct ttgaggttga agccctcatg    1440
gaaaagatga ggcagttaca ggaatgtcga tgaagaaag aggcaagtca ggaagagatg     1500
gcttcacgtt ttgaaataga aaaagagag agtatgtttg tcttctcttc agatgatgaa     1560
gaagttacac cagcaagagc tgtatctcgt cattttgagg atactagtta tggctataaa    1620
gatttctcta gacatgggat gcatgttcca acatttcgtg tccaggacta ttgctgggaa    1680
gatcatggtt attctttggt aaatcgcctt tatccagatg tgggacagtt gattgatgaa    1740
aaatttcaca ttgcttacaa tcttacttat aatacaatgg caatgcacaa agatgttgat    1800
acctcaatgc ttagacgggc aatttggaac tatattcact gcatgtttgg aataagatat    1860
gatgattatg actatggtga aattaaccag ctattggatc gtagctttaa agtttatatc    1920
aaaactgttg tttgcactcc tgaaaaggtt accaaaagaa tgtatgatag cttctggagg    1980
cagttcaagc actctgagaa ggttcatgtt aatctgcttc ttatagaagc taggatgcaa    2040
gcagaactcc tttatgctct gagagccatt acccgctata tgacctgatg cctttccttc    2100
attaaagatg attctggaat gatcagcaga tatagtctac aagggggaag gtactaagcc    2160
ccaggaccaa tggtagacaa aataattcag aaatccattg tgccatgatt cctttagttt    2220
ctgctatttt tctgtggaaa accactgctg gcacaagcag tgactgtttg gcagcttcaa    2280
gtttagagct gtgaagacag gctgccattc acagtatttt gcttttgac agtacaagat    2340
gctgtgtaac tgttttaata cagcaaatag taactctcca aatcctgttg cttttatgtt    2400
aaataagata acaagaattg gagcatgcaa agaatgggac ttggataatg acttaagctt    2460
tatatgtaaa gaattttaga agatcttggt gctgctattc ctgctggagg aatgaataga    2520
tggctgtttc agttaagcta ttagtaataa aagtgaacat tgctactatc tgagcctaca    2580
tacataactt gtgtgatttc aaattaaact tgcattatgt gttaattttc ttgcatctaa    2640
aaaagcatag aattcctact cacacagctc agcaacaacc attttgatgg taacagttaa    2700
tttctttcat tagtttttta aattcagggt tctggatatt aaattaaaat ggcattctta    2760
aagattttct tcaaaaagca atcctaaatg aaagtgtgta aattataaga agctggcgat    2820
cttttgatat gctgtttcac aggatcctga cactggaggg cagctgtctt gtgcattact    2880
tgtgttttcca gcaccaaagt tgtgggacat gttgctgtag actgctgcgc agtcctgggt    2940
gcattcagtc tctctgcctc tgcctgcctc ctggtcccca ctttaaaggc tgtgcagctc    3000
cttaaataat aaagctggaa atatttttta gtcgggttat caaatttgat ttacaaaaac    3060
gctaactttg tttgaaatgc aaacaggttt gaaaatatgt attaagtact ttgtattctg    3120
gaagcgtgaa ttgcttttga agtctgtcag tattactggt attttaaat aagaagaat     3180
ttttctccaa ttttaaaaaa aaaaaaaaaa aa                                   3212
```

<210> SEQ ID NO 18
<211> LENGTH: 551
<212> TYPE: PRT
<213> ORGANISM: Homo sapiens

<400> SEQUENCE: 18

```
Met Ala Glu Gly Glu Asn Glu Val Arg Trp Asp Gly Leu Cys Ser Arg
1               5                   10                  15

Asp Ser Thr Thr Arg Glu Thr Ala Leu Glu Asn Ile Arg Gln Thr Ile
            20                  25                  30

Leu Arg Lys Thr Glu Tyr Leu Arg Ser Val Lys Glu Thr Pro His Arg
        35                  40                  45

Pro Ser Asp Gly Leu Ser Asn Thr Glu Ser Ser Asp Gly Leu Asn Lys
50                  55                  60

Leu Leu Ala His Leu Leu Met Leu Ser Lys Arg Cys Pro Phe Lys Asp
65                  70                  75                  80

Val Arg Glu Lys Ser Glu Phe Ile Leu Lys Ser Ile Gln Glu Leu Gly
                85                  90                  95

Ile Arg Ile Pro Arg Pro Leu Gly Gln Gly Pro Ser Arg Phe Ile Pro
            100                 105                 110

Glu Lys Glu Ile Leu Gln Val Gly Ser Glu Asp Ala Gln Met His Ala
        115                 120                 125

Leu Phe Ala Asp Ser Phe Ala Ala Leu Gly Arg Leu Asp Asn Ile Thr
130                 135                 140

Leu Val Met Val Phe His Pro Gln Tyr Leu Glu Ser Phe Leu Lys Thr
145                 150                 155                 160

Gln His Tyr Leu Leu Gln Met Asp Gly Pro Leu Pro Leu His Tyr Arg
                165                 170                 175

His Tyr Ile Gly Ile Met Ala Ala Arg His Gln Cys Ser Tyr Leu
            180                 185                 190

Val Asn Leu His Val Asn Asp Phe Leu His Val Gly Gly Asp Pro Lys
        195                 200                 205

Trp Leu Asn Gly Leu Glu Asn Ala Pro Gln Lys Leu Gln Asn Leu Gly
210                 215                 220

Glu Leu Asn Lys Val Leu Ala His Arg Pro Trp Leu Ile Thr Lys Glu
225                 230                 235                 240

His Ile Glu Gly Leu Leu Lys Ala Glu Glu His Ser Trp Ser Leu Ala
                245                 250                 255

Glu Leu Val His Ala Val Val Leu Leu Thr His Tyr His Ser Leu Ala
            260                 265                 270

Ser Phe Thr Phe Gly Cys Gly Ile Ser Pro Glu Ile His Cys Asp Gly
        275                 280                 285

Gly His Thr Phe Arg Pro Pro Ser Val Ser Asn Tyr Cys Ile Cys Asp
290                 295                 300

Ile Thr Asn Gly Asn His Ser Val Asp Glu Met Pro Val Asn Ser Ala
305                 310                 315                 320

Glu Asn Val Ser Val Ser Asp Ser Phe Phe Glu Val Glu Ala Leu Met
                325                 330                 335

Glu Lys Met Arg Gln Leu Gln Glu Cys Arg Asp Glu Glu Glu Ala Ser
            340                 345                 350

Gln Glu Glu Met Ala Ser Arg Phe Glu Ile Glu Lys Arg Glu Ser Met
        355                 360                 365

Phe Val Phe Ser Ser Asp Asp Glu Glu Val Thr Pro Ala Arg Ala Val
370                 375                 380

Ser Arg His Phe Glu Asp Thr Ser Tyr Gly Tyr Lys Asp Phe Ser Arg
385                 390                 395                 400

His Gly Met His Val Pro Thr Phe Arg Val Gln Asp Tyr Cys Trp Glu
                405                 410                 415

Asp His Gly Tyr Ser Leu Val Asn Arg Leu Tyr Pro Asp Val Gly Gln
```

```
                420           425           430
Leu Ile Asp Glu Lys Phe His Ile Ala Tyr Asn Leu Thr Tyr Asn Thr
            435                 440                 445

Met Ala Met His Lys Asp Val Asp Thr Ser Met Leu Arg Arg Ala Ile
450                 455                 460

Trp Asn Tyr Ile His Cys Met Phe Gly Ile Arg Tyr Asp Asp Tyr Asp
465                 470                 475                 480

Tyr Gly Glu Ile Asn Gln Leu Leu Asp Arg Ser Phe Lys Val Tyr Ile
                485                 490                 495

Lys Thr Val Val Cys Thr Pro Glu Lys Val Thr Lys Arg Met Tyr Asp
                500                 505                 510

Ser Phe Trp Arg Gln Phe Lys His Ser Glu Lys Val His Val Asn Leu
            515                 520                 525

Leu Leu Ile Glu Ala Arg Met Gln Ala Glu Leu Leu Tyr Ala Leu Arg
            530                 535                 540

Ala Ile Thr Arg Tyr Met Thr
545                 550

<210> SEQ ID NO 19
<211> LENGTH: 2484
<212> TYPE: DNA
<213> ORGANISM: Homo sapiens

<400> SEQUENCE: 19
attcctcgtt agggcaggcg cggcccttc ggctccgagc tgaccctgat cagggccgag      60
ttgtctcggc ggcgctgccg aggcctccac ccaggacagt ccccctcccc gggcctctct    120
cctcttgcct acgagtcccc tctcctcgta ggcctctcgg atctgatatc gtggggtgag    180
gtgagcaggc ccggggaggg tggttaccgc tgaggagctg cagtctctgt caagatgata    240
gaggtactga caacaactga ctctcagaaa ctgctacacc agctgaatgc cctgttggaa    300
caggagtcta gatgtcagcc aaaggtctgt ggtttgagac taattgagtc tgcacacgat    360
aatggcctca gaatgactgc aagactaagg gactttgaag taaagatctc tcttagtcta    420
actcagttct ttggctttga cacagagaca ttttctctag ctgtgaattt actggacaga    480
ttcctgtcta aaatgaaggt acagcccaag caccttgggt gtgttggact gagctgcttt    540
tatttggctg taaatcaat agaagaggaa aggaatgtcc cattggcaac tgacttgatc    600
cgaataagtc aatataggtt tacggtttca gacttgatga aatggaaaa gattgtattg    660
gagaaggtgt gttggaaagt caaagctact actgcctttc aatttctgca actgtattat    720
tcactccttc aagagaactt gccacttgaa aggagaaata gcattaattt tgaaagacta    780
gaagctcaac tgaaggcatg tcattgcagg atcatatttt ctaaagcaaa gccttctgtg    840
ttggcattgt ctatcattgc attagagatc caagcacaga agtgtgtaga gttaacagaa    900
ggaatagaat gtcttcagaa acattccaag ataaatggca gagatctgac cttctggcaa    960
gagcttgtat ccaaatgttt aactgaatat tcatcaaata gtgttccaa accaaatgtt   1020
cagaagttga atggattgt ttctgggcgt actgcacggc aattgaagca tagctactac   1080
agaataactc accttccaac aattcctgaa atggtccctt aactggatta ttacagcacc   1140
aaaaaacttc tctgaagcct ttctccacaa ccttgttcta tggattccat aatgttacaa   1200
tggatttaag ctatgaagcc tcaaaacatc acgagataag catgatggtc tcagacttgg   1260
gaaaactgcc taatattatg ctgtagtgga attatgtta gatttgaatt catctgtgaa   1320
gcattcaaat caaagctaaa agcctaaatg tgaaatgcta atgacaagcc tgagaaggta   1380
```

```
aactgtgaat cttcatttct atcattgatc taactttaga tattggatca atatatttag    1440
gtggtattga aaatgctatt ggaggagtca cactaatact atcaactatc agtcttccca    1500
cagcttcaat cactgtcatt attctaatcc tactcctact taaattttaa gttatgaggt    1560
ttatgtcaaa agcaacattt cacaaatgta cttttaaggc ataataaggg ttaacattct    1620
aggcagtata aacacacccc ataatgcaag taataggtaa tctagagatg tggactttat    1680
tgctatatgg gaattacatt taaatttgag ggcattttat ataaagaaaa atacagacct    1740
ataaagtttg gcatattcat taagttatct tttaatattt ttttctagaa aacaggtgac    1800
atttgtatct acgataaaaa ttttataca gaacctactg cctcaaactg aatcccatca     1860
agaaaactag tttctattgt attagtaact caaaataaat tatcacttcg aaaacttgct    1920
ttcccacact aaggtaagtt cagactagat tgaacactcc agaatttttt actacagact    1980 gttttttaagt tagaagtgat ggcaattttta taaatagaga atatacttcc actgatgccc   2040
ttactgtgcc aaaacaaaaa tcttaagaaa agcaagtaga caccttcata actatgaatg    2100
aagctgctga agtagtgttt aggatcctcc atggcagtta gtgaatgtaa gaagtacagt    2160
gttaaagtgt tgtaaacagt tactcagtgc aatgtatagc ctgagtctat ccatgatggc    2220
tatatccaat ttgacatcac gttatggatc agtacacaat gaaaaaccaa agaaccacag    2280
tatatcttat tcttaacttt tgtaaaccat gttttatggg taacttttta gtttccccaa    2340
aaggctgata aatttcaata ttttgaatac atcattgtta attttgagtt ggcagaggta    2400
aactaaccaa ctaccattat gttttagtac taagggatat accttttcaat aaagttaatg   2460 aaattcaaaa aaaaaaaaaa aaaa                                           2484
```

<210> SEQ ID NO 20
<211> LENGTH: 295
<212> TYPE: PRT
<213> ORGANISM: Homo sapiens

<400> SEQUENCE: 20

```
Met Ile Glu Val Leu Thr Thr Thr Asp Ser Gln Lys Leu Leu His Gln
1               5                   10                  15

Leu Asn Ala Leu Leu Glu Gln Glu Ser Arg Cys Gln Pro Lys Val Cys
            20                  25                  30

Gly Leu Arg Leu Ile Glu Ser Ala His Asp Asn Gly Leu Arg Met Thr
        35                  40                  45

Ala Arg Leu Arg Asp Phe Glu Val Lys Asp Leu Leu Ser Leu Thr Gln
    50                  55                  60

Phe Phe Gly Phe Asp Thr Glu Thr Phe Ser Leu Ala Val Asn Leu Leu
65                  70                  75                  80

Asp Arg Phe Leu Ser Lys Met Lys Val Gln Pro Lys His Leu Gly Cys
                85                  90                  95

Val Gly Leu Ser Cys Phe Tyr Leu Ala Val Lys Ser Ile Glu Glu Glu
            100                 105                 110

Arg Asn Val Pro Leu Ala Thr Asp Leu Ile Arg Ile Ser Gln Tyr Arg
        115                 120                 125

Phe Thr Val Ser Asp Leu Met Arg Met Glu Lys Ile Val Leu Glu Lys
    130                 135                 140

Val Cys Trp Lys Val Lys Ala Thr Thr Ala Phe Gln Phe Leu Gln Leu
145                 150                 155                 160

Tyr Tyr Ser Leu Leu Gln Glu Asn Leu Pro Leu Glu Arg Arg Asn Ser
                165                 170                 175
```

Ile Asn Phe Glu Arg Leu Glu Ala Gln Leu Lys Ala Cys His Cys Arg
            180                 185                 190

Ile Ile Phe Ser Lys Ala Lys Pro Ser Val Leu Ala Leu Ser Ile Ile
        195                 200                 205

Ala Leu Glu Ile Gln Ala Gln Lys Cys Val Glu Leu Thr Glu Gly Ile
    210                 215                 220

Glu Cys Leu Gln Lys His Ser Lys Ile Asn Gly Arg Asp Leu Thr Phe
225                 230                 235                 240

Trp Gln Glu Leu Val Ser Lys Cys Leu Thr Glu Tyr Ser Ser Asn Lys
                245                 250                 255

Cys Ser Lys Pro Asn Val Gln Lys Leu Lys Trp Ile Val Ser Gly Arg
            260                 265                 270

Thr Ala Arg Gln Leu Lys His Ser Tyr Tyr Arg Ile Thr His Leu Pro
        275                 280                 285

Thr Ile Pro Glu Met Val Pro
    290                 295

<210> SEQ ID NO 21
<211> LENGTH: 3729
<212> TYPE: DNA
<213> ORGANISM: Homo sapiens

<400> SEQUENCE: 21
cgaaggggcg tggccaagcg caccgcctcg ggcgggggcc ggcgttctag cgcatcgcgg      60
ccgggtgcgt cactcgcgaa gtggaatttg cccagacaag caacatggct cggaaacgcg     120
cggccggcgg ggagccgcgg ggacgcgaac tgcgcagcca gaatccaag gccaagagca      180 aggcccggcg tgaggaggag gaggaggatg cctttgaaga tgagaaaccc ccaaagaaga     240
gccttctctc caaagtttca caaggaaaga ggaaaagagg ctgcagtcat cctgggggtt     300
cagcagatgg tccagcaaaa aagaaagtgg ccaaggtgac tgttaaatct gaaaacctca     360
aggttataaa ggatgaagcc ctcagcgatg ggatgaccct cagggacttt ccaagtgacc     420
tcaagaaggc acaccatctg aagagagggg ctaccatgaa tgaagacagc aatgaagaag     480
aggaagaaag tgaaaatgat tgggaagagg ttgaagaact tagtgagcct gtgctgggtg     540
acgtgagaga aagtacagcc ttctctcgat ctcttctgcc tgtgaagcca gtggagatag     600
agattgaaac gccagagcag gcgaagacaa gagaaagaag tgaaaagata aaactggagt     660
ttgagacata tcttcggagg gcgatgaaac gtttcaataa aggggtccat gaggacacac     720
acaaggttca ccttctctgc ctgctagcaa atggcttcta tcgaaataac atctgcagcc     780
agccagatct gcatgctatt ggcctgtcca tcatcccagc ccgctttacc agagtgctgc     840
ctcgagatgt ggacacctac tacctctcaa acctggtgaa gtggtcatt ggaacattta      900 cagttaatgc agaactttca gccagtgaac aagataacct gcagactaca ttggaaagga     960
gatttgctat ttactctgct cgagatgatg aggaattggt ccatatattc ttactgattc    1020
tccgggctct gcagctcttg acccggctgg tattgtctct acagccaatt cctctgaagt    1080
cagcaacagc aaagggaaag aaaccttcca aggaaagatt gactgcggat ccaggaggct    1140
cctcagaaac ttccagccaa gttctagaaa accacaccaa accaaagacc agcaaaggaa    1200
ccaaacaaga ggaaaccttt gctaagggca cctgcaggcc aagtgccaaa gggaagagga    1260
acaagggagg cagaaagaaa cggagcaagc cctcctccag cgaggaagat gagggcccag    1320
gagacaagca ggagaaggca acccagcgac gtccgcatgg ccgggagcgg cgggtggcct    1380

```
ccagggtgtc ttataaagag gagagtggga gtgatgaggc tggcagcggc tctgattttg    1440
agctctccag tggagaagcc tctgatccct ctgatgagga ttccgaacct ggccctccaa    1500
agcagaggaa agccccgct cctcagagga caaaggctgg gtccaagagt gcctccagga     1560
cccatcgtgg gagccatcgt aaggacccaa gcttgccagc ggcatcctca agctcttcaa    1620
gcagtaaaag aggcaagaaa atgtgcagcg atggtgagaa ggcagaaaaa agaagcatag    1680
ctggtataga ccagtggcta gaggtgttct gtgagcagga ggaaaagtgg gtatgtgtag    1740
actgtgtgca cggtgtggtg ggccagcctc tgacctgtta caagtacgcc accaagccca    1800
tgacctatgt ggtgggcatt gacagtgacg gctgggtccg agatgtcaca cagaggtacg    1860
acccagtctg gatgacagtg acccgcaagt gccgggttga tgctgagtgg tgggccgaga    1920
ccttgagacc ataccagagc ccatttatgg acagggagaa gaagaagac ttggagtttc     1980
aggcaaaaca catggaccag cctttgccca ctgccattgg cttatataag aaccaccctc    2040
tgtatgccct gaagcggcat ctcctgaaat atgaggccat ctatcccgag acagctgcca    2100
tccttgggta ttgtcgtgga gaagcggtct actccaggga ttgtgtgcac actctgcatt    2160
ccagggacac gtggctgaag aaagcaagag tggtgaggct tggagaagta ccctacaaga    2220
tggtgaaagg ctttttctaac cgtgctcgga agcccgact tgctgagccc cagctgcggg    2280
aagaaaatga cctgggcctg tttggctact ggcagacaga ggagtatcag ccccagtgg    2340
ccgtggacgg gaaggtgccc cggaacgagt ttgggaatgt gtacctcttc ctgcccagca    2400
tgatgcctat tggctgtgtc cagctgaacc tgcccaatct acaccgcgtg gcccgcaagc    2460
tggacatcga ctgtgtccag gccatcactg gctttgattt ccatggcggc tactcccatc    2520
ccgtgactga tggatacatc gtctgcgagg aattcaaaga cgtgctcctg actgcctggg    2580
aaaatgagca ggcagtcatt gaaggaagg agaaggagaa aaaggagaag cgggctctag    2640
ggaactggaa gttgctggcc aaaggtctgc tcatcaggga gaggctgaag cgtcgctacg    2700
ggcccaagag tgaggcagca gctcccccaca cagatgcagg aggtggactc tcttctgatg    2760
aagaggaggg gaccagctct caagcagaag cggccaggat actggctgcc tcctggcctc    2820
aaaaccgaga agatgaagaa agcagaagc tgaaggtgg gcccaagaag accaaaaggg     2880
aaaagaaagc agcagcttcc cacctgttcc catttgagca gctgtgagct gagcgcccac    2940
tagaggggca cccaccagtt gctgctgccc cactacaggc cccacacctg ccctgggcat    3000
gcccagcccc tggtggtggg ggcttctctg ctgagaaggc aaactgaggc agcatgcacg    3060
gaggcggggt cagggagac gaggccaagc tgagaggtg ctgcaggtcc cgtctggctc      3120
cagcccttgt cagattcacc cagggtgaag ccttcaaagc ttttttgctac caaagcccac    3180
tcacccttt gagctacagaa cactttgcta ggagatactc ttctgcctcc tagacctgtt    3240
ctttccatct ttagaaacat cagttttttgt atggaagcca ccgggagatt tctggatggt    3300
ggtgcatccg tgaatgcgct gatcgtttct tccagttaga gtcttcatct gtccgacaag    3360
ttcactcgcc tcggttgcgg acctaggacc atttctctgc aggccactta ccttcccctg    3420
agtcaggctt actaatgctg ccctcactgc ctctttgcag taggggagag agcagagaag    3480
tacaggtcat ctgctgggat ctagttttcc aagtaacatt ttgtggtgac agaagcctaa    3540
aaaaagctaa aatcaggaaa gaaaaggaaa aatacgaatt gaaaattaag gaaatgttag    3600
taaaatagat gagtgttaaa ctagattgta ttcattacta gataaaatgt ataaagctct    3660
ctgtactaag gagaaatgac ttttataaca ttttgagaaa ataataaagc atttatctaa    3720
aaaaaaaaa                                                            3729
```

<210> SEQ ID NO 22
<211> LENGTH: 940
<212> TYPE: PRT
<213> ORGANISM: Homo sapiens

<400> SEQUENCE: 22

Met Ala Arg Lys Arg Ala Ala Gly Gly Glu Pro Arg Gly Arg Glu Leu
1               5                   10                  15

Arg Ser Gln Lys Ser Lys Ala Lys Ser Lys Ala Arg Arg Glu Glu Glu
            20                  25                  30

Glu Glu Asp Ala Phe Glu Asp Glu Lys Pro Pro Lys Lys Ser Leu Leu
        35                  40                  45

Ser Lys Val Ser Gln Gly Lys Arg Lys Arg Gly Cys Ser His Pro Gly
    50                  55                  60

Gly Ser Ala Asp Gly Pro Ala Lys Lys Val Ala Lys Val Thr Val
65                  70                  75                  80

Lys Ser Glu Asn Leu Lys Val Ile Lys Asp Glu Ala Leu Ser Asp Gly
                85                  90                  95

Asp Asp Leu Arg Asp Phe Pro Ser Asp Leu Lys Lys Ala His His Leu
            100                 105                 110

Lys Arg Gly Ala Thr Met Asn Glu Asp Ser Asn Glu Glu Glu Glu Glu
        115                 120                 125

Ser Glu Asn Asp Trp Glu Glu Val Glu Glu Leu Ser Glu Pro Val Leu
    130                 135                 140

Gly Asp Val Arg Glu Ser Thr Ala Phe Ser Arg Ser Leu Leu Pro Val
145                 150                 155                 160

Lys Pro Val Glu Ile Glu Ile Glu Thr Pro Glu Gln Ala Lys Thr Arg
                165                 170                 175

Glu Arg Ser Glu Lys Ile Lys Leu Glu Phe Glu Thr Tyr Leu Arg Arg
            180                 185                 190

Ala Met Lys Arg Phe Asn Lys Gly Val His Glu Asp Thr His Lys Val
        195                 200                 205

His Leu Leu Cys Leu Leu Ala Asn Gly Phe Tyr Arg Asn Asn Ile Cys
    210                 215                 220

Ser Gln Pro Asp Leu His Ala Ile Gly Leu Ser Ile Ile Pro Ala Arg
225                 230                 235                 240

Phe Thr Arg Val Leu Pro Arg Asp Val Asp Thr Tyr Tyr Leu Ser Asn
                245                 250                 255

Leu Val Lys Trp Phe Ile Gly Thr Phe Thr Val Asn Ala Glu Leu Ser
            260                 265                 270

Ala Ser Glu Gln Asp Asn Leu Gln Thr Thr Leu Glu Arg Arg Phe Ala
        275                 280                 285

Ile Tyr Ser Ala Arg Asp Asp Glu Glu Leu Val His Ile Phe Leu Leu
    290                 295                 300

Ile Leu Arg Ala Leu Gln Leu Leu Thr Arg Leu Val Leu Ser Leu Gln
305                 310                 315                 320

Pro Ile Pro Leu Lys Ser Ala Thr Ala Lys Gly Lys Pro Ser Lys
                325                 330                 335

Glu Arg Leu Thr Ala Asp Pro Gly Gly Ser Ser Glu Ser Ser Gln
            340                 345                 350

Val Leu Glu Asn His Thr Lys Pro Lys Thr Ser Lys Gly Thr Lys Gln
    355                 360                 365

Glu Glu Thr Phe Ala Lys Gly Thr Cys Arg Pro Ser Ala Lys Gly Lys

```
              370                 375                 380
Arg Asn Lys Gly Gly Arg Lys Lys Arg Ser Lys Pro Ser Ser Ser Glu
385                 390                 395                 400

Glu Asp Glu Gly Pro Gly Asp Lys Gln Glu Lys Ala Thr Gln Arg Arg
                405                 410                 415

Pro His Gly Arg Glu Arg Arg Val Ala Ser Arg Val Ser Tyr Lys Glu
            420                 425                 430

Glu Ser Gly Ser Asp Glu Ala Gly Ser Gly Ser Asp Phe Glu Leu Ser
        435                 440                 445

Ser Gly Glu Ala Ser Asp Pro Ser Asp Glu Asp Ser Glu Pro Gly Pro
    450                 455                 460

Pro Lys Gln Arg Lys Ala Pro Ala Pro Gln Arg Thr Lys Ala Gly Ser
465                 470                 475                 480

Lys Ser Ala Ser Arg Thr His Arg Gly Ser His Arg Lys Asp Pro Ser
                485                 490                 495

Leu Pro Ala Ala Ser Ser Ser Ser Ser Ser Lys Arg Gly Lys Lys
            500                 505                 510

Met Cys Ser Asp Gly Glu Lys Ala Glu Lys Arg Ser Ile Ala Gly Ile
        515                 520                 525

Asp Gln Trp Leu Glu Val Phe Cys Glu Gln Glu Lys Trp Val Cys
    530                 535                 540

Val Asp Cys Val His Gly Val Val Gly Gln Pro Leu Thr Cys Tyr Lys
545                 550                 555                 560

Tyr Ala Thr Lys Pro Met Thr Tyr Val Val Gly Ile Asp Ser Asp Gly
                565                 570                 575

Trp Val Arg Asp Val Thr Gln Arg Tyr Asp Pro Val Trp Met Thr Val
            580                 585                 590

Thr Arg Lys Cys Arg Val Asp Ala Glu Trp Trp Ala Glu Thr Leu Arg
        595                 600                 605

Pro Tyr Gln Ser Pro Phe Met Asp Arg Glu Lys Lys Glu Asp Leu Glu
    610                 615                 620

Phe Gln Ala Lys His Met Asp Gln Pro Leu Pro Thr Ala Ile Gly Leu
625                 630                 635                 640

Tyr Lys Asn His Pro Leu Tyr Ala Leu Lys Arg His Leu Leu Lys Tyr
                645                 650                 655

Glu Ala Ile Tyr Pro Glu Thr Ala Ala Ile Leu Gly Tyr Cys Arg Gly
            660                 665                 670

Glu Ala Val Tyr Ser Arg Asp Cys Val His Thr Leu His Ser Arg Asp
        675                 680                 685

Thr Trp Leu Lys Lys Ala Arg Val Val Arg Leu Gly Glu Val Pro Tyr
    690                 695                 700

Lys Met Val Lys Gly Phe Ser Asn Arg Ala Lys Ala Arg Leu Ala
705                 710                 715                 720

Glu Pro Gln Leu Arg Glu Glu Asn Asp Leu Gly Leu Phe Gly Tyr Trp
                725                 730                 735

Gln Thr Glu Glu Tyr Gln Pro Pro Val Ala Val Asp Gly Lys Val Pro
            740                 745                 750

Arg Asn Glu Phe Gly Asn Val Tyr Leu Phe Leu Pro Ser Met Met Pro
        755                 760                 765

Ile Gly Cys Val Gln Leu Asn Leu Pro Asn Leu His Arg Val Ala Arg
    770                 775                 780

Lys Leu Asp Ile Asp Cys Val Gln Ala Ile Thr Gly Phe Asp Phe His
785                 790                 795                 800
```

```
Gly Gly Tyr Ser His Pro Val Thr Asp Gly Tyr Ile Val Cys Glu Glu
                805                 810                 815

Phe Lys Asp Val Leu Leu Thr Ala Trp Glu Asn Glu Gln Ala Val Ile
            820                 825                 830

Glu Arg Lys Glu Lys Glu Lys Lys Glu Lys Arg Ala Leu Gly Asn Trp
        835                 840                 845

Lys Leu Leu Ala Lys Gly Leu Leu Ile Arg Glu Arg Leu Lys Arg Arg
    850                 855                 860

Tyr Gly Pro Lys Ser Glu Ala Ala Pro His Thr Asp Ala Gly Gly
865                 870                 875                 880

Gly Leu Ser Ser Asp Glu Glu Gly Thr Ser Gln Ala Glu Ala
                885                 890                 895

Ala Arg Ile Leu Ala Ala Ser Trp Pro Gln Asn Arg Gly Asp Glu Glu
        900                 905                 910

Lys Gln Lys Leu Lys Gly Gly Pro Lys Lys Thr Lys Arg Glu Lys Lys
    915                 920                 925

Ala Ala Ala Ser His Leu Phe Pro Phe Glu Gln Leu
    930                 935                 940

<210> SEQ ID NO 23
<211> LENGTH: 4154
<212> TYPE: DNA
<213> ORGANISM: Homo sapiens

<400> SEQUENCE: 23
acttggacgc gcttgcggag gattgcgttg acgagactct tatttattgt caccaacctg     60
tggtggaatt tgcagttgca cattggatct gattcgcccc gccccgaatg acgcctgccc    120
ggaggcagtg aaagtacagc cgcgccgccc caagtcagcc tggacacata atcagcacg    180
cggccggaga accccgcaat ctctgcgccc acaaaataca ccgacgatgc ccgatctact    240
ttaagggctg aaacccacgg gcctgagaga ctataagagc gttccctacc gccatggaac    300
aacggggaca gaacgccccg gccgcttcgg gggcccggaa aaggcacggc ccaggaccca    360
gggaggcgcg gggagccagg cctgggcccc gggtccccaa gacccttgtg ctcgttgtcg    420
ccgcggtcct gctgttggtc tcagctgagt ctgctctgat cacccaacaa gacctagctc    480
cccagcagag agcggcccca caacaaaaga ggtccagccc ctcagaggga ttgtgtccac    540
ctggacacca tatctcagaa gacggtagag attgcatctc ctgcaaatat ggacaggact    600
atagcactca ctggaatgac ctccttttct gcttgcgctg caccaggtgt gattcaggtg    660
aagtggagct aagtccctgc accacgacca gaaacacagt gtgtcagtgc gaagaaggca    720
ccttccggga agaagattct cctgagatgt gccggaagtg ccgcacaggg tgtcccagag    780
ggatggtcaa ggtcggtgat gtacaccct ggagtgacat cgaatgtgtc cacaaagaat    840
caggtacaaa gcacagtggg gaagtccag ctgtggagga cggtgacc tccagcccag    900
ggactcctgc ctctccctgt tctctctcag gcatcatcat aggagtcaca gttgcagccg    960
tagtcttgat tgtggctgtg tttgtttgca agtcttact gtggaagaaa gtccttcctt   1020
acctgaaagg catctgctca ggtggtggtg gggaccctga gcgtgtggac agaagctcac   1080
aacgacctgg ggctgaggac aatgtcctca tgagatcgt gagtatcttg cagcccaccc   1140
aggtccctga gcaggaaatg gaagtccagg agccagcaga gccaacaggt gtcaacatgt   1200
tgtccccgg ggagtcagag catctgctgg aaccggcaga agctgaaagg tctcagagga   1260
ggaggctgct ggttccagca aatgaaggtg atcccactga gactctgaga cagtgcttcg   1320
```

```
atgactttgc agacttggtg ccctttgact cctgggagcc gctcatgagg aagttgggcc    1380
tcatggacaa tgagataaag gtggctaaag ctgaggcagc gggccacagg gacaccttgt    1440
acacgatgct gataaagtgg gtcaacaaaa ccgggcgaga tgcctctgtc cacaccctgc    1500
tggatgcctt ggagacgctg ggagagagac ttgccaagca gaagattgag gaccacttgt    1560
tgagctctgg aaagttcatg tatctagaag gtaatgcaga ctctgccatg tcctaagtgt    1620
gattctcttc aggaagtcag accttccctg gtttaccttt tttctggaaa aagcccaact    1680
ggactccagt cagtaggaaa gtgccacaat tgtcacatga ccggtactgg aagaaactct    1740
cccatccaac atcacccagt ggatggaaca tcctgtaact tttcactgca cttggcatta    1800
tttttataag ctgaatgtga ataaggac actatggaaa tgtctggatc attccgtttg    1860
tgcgtacttt gagatttggt ttgggatgtc attgttttca cagcactttt ttatcctaat    1920
gtaaatgctt tatttattta tttgggctac attgtaagat ccatctacac agtcgttgtc    1980
cgacttcact tgatactata tgatatgaac cttttttggg tgggggggtgc ggggcagttc    2040 actctgtctc ccaggctgga gtgcaatggt gcaatcttgg ctcactatag ccttgacctc    2100
tcaggctcaa gcgattctcc cacctcagcc atccaaatag ctgggaccac aggtgtgcac    2160
caccacgccc ggctaatttt ttgtattttg tctagatata ggggctctct atgttgctca    2220
gggtggtctc gaattcctgg actcaagcag tctgcccacc tcagactccc aaagcggtgg    2280
aattagaggc gtgagccccc atgcttggcc ttacctttct acttttataa ttctgtatgt    2340
tattatttta tgaacatgaa gaaactttag taaatgtact tgtttacata gttatgtgaa    2400
tagattagat aaacataaaa ggaggagaca tacaatgggg gaagaagaag aagtcccctg    2460
taagatgtca ctgtctgggt tccagccctc cctcagatgt actttggctt caatgattgg    2520
caacttctac aggggccagt cttttgaact ggacaacctt acaagtatat gagtattatt    2580
tataggtagt tgtttacata tgagtcggga ccaaagagaa ctggatccac gtgaagtcct    2640
gtgtgtggct ggtccctacc tgggcagtct catttgcacc catagccccc atctatggac    2700
aggctgggac agaggcagat gggttagatc acacataaca ataggggtcta tgtcatatcc    2760 caagtgaact tgagccctgt ttgggctcag gagatagaag acaaaatctg tctcccacgt    2820
ctgccatggc atcaaggggg aagagtagat ggtgcttgag aatggtgtga aatggttgcc    2880
atctcaggag tagatggccc ggctcacttc tggttatctg tcaccctgag cccatgagct    2940 gcctttagg gtacagattg cctacttgag gaccttggcc gctctgtaag catctgactc    3000
atctcagaaa tgtcaattct taaacactgt ggcaacagga cctagaatgg ctgacgcatt    3060
aaggttttct tcttgtgtcc tgttctatta ttgtttaag acctcagtaa ccatttcagc    3120
ctctttccag caaacccttc tccatagtat ttcagtcatg gaggatcat ttatgcaggt    3180 agtcattcca ggagtttttg gtcttttctg tctcaaggca ttgtgtgttt tgttccggga    3240
ctggtttggg tgggacaaag ttagaattgc ctgaagatca cacattcaga ctgttgtgtc    3300
tgtggagttt taggagtggg gggtgacctt tctggtcttt gcacttccat cctctcccac    3360
ttccatctgg catcccacgc gttgtcccct gcacttctgg aaggcacagg gtgctgctgc    3420
ctcctggtct ttgcctttgc tgggccttct gtgcaggacg ctcagcctca gggctcagaa    3480
ggtgccagtc cggtcccagg tcccttgtcc cttccacaga ggccttccta agagatgcat    3540
ctagagtgtc agccttatca gtgtttaaga ttttcttttt ttttttaatt ttttgagac    3600 agaatctcac tctctcgccc aggctggagt gcaacggtac gatcttggct cagtgcaacc    3660
```

```
tccgcctcct gggttcaagc gattctcgtg cctcagcctc cggagtagct gggattgcag    3720
gcacccgcca ccacgcctgg ctaattttg  tattttagt  agagacgggg tttcaccatg    3780
ttggtcaggc tggtctcgaa ctcctgacct caggtgatcc accttggcct ccgaaagtgc    3840
tgggattaca ggcgtgagcc accagccagg ccaagctatt cttttaaagt aagcttcctg    3900
acgacatgaa ataattgggg gttttgttgt ttagttacat taggctttgc tatatcccca    3960
ggccaaatag catgtgacac aggacagcca tagtatagtg tgtcactcgt ggttggtgtc    4020
ctttcatgct tctgccctgt caaaggtccc tatttgaaat gtgttataat acaaacaagg    4080
aagcacattg tgtacaaaat acttatgtat ttatgaatcc atgaccaaat taaatatgaa    4140
accttatata aaaa                                                     4154
```

<210> SEQ ID NO 24
<211> LENGTH: 440
<212> TYPE: PRT
<213> ORGANISM: Homo sapiens

<400> SEQUENCE: 24

```
Met Glu Gln Arg Gly Gln Asn Ala Pro Ala Ser Gly Ala Arg Lys
1               5                   10                  15

Arg His Gly Pro Gly Pro Arg Glu Ala Arg Gly Ala Arg Pro Gly Pro
                20                  25                  30

Arg Val Pro Lys Thr Leu Val Leu Val Val Ala Val Leu Leu Leu
            35                  40                  45

Val Ser Ala Glu Ser Ala Leu Ile Thr Gln Gln Asp Leu Ala Pro Gln
    50                  55                  60

Gln Arg Ala Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
                85                  90                  95

Cys Lys Tyr Gly Gln Asp Tyr Ser Thr His Trp Asn Asp Leu Leu Phe
            100                 105                 110

Cys Leu Arg Cys Thr Arg Cys Asp Ser Gly Glu Val Glu Leu Ser Pro
        115                 120                 125

Cys Thr Thr Thr Arg Asn Thr Val Cys Gln Cys Glu Glu Gly Thr Phe
    130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175

Glu Cys Val His Lys Glu Ser Gly Thr Lys His Ser Gly Glu Val Pro
            180                 185                 190

Ala Val Glu Glu Thr Val Thr Ser Ser Pro Gly Thr Pro Ala Ser Pro
        195                 200                 205

Cys Ser Leu Ser Gly Ile Ile Ile Gly Val Thr Val Ala Ala Val Val
    210                 215                 220

Leu Ile Val Ala Val Phe Val Cys Lys Ser Leu Leu Trp Lys Lys Val
225                 230                 235                 240

Leu Pro Tyr Leu Lys Gly Ile Cys Ser Gly Gly Gly Asp Pro Glu
                245                 250                 255

Arg Val Asp Arg Ser Ser Gln Arg Pro Gly Ala Glu Asp Asn Val Leu
            260                 265                 270

Asn Glu Ile Val Ser Ile Leu Gln Pro Thr Gln Val Pro Glu Gln Glu
        275                 280                 285
```

Met Glu Val Gln Glu Pro Ala Glu Pro Thr Gly Val Asn Met Leu Ser
    290                 295                 300

Pro Gly Glu Ser Glu His Leu Leu Glu Pro Ala Glu Ala Glu Arg Ser
305                 310                 315                 320

Gln Arg Arg Arg Leu Leu Val Pro Ala Asn Glu Gly Asp Pro Thr Glu
                325                 330                 335

Thr Leu Arg Gln Cys Phe Asp Asp Phe Ala Asp Leu Val Pro Phe Asp
                340                 345                 350

Ser Trp Glu Pro Leu Met Arg Lys Leu Gly Leu Met Asp Asn Glu Ile
            355                 360                 365

Lys Val Ala Lys Ala Glu Ala Ala Gly His Arg Asp Thr Leu Tyr Thr
    370                 375                 380

Met Leu Ile Lys Trp Val Asn Lys Thr Gly Arg Asp Ala Ser Val His
385                 390                 395                 400

Thr Leu Leu Asp Ala Leu Glu Thr Leu Gly Glu Arg Leu Ala Lys Gln
                405                 410                 415

Lys Ile Glu Asp His Leu Leu Ser Ser Gly Lys Phe Met Tyr Leu Glu
                420                 425                 430

Gly Asn Ala Asp Ser Ala Met Ser
            435                 440

<210> SEQ ID NO 25
<211> LENGTH: 3134
<212> TYPE: DNA
<213> ORGANISM: Homo sapiens

<400> SEQUENCE: 25
agtcggagcc gggcttgccc gggcatgtgg gagctgccgg ctttccggac gccacgtgca    60
gaccggaaga gacacgcggg gcttcaggct gctgccccat tggaagatta ctccccaggc   120
ttcccttgcc ccaagcagtg agctgactgg aatggtaccc cgggaggccc ctgagtctgc   180
tcagtgcctg tgcccttccc tcaccatccc aaatgccaag gatgtgcttc ggaagaggca   240
caagagaagg agccgacagc accagcggtt catggcccgg aaggccttgc tgcaggagca   300
ggggctgctg agcatgcctc cagaaccagg gtcctcccca ctgcccaccc ctttcggggc   360
agcgacagca actgaagctg ccagcagtgg gaagcagtgt ctgagggctg gatctggcag   420
tgccccatgc agcagaaggc ctgctcccgg gaaagcctca gggcccttgc ccagcaagtg   480
tgtggctatc gactgtgaga tggtgggcac gggaccccga gggcgggtaa gcgagctggc   540
ccgctgttcc attgtgagct accatggcaa tgtcctctat gacaagtaca tcaggcctga   600
gatgcccatc gctgactacc gtacccgctg gagtggcatc actcggcagc acatgcgcaa   660
ggctgtcccc ttccaggtgg cccagaaaga gatccttaag ctcctgaagg caaggtggt   720 ggtggggcac gcgctgcaca cgacttccag gcgctcaag tatgtccacc ctcggagcca   780
gacccgggat acgacctatg tcccaaactt cctcagcgag cccggcctcc acacccgggc   840
ccgggtctct ctaaaggacc tggccctgca gctgctgcac aagaagatcc aggtgggcca   900
gcacgggcac tcatcagtag aagatgccac gacagccatg gagctctacc ggctggtgga   960
ggtgcagtgg gaacagcagg aggcccgcag cctctgacc tgccccgagg acagagaacc  1020
tgacagcagc acagacatgg aacagtacat ggaggaccag tactggcccg atgacctggc  1080
ccacggcagc agaggaggag ccaggggaggc acaggacaga aggaattgag aagggggcgg  1140
ggctccctgg ctgggcttcc ggtgtggccg gtaggaagtg ggggcaggga gagcagcggg  1200

```
cactccttcc tgggcagggt ggggcaggat gcagtgagcc agccccaggg ccagaggagt    1260
aggggtcatc tgttaccttg acaccctctg cacacagcat agccctctct ctctccaggg    1320
ctgttggttc tttctcctga ctcctgtggt tttgctaatg cactttaca gactccatgg     1380 agatgtcagg tggaccatct tctagggccc agcaggagta gggaatgtgc aacagactg     1440 cccaggttgc cgtggccttc ccaccccc agatctcctg agtcatcatg ctgtgctaat      1500
gaaagggatc atatcatcct ctctggggat ggtgggtggg ggtgtcaata tcctggagct    1560
cccttacccc aactcaatga cttgggggta aagttctctt cctttgttg cctacctctt     1620 cctccactca tttgggttca gaataaacat gccctgaagt taaagaggag ttaagtccta    1680
aaggaggcat ttcttcccca cctccctgac ctggaactct ggctacagcc attgtaggaa    1740
ctccgtgcct ggcctgtcag ctccctgcta ggctacagtg aatagcaga gcccacaggc     1800 ttctcgtggg gagttggctc cttaacattt cttggcaaca gaaagcccca ggcacagctc    1860
agggaggagg gaaggcaggt aagctttgga cgagaactgg catatttatt ttgacccaaa    1920
tcagggattt ccccagtcca cccagtactg ggctcttaag caaaagtctg agaaacaaga    1980
cagtggtttg aattctgggg cctttgtgta ggattgtgcc tgacctttat ttatttatta    2040
acagcagggc cactcgtcta gggcagtgga gtctgcgtgt ctcctggggc tggggcaggg    2100
cattggcagt tacgcagtgg ccctgaacct ggtctggtgc cccgaacct ggtctgatgc     2160 cccctcagct ctttgacaat cactgtggct gttgggtttt ctcctatttc taaaaatgtt    2220
ctcttctttc ctaagtgaca gttttgaagt attggataac caagagctca ggtcacacag    2280
accttggagc cccatctttg cttgcagctt agctttgaga tactaagcaa gcagggact     2340 tcactcttga ggctgttttt tcctcatctg taaagtgggg atagtggtac ggcctacctc    2400 ataggggttgt aatgagcact aaatgtgaag tgcttggcac agtgcctggc acatggtgag   2460
ccacagctac tgtgagtttc tgtttatccc cttttttt ttttaagccc attgtttatt       2520 cttttgagaat ttgttgtaac ttcttcagga taacacctga gtccacaggc tgagcagctg   2580
tggcccagac agaactgctc cggcttggct gttccagcag gtgggcgct ggcctcggtg     2640 agggcacagc agcaaggttc acggatatcc gtgtgtcttg tctgtggcca ccaggcacag    2700
gtttggcttc cggtcagtgt cccgacactg tgcgggaggt gacaacagag caaagcagcg    2760
caggggtcag ggaggtacag acactgctga aatcacacta ccccaccctc agctgaagcc    2820
ccacgttcca caaacttggg gtcatagatt gtccagtcac tggctccctc cctgtcagca    2880
cagcacagag gaaggggcta actgaatctt ttaccacttc tggcctggct ccagaacttt    2940
gttctagatt ccttaaaagt cggtagctga tgtcaaactc aattgagcag tagctttgat    3000
cccttggtct gggggtcgaa ggaagatggt gctgttatca gcggggaaat gtactattta    3060
agatcagctt tgttgtaaaa ccatttgttc tagaataaaa ctcaattgga aacgtgaaaa    3120
aaaaaaaaaa aaaa                                                      3134
```

<210> SEQ ID NO 26
<211> LENGTH: 325
<212> TYPE: PRT
<213> ORGANISM: Homo sapiens

<400> SEQUENCE: 26

```
Met Val Pro Arg Glu Ala Pro Glu Ser Ala Gln Cys Leu Cys Pro Ser
1               5                   10                  15

Leu Thr Ile Pro Asn Ala Lys Asp Val Leu Arg Lys Arg His Lys Arg
            20                  25                  30
```

-continued

```
Arg Ser Arg Gln His Gln Arg Phe Met Ala Arg Lys Ala Leu Leu Gln
     35                  40                  45
Glu Gln Gly Leu Leu Ser Met Pro Pro Glu Pro Gly Ser Ser Pro Leu
 50                  55                  60
Pro Thr Pro Phe Gly Ala Ala Thr Ala Thr Glu Ala Ala Ser Ser Gly
 65              70                  75                  80
Lys Gln Cys Leu Arg Ala Gly Ser Gly Ser Ala Pro Cys Ser Arg Arg
             85                  90                  95
Pro Ala Pro Gly Lys Ala Ser Gly Pro Leu Pro Ser Lys Cys Val Ala
             100                 105                 110
Ile Asp Cys Glu Met Val Gly Thr Gly Pro Arg Gly Arg Val Ser Glu
             115                 120                 125
Leu Ala Arg Cys Ser Ile Val Ser Tyr His Gly Asn Val Leu Tyr Asp
         130                 135                 140
Lys Tyr Ile Arg Pro Glu Met Pro Ile Ala Asp Tyr Arg Thr Arg Trp
145                 150                 155                 160
Ser Gly Ile Thr Arg Gln His Met Arg Lys Ala Val Pro Phe Gln Val
             165                 170                 175
Ala Gln Lys Glu Ile Leu Lys Leu Leu Lys Gly Lys Val Val Val Gly
             180                 185                 190
His Ala Leu His His Asn Asp Phe Gln Ala Leu Lys Tyr Val His Pro Arg
         195                 200                 205
Ser Gln Thr Arg Asp Thr Thr Tyr Val Pro Asn Phe Leu Ser Glu Pro
     210                 215                 220
Gly Leu His Thr Arg Ala Arg Val Ser Leu Lys Asp Leu Ala Leu Gln
225                 230                 235                 240
Leu Leu His Lys Lys Ile Gln Val Gly Gln His Gly His Ser Ser Val
             245                 250                 255
Glu Asp Ala Thr Thr Ala Met Glu Leu Tyr Arg Leu Val Glu Val Gln
             260                 265                 270
Trp Glu Gln Gln Glu Ala Arg Ser Leu Trp Thr Cys Pro Glu Asp Arg
         275                 280                 285
Glu Pro Asp Ser Ser Thr Asp Met Glu Gln Tyr Met Glu Asp Gln Tyr
     290                 295                 300
Trp Pro Asp Asp Leu Ala His Gly Ser Arg Gly Gly Ala Arg Glu Ala
305                 310                 315                 320
Gln Asp Arg Arg Asn
             325
```